US007081342B2

(12) United States Patent
Mengeling et al.

(10) Patent No.: US 7,081,342 B2
(45) Date of Patent: Jul. 25, 2006

(54) PORCINE REPRODUCTIVE AND RESPIRATORY SYNDROME VACCINE, BASED ON ISOLATE JA-142

(75) Inventors: William L. Mengeling, Ames, IA (US); Ann Vorwald, Ames, IA (US); Kelly Lager, Neveda, IA (US); Kelly Burkhart, Radcliffe, IA (US); David E. Gorcyca, St. Joseph, MO (US); Mike Roof, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 315 days.

(21) Appl. No.: 10/654,545

(22) Filed: Sep. 3, 2003

(65) Prior Publication Data

US 2004/0087002 A1 May 6, 2004

Related U.S. Application Data

(63) Continuation of application No. 09/981,282, filed on Oct. 18, 2001, now Pat. No. 6,641,819, which is a continuation-in-part of application No. 09/461,879, filed on Dec. 15, 1999, now abandoned, which is a continuation-in-part of application No. 09/298,110, filed on Apr. 22, 1999, now abandoned.

(51) Int. Cl.
*C12Q 1/68* (2006.01)

(52) U.S. Cl. ......................... 435/6; 435/69.1; 435/91.2

(58) Field of Classification Search .................... 435/6, 435/91.2, 69.1

See application file for complete search history.

(56) References Cited

U.S. PATENT DOCUMENTS 4,554,159 A 11/1985 Roizman et al.
5,476,778 A 12/1995 Chladek et al.
5,510,258 A 4/1996 Sanderson et al.
5,587,164 A 12/1996 Sanderson et al.
5,698,203 A 12/1997 Visser et al.
5,840,563 A 11/1998 Chladek et al.
5,846,805 A 12/1998 Collins et al.
5,925,359 A 7/1999 Woensel et al.

(Continued)

FOREIGN PATENT DOCUMENTS

EP 595436 5/1994

(Continued)

OTHER PUBLICATIONS

Andreyev, et al.; Genetic variation and phylogenetic relationships of 22 porcine reproductive and respiratory syndrome virus (PRRSV) field strains based on sequence analysis of open reading frame 5; Arch Virol (1997) 142: 993-1001.

(Continued)

*Primary Examiner*—Ali R. Salimi
(74) *Attorney, Agent, or Firm*—Hovey Williams LLP

(57) ABSTRACT

Substantially avirulent forms of atypical porcine reproductive and respiratory syndrome (PRRS) virus and corresponding vaccines are provided which result from cell culture passaging of virulent forms of PRRS. The resultant avirulent atypical PRRS virus is useful as a vaccine in that PRRS specific antibody response is elicited by inoculation of host animals, thereby conferring effective immunity against both previously known strains of PRRS virus and newly isolated atypical PRRS virus strains. The preferred passaging technique ensures that the virus remains in a logarithmic growth phase substantially throughout the process, which minimizes the time required to achieve attenuation. The present invention also provides diagnostic testing methods which can differentiate between animals infected with field strains and attenuated strains of PRRSV.

7 Claims, 2 Drawing Sheets

U.S. PATENT DOCUMENTS

| | | | |
|---|---|---|---|
| 6,042,830 A | 3/2000 | Chladek et al. | |

FOREIGN PATENT DOCUMENTS

| | | | |
|---|---|---|---|
| EP | 0676467 | | 4/1995 |
| WO | 9303760 | | 3/1993 |
| WO | 9418311 | | 8/1994 |
| WO | W) 97/31652 | * | 9/1997 |

OTHER PUBLICATIONS

Flint et al; Virus Cultivation, Detection, and Genetics; Arch Virol (2000) Chapter 2 40-42.

Gong et al.; Characterization of RNA Synthesis during a one-step growth curve and of the replication mechanism of bovine viral diarrhoea virus; Journal of General Virology (1996) 77 2729-2736.

Horsfall et al.; General Principles of Animal Virus Multiplication; Viral and Rickettsial Infections of Man (1965) 239-241.

Mengeling et al.; An update of research at the National Animal Disease Center on current field strains of Porcine Reproductive and Respiratory Syndrome (PRRS) virus; 1997 Allen D. Leman Swine Conference; 138-145.

Nuttall; Growth Characteristics of Two Strains of Bovine Virus Diarrhoea Virus; Arch Virol (1980) 66 365-369.

Wesley et al.; Differentiation of Vaccine (Strain Resp-PRRS®) and Field Strains of Porcine Reproductive and Respiratory Syndrome Virus by Restriction Enzyme Analysis; American Association of Swine Practitioners (1996) 141-143.

For purification of viral RNA from Plasma, Serum, Cell-free body fluids, Cell-culture supernatants; QIAamp® Viral RNA Mini Kit Handbook; QIAGEN (1999) Cat # 52906 1-35.

Enzo Biochem Inc. v Gen-Probe Incorporated et al; No. 01-01230; Decided Jul. 15, 2002.

* cited by examiner

PORCINE REPRODUCTIVE AND RESPIRATORY SYNDROME VACCINE, BASED ON ISOLATE JA-142

RELATED APPLICATION

This is a continuation of application Ser. No. 09/981,282 filed Oct. 18, 2001 now U.S. Pat. No. 6,641,819 which is a continuation-in-part of application Ser. No. 09/461,879 filed Dec. 15, 1999 now abandoned which is a continuation-in-part of application Ser. No. 09/298,110 filed Apr. 22, 1999 now abandoned.

SEQUENCE DISCLOSURE

A Sequence Listing in the form of a computer readable ASCII file in connection with the present invention was filed in application Ser. No. 09/981,282. This earlier filed CRF is incorporated herein by reference and applicant requests that this previously filed CRF be used as the CRF for this application. A paper copy of this sequence is included herein and is identical to this previously-filed CRF.

BACKGROUND OF THE INVENTION

1. Field of the Invention

The present invention is broadly concerned with attenuated avirulent atypical porcine reproductive and respiratory syndrome (PRRS) virus (PRRSV), and corresponding live virus vaccines for administration to swine in order to confer effective immunity in the swine against PRRSV. The invention also includes methods of immunizing swine against PRRSV, and a new, highly efficient method of passaging viruses to attenuation. Furthermore, the invention provides methods of detecting and differentiating between field strains and an attenuated strain of PRRSV.

2. Description of the Prior Art

PRRS emerged in the late 1980's as an important viral disease of swine. PRRSV causes severe reproductive failure in pregnant sows, manifested in the form of premature farrowings, increased numbers of stillborn, mummified and weak-born pigs, decreased farrowing rate, and delayed return to estrus. Additionally, the respiratory system of swine infected with PRRSV is adversely affected, which is evidenced by lesions that appear in the lungs of infected swine. To combat the problems associated with PRRSV infection, vaccines have been developed which conferred immunity to then extant PRRSV strains.

Epidemics of an unusually severe form of PRRS, referred to hereafter as "atypical PRRS", were first recognized in North America in the latter part of 1996. They differed from epidemics of "typical PRRS" in that: 1) clinical signs were more prolonged as well as more severe; 2) the incidence of abortion was greater, especially during early and middle gestation; 3) there was a higher incidence of gilt and sow mortality; 4) PRRSV was less often isolated from aborted fetuses, stillborn pigs, and liveborn pigs—perhaps because abortions were more often the result of acute maternal illness rather than transplacental infection; 5) lung lesions of young affected pigs were more extensive; and 6) commercially available vaccines provided little or no protection. Collectively these observation indicated the emergence of more virulent and antigenically distinct strains of PRRSV and the need for a new generation of PRRS vaccines.

The most frequently used method for producing attenuated, live-virus vaccine is to serially passage the virus in a substrate (usually cell culture) other than the natural host (S) until it becomes sufficiently attenuated (i.e., reduced in virulence or diseases-producing ability) to be used as a vaccine. For the first passage, a cell culture is infected with the selected inoculum. After obtaining clear evidence of virus replication (e.g., virus-induced cytopathic effects [CPE] in the infected cells), an aliquot of the cell culture medium, or infected cells, or both, of the first passage are used to infect a second cell culture. The process is repeated until one or more critical mutations in the viral genome cause sufficient attenuation so that the virus can be safely used as a vaccine. The degree of attenuation is usually determined empirically by exposing the natural host (S) to progressively greater passage levels of the virus.

The above procedure is fundamentally sound and has been successfully used for the development of numerous vaccines for human and veterinary use. However, it is relatively inefficient because the logarithmic phase of virus replication, during which mutations are most likely to occur, is often completed long before evidence of virus replication becomes visibly obvious.

Therefore, there is a decided need in the art for a vaccine that confers effective immunity against PRRSV strains, including recently discovered atypical PRRSV strains. There is also a need in the art for a method of making such a vaccine. Finally, what is needed is a method of passaging a virus that attenuates the virus more efficiently than was heretofore thought possible with the resulting attenuated virus eliciting PRRSV specific antibodies in swine thereby conferring effective immunity against subsequent infection by PRRSV.

SUMMARY OF THE INVENTION

The present invention overcomes the problems outlined above, and provides attenuated, atypical PRRSV strains, and corresponding improved modified-live vaccines which confer effective immunity to newly discovered atypical PRRSV strains. "Effective immunity" refers to the ability of a vaccine to prevent swine PRRSV infections, including atypical PRRSV infections, which result in substantial clinical signs of the disease. That is to say, the immunized swine may or may not be serologically positive for PRRSV, but do not exhibit any substantial clinical symptoms. "Atypical PRRSV" refers to these new strains of PRRSV that are substantially more virulent than typical PRRSV strains.

In preferred forms, the vaccine of the invention includes live virus which has been attenuated in virulence. The resulting attenuated virus has been shown to be avirulent and to confer effective immunity. A particularly virulent strain of atypical PRRS (denominated JA-142) which caused especially severe symptoms of PRRS and represents the dominant strain of atypical PRRSV, was chosen for subsequent attenuation through passaging. The resultant attenuated virus has been deposited in the American Type Culture Collection (ATCC), Rockville, Md. on Feb. 2, 1999, and was accorded ATCC Accession No. VR-2638. This attenuated virus is a preferred Master Seed Virus (MSV) which has been subsequently passaged and developed as an effective PRRSV vaccine.

The name given the unattenuated virus, JA-142, arises from the restriction enzyme pattern. The 1 represents the inability of the enzyme MLUI to cleave the virus in open reading frame 5 (ORF 5. The 4 represents cleavage by Hinc II at base pair positions 118 and 249 of ORF 5 and short contiguous sequences. The 2 represents cleavage by Sac II at base pair position 54 of ORF 5 and short contiguous sequences.

Additionally, the present invention provides another way to differentiate between field strains of PRRSV and strain JA-142. The method is based upon differences in RNA cleavage by a restriction enzyme, NspI. Briefly, isolated PRRSV RNA is subjected to digestion by NspI. Digestion of the attenuated strain, JA-142, results in at least one additional fragment in comparison to field strains of PRRSV. In preferred methods, the RNA is isolated and RT-PCR is performed on the isolated RNA. This RNA is then subject to electrophoresis and a 1 Kd product is identified and purified for digestion by NspI. This digestion results in three fragments for JA-142 and either one or two fragments for PRRSV field strains.

Passaging of the virus to attenuation was accomplished using a novel method which resulted in increased efficiency. Specifically, the virus was kept in the logarithmic phase of replication throughout multiple cell culture passages in order to materially shorten the time to attenuation. This is achieved by ensuring that in each cell culture there is a substantial excess of initially uninfected cells relative to the number of virus present. Thus, by transferring only small numbers of virus from passage-to-passage, logarithmic replication is assured.

In practice, the process is normally initiated by inoculation of several separate cell cultures with progressively smaller viral aliquots (i.e., lesser numbers of virus in each culture.) For example, starting cultures could contain 200 μl, 20 μl and 2 μl viral aliquots. After an initial short incubation period (e.g., ~24 hours), the same viral aliquots (in the example, 200 μl 20 μl and 2 μl) from each cell culture are transferred to individual fresh (previously uninfected) cultures, while the starting cultures are monitored until cytopathic effect (CPE) is or is not observed. This process is continued in serial order for multiple passages, using the same viral aliquots in each case and preserving the cultures for CPE observation. If all of the serial culture passages exhibit CPE after a selected number of passages are complete, the larger viral aliquot series may be terminated (in the example 200 μl and 20 μl), whereupon another series of progressively smaller viral aliquots are employed (e.g., 2 μl, 0.2 μl and 0.02 μl) and the process is again repeated, again keeping the cell cultures after transfer for CPE observation.

At some point in this successively smaller viral aliquot inoculation process, CPE will not be observed in a given cell culture. When this occurs, the next higher viral aliquot level showing CPE is substituted for the passage in which CPE was not observed, whereupon subsequent passages will be inoculated using previously employed viral aliquots.

Inasmuch as a virus will tend to become more efficient at infecting cells and also replicate to a higher infectivity titer for cell cultures over time, (which is especially true with RNA viruses such as PRRSV), it will be seen that smaller and smaller viral aliquots are required to maintain infection during serial transfer. The use of the smallest aliquot that maintains infection helps to assure that viral replication remains in a logarithmic phase throughout the process.

The DNA sequence of the attenuated passaged virus from the 201st passage was then determined using conventional methods. The sequence of this attenuated virus was designated as MSV JA-142 Passage No. 201, the sequence of which is given as SEQ ID No. 1. The sequence of the virulent virus, JA-142, is given as SEQ ID No. 2.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403–410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, “sequence homology”, as used herein, also refers to a method of determining the relatedness of two sequences. To determine sequence homology, two or more sequences are optimally aligned as described above, and gaps are introduced if necessary. However, in contrast to “sequence identity”, conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A “conservative substitution” refers to the substitution of an amino acid residue or nucleotide with another amino acid residue or nucleotide having similar characteristics or properties including size, hydrophobicity, etc., such that the overall functionality does not change significantly.

Isolated" means altered “by the hand of man” from its natural state., i.e., if it occurs in nature, it has been changed or removed from its original environment, or both. For example, a polynucleotide or polypeptide naturally present in a living organism is not “isolated,” but the same polynucleotide or polypeptide separated from the coexisting materials of its natural state is “isolated”, as the term is employed herein.

Preferably, sequences sharing at least about 75%, more preferably at least about 85%, still more preferably at least about 90% and most preferably at least about 95% sequence homology with SEQ ID No. 1 are effective as conferring immunity upon animals vaccinated with attenuated viruses containing such homologous sequences. Alternatively, sequences sharing at least about 65%, more preferably at least about 75%, still more preferably at least about 85%, and most preferably at least about 95% sequence identity with SEQ ID No. 1 are also effective at conferring immunity upon animals vaccinated with attenuated viruses containing such identical sequences.

DETAILED DESCRIPTION OF THE PREFERRED EMBODIMENT

Figure 1:
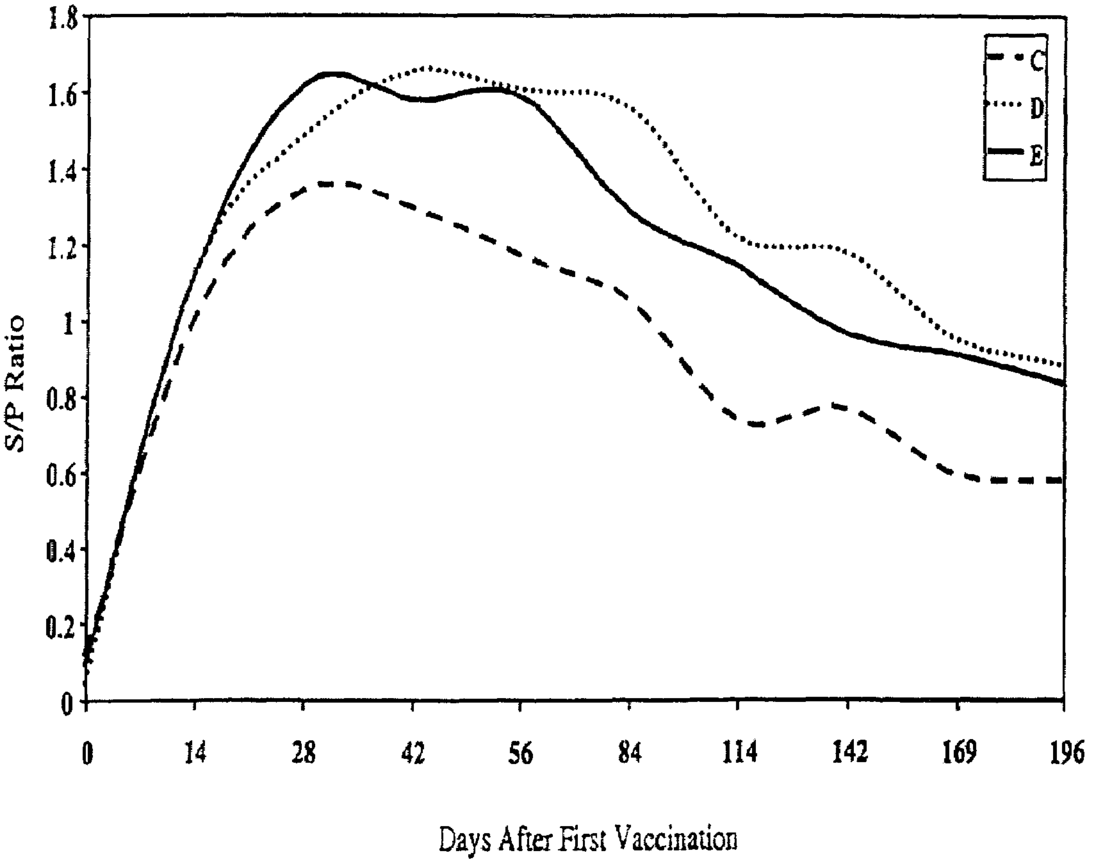
FIG. 1 is a graph illustrating the ratio of samples which tested positive for antibodies against PRRSV to the total number of samples over a 196 day testing period.

The following examples set forth preferred embodiments of the present invention. It is to be understood, however, that these examples are provided by way of illustration and nothing therein should be taken as a limitation upon the overall scope of the invention.

EXAMPLE 1

Materials and Methods

This example describes a passage method of attenuating viruses which maximizes attenuation efficiency by ensuring that the virus is preferably in a logarithmic phase of replication. Virus was passed (i.e. an aliquot of nutrient medium including the virus, unattached cells, and cell debris from a virus-infected cell culture was added to the nutrient medium of a noninfected culture) at daily intervals. Different amounts of virus were added at each interval by using multiple cultures. For example, at the beginning, 200 μl was transferred to one noninfected culture, 20 μl was added to a second noninfected culture, and 2 μl to a third noninfected culture. The goal was to have a sufficient amount of susceptible cells so that the replication cycles could continue until the next transfer. The procedure was deemed successful if the cells eventually showed CPE. However, because PRRSV-induced CPE do not appear until sometime after the logarithmic growth phase, passages were made before it was known whether or not they would be ultimately successful (“blind passages”). Passages that resulted in virus induced CPE were said to have resulted in a “take”. If a passage did not result in a take, the passage was restarted using the highest dilution from the last passage which did result in a take. As more and more passages were made, the virus became more adapted to replicate in the cell line and less able to produce disease symptoms in its original host. These changes occur through random mutations that occur during replication.

Using this method, the following procedures were used to passage an exemplary virus in accordance with the present invention, MSV, JA-142. This strain was passaged in MARC-145 cell cultures at daily intervals. Twenty-four-well plates were used for the process to minimize the amount of cells and nutrient medium required, and to simplify the multiple-aliquot passage technique. Cells and nutrient medium were added to each well and the cells were allowed to form, or nearly form (greater than about 70%), a confluent monolayer. The nutrient medium comprised approximately 90% Earle’s balanced salt solution minimal essential medium (MEM), 10% fetal calf serum and 0.05 mgm/ml of gentamicin sulfate. The volume of nutrient medium used was approximately 1 ml. Usually, three wells of a column were used for each amount of virus that was transferred. An aliquot of nutrient medium from the previous passage was transferred to the first well in the column at 48 or 72 hours, after the cell cultures had been prepared, nutrient medium from the first well was transferred to the second well of the same column at 72 or 96 hours and the third well of the same column at 96 or 120 hours. Plates were usually set up twice a week so sometimes the fourth well of the column was used and sometimes it was not used. Passaging conditions were maintained at 37° C. in a moist atmosphere containing 5% $CO_2$.

Different sized aliquots (having different amounts of virus) for each passage were tested to determine if the amount of virus was sufficient to induce CPE. For example, a separate series of aliquot transfers (passages) of 200 μl, 20 μl, and 2 μl, respectively, was used until the smaller aliquots consistently exhibited CPE with the goal being to transfer the smallest aliquot that produced CPE. When the smallest aliquot (e.g. 2 μl) of the group of aliquots being tested consistently resulted in CPE, smaller amounts were tested (e.g. 0.2 μl and 0.02 μl). When a certain dilution did not exhibit CPE, that series of cultures was restarted with the next lower amount which did result in CPE at that passage (i.e. if the 2 μl transfer was unsuccessful at producing CPE in the 25th passage but the 20 μl transfer in the 25th passage was successful, the 2 μl transfer was repeated using 20 μl with 2 μl transfers resuming for the 26th passage.)

Using this method, the smallest amount of virus necessary to transfer to obtain CPE was determined. Virus was passed successfully at daily intervals using the following amounts of virus-infected nutrient medium (which reflect the highest dilution [i.e., smallest aliquot] which resulted in CPE keeping in mind that other dilutions would also work):

| Passage Number | Amount Transferred |
|---|---|
| 3–21 | 200 μl |
| 22, 23 | 20 μl |
| 24–41 | 200 μl |
| 42–83 | 20/200 μl (alternating) |
| 84–90 | 20 μl |
| 91–112 | 2 μl |
| 113 | 0.2 μl |
| 114–116 | 2 μl |
| 117 | 0.2 μl |
| 118–120 | 2 μl |
| 121 | 0.2 μl |
| 122–124 | 2 μl |
| 125–167 | 0.2 μl |
| 168 | 0.02 μl |
| 169–171 | 0.2 μl |
| 172 | 0.02 μl |
| 173–175 | 0.2 μl |
| 176 | 0.02 μl |
| 177–179 | 0.2 μl |
| 180 | 0.02 μl |
| 181–183 | 0.2 μl |
| 184 | 0.02 μl |
| 185–187 | 0.2 μl |
| 188 | 0.02 μl |
| 189–191 | 0.2 μl |
| 192 | 0.02 μl |
| 193–195 | 0.2 μl |
| 196 | 0.02 μl |
| 197 | 0.2 μl |

Results and Discussion

The passaging of the virus using the above method resulted in an attenuated PRRSV, JA-142. As is apparent, the virus became more adapted to replicate in the cell culture and therefore required a smaller amount of virus-infected nutrient medium to be transferred as passaging continued. For transfers using a very small amount of virus-infected nutrient medium (e.g. 0.2 μl or 0.02 μl), a separate dilution was required. This dilution was accomplished by adding a small amount of virus-infected nutrient medium to a larger amount of nutrient medium. For example, to obtain a transfer of 0.2 μl, 2 μl of virus infected nutrient medium was added to 20 μl of nutrient medium and 2 μl of this dilution was added to the next culture in the series. Using this approach, the highest dilution which resulted in CPE was used and the time necessary for passaging the virus was minimized. Passaging at daily intervals ensured that the virus was always in a logarithmic phase of replication. Daily transferring also ensured that there was an adequate number of cells for virus replication.

Because the mutations (which are probably cumulative) that are likely to result in attenuation only occur during replication, there is no advantage to having substantially all cells infected and replication either proceeding at a slower rate or stopping before the next transfer. Based on previous studies of PRRSV, it was known that the replication cycle is about 8 hours, therefore, transferring a minimal amount of virus from virus-infected nutrient medium to uninfected nutrient medium at daily intervals results in the virus always having plenty of cells within which to replicate.

As can be readily appreciated, passaging using this method results in a savings of time that was heretofore thought impossible (i.e. each passage required less time). This is especially important when a high number of passages are required for adequate virus attenuation. If each passage, using old methods, was performed at a 3 day interval, a procedure requiring 200 passages would take 400 fewer days using the method of the present invention.

EXAMPLE 2

Materials and Methods

This example determined if passage 200 of PRRS Virus, JA-142, would revert in virulence when passed in the host animal six times. This study consisted of six groups. Five pigs from group 1 (principle group) were inoculated intranasally with PRRS MSV, JA-142 passage 200, while three pigs from group 1A, (control group) were inoculated intranasally with sterile diluent. The animals were provided commercial feed and water ad libitum throughout the study. Pigs of both treatment groups were monitored daily for clinical signs (appearance, respiratory, feces, etc.). After six days, the animals were weighed, bled and sacrificed. After scoring the lungs for lesions, lung lavages were collected from each animal. The lung lavages were frozen and thawed one time, and a pool was prepared using 2.0 ml of serum and 2.0 ml of lung lavage from each animal within a group to prepare Backpassage 1 and 1A, respectively. This pool was used to challenge (intra-nasally) the animals in group 2 and group 2A, respectively. This process was repeated for groups 3 and 3A through 6 and 6A. Animals in each group were housed in separate but identical conditions.

Following inoculation, blood samples were collected and body temperatures were monitored. Rectal temperatures were measured for each animal periodically from −1 DPE (days post exposure) to 6 DPE and averaged together with other animal temperatures from the same group. The health status of each animal was monitored daily for the duration of the study. Results were compiled and scored on a daily observation form. The scoring parameters are as follows:

1. Appearance
   normal = 0; depressed = 1; excited = 2; comatose/death = 30.
2. Respiration
   normal = 0; sneeze = 1; cough = 1; rapid/short = 2; labored = 3.
3. Feces
   normal = 0; dry = 1; loose = 2; fluid = 3.
4. Eyes
   normal = 0; watery = 1; matted = 2; sunken = 3.
5. Nostrils
   normal = 0; watery discharge = 1; red/inflamed = 2; crusted ulcers = 3.

-continued

| | |
|---|---|
| 6. | Mouth<br>normal = 0; slobbers = 2; ulcer = 3. |
| 7. | Activity<br>NA |
| 8. | Appetite<br>normal = 0; decreased = 1; anorexic (none) = 3. |
| 9. | Other |

Animals were also weighed prior to inoculation and at necropsy. Average weight gains for each group were calculated for comparison. PRRS Enzyme Linked Immuno-Absorbent Assays (ELISA) and serum neutralization (SN) assays were performed following the exposures of the animals with test and control articles. Attempts to isolate PRRSV from serum samples were performed on MA-104 cells. Prior to and following vaccination, total white blood cell counts were determined using COULTER COUNTER MODEL Z1, Coulter Corp., Miami, Fla. At necropsy, the lungs of each animal were scored. Lung scoring was done by separating the lung into 7 sections and determining the percentage of lung involvement (the percentage of the lung area affected as shown by lesions or redness for each section and multiplying by the approximate area of the whole lung) that percentage of total lung area that the section encompasses. Parameters for lung scoring are as follows:

| | | |
|---|---|---|
| Left Apical Lobe % of involvement × | 0.10 = | ____ |
| Left Cardiac Lobe % of involvement × | 0.10 = | ____ |
| Left Diaphragmatic Lobe % of involvement × | 0.25 = | ____ |
| Right Apical Lobe % of involvement × | 0.10 = | ____ |
| Right Cardiac Lobe % of involvement × | 0.10 = | ____ |
| Right Diaphragmatic Lobe % of involvement × | 0.25 = | ____ |
| Intermediate Lobe of Right Lung % of involvement × | 0.10 = | ____ |
| Total (Sum of all values in the far right column) | = | ____ |

Results and Discussion

Each group of pigs was monitored for six days following vaccination. Clinical scores were low in all groups. Clinical score results are given in Table 1.

TABLE 1

| | | Daily Clinical Scores | | | | | | | | |
|---|---|---|---|---|---|---|---|---|---|---|
| Treatment | Pig # | Day-1 | Day 0 | Day 1 | Day 2 | Day 3 | Day 4 | Day 5 | Day 6 | Average |
| | Group 1 | | | | | | | | | |
| JA-142 psg 200 | 545 | 0 | 0 | 2 | 0 | 0 | 0 | 0 | 0 | 0.25 |
| | 551 | 0 | 0 | 0 | 0 | 0 | 0 | 0 | 0 | 0 |
| | 561 | 0 | 0 | 0 | 0 | 0 | 0 | 0 | 0 | 0 |
| | 565 | 0 | 0 | 0 | 0 | 0 | 0 | 0 | 0 | 0 |
| | 806 | 0 | 0 | 0 | 0 | 0 | 0 | 0 | 0 | 0 |
| | Average | 0 | 0 | 0.4 | 0 | 0 | 0 | 0 | 0 | 0.05 |
| Saline | 550 | 0 | 0 | 0 | 0 | 0 | 0 | 0 | 0 | 0 |
| | 568 | 0 | 0 | 0 | 0 | 0 | 0 | 0 | 0 | 0 |
| | 801 | 0 | 0 | 0 | 0 | 0 | 0 | 0 | 0 | 0 |
| | Average | 0 | 0 | 0 | 0 | 0 | 0 | 0 | 0 | 0 |
| | Group 2 | | | | | | | | | |
| Backpassage 1 | 546 | 0 | 0 | 0 | 0 | 0 | 0 | 0 | 0 | 0 |
| | 553 | 0 | 0 | 0 | 0 | 0 | 0 | 0 | 0 | 0 |
| | 562 | 0 | 0 | 0 | 0 | 0 | 1 | 0 | 0 | 0.125 |
| | 572 | 0 | 0 | 0 | 0 | 0 | 0 | 0 | 0 | 0 |
| | 573 | 0 | 0 | 0 | 0 | 2 | 0 | 0 | 0 | 0.25 |
| | Average | 0 | 0 | 0 | 0 | 0.4 | 0.2 | 0 | 0 | 0.075 |
| Backpassage 1 | 556 | 0 | 0 | 0 | 0 | 0 | 0 | 0 | 0 | 0 |
| | 566 | 0 | 0 | 0 | 0 | 0 | 0 | 0 | 0 | 0 |
| | 802 | 0 | 0 | 0 | 0 | 0 | 0 | 0 | 0 | 0 |
| | Average | 0 | 0 | 0 | 0 | 0 | 0 | 0 | 0 | 0 |
| | Group 3 | | | | | | | | | |
| Backpassage 2 | 548 | 0 | 0 | 0 | 0 | 0 | 0 | 0 | 0 | 0 |
| | 567 | 0 | 0 | 0 | 0 | 0 | 0 | 0 | 0 | 0 |
| | 569 | 0 | 0 | 0 | 0 | 1 | 1 | 0 | 0 | 0.25 |
| | 574 | 0 | 0 | 0 | 0 | 0 | 0 | 0 | 0 | 0 |
| | 804 | 0 | 0 | 0 | 0 | 0 | 0 | 0 | 0 | 0 |
| | Average | 0 | 0 | 0 | 0 | 0.2 | 0.2 | 0 | 0 | 0.05 |
| Backpassage 2A | 547 | 0 | 0 | 0 | 0 | 0 | 0 | 0 | 0 | 0 |
| | 5564 | 0 | 0 | 0 | 0 | 0 | 0 | 0 | 0 | 0 |
| | 805 | 0 | 0 | 0 | 0 | 0 | 0 | 0 | 0 | 0 |
| | Average | 0 | 0 | 0 | 0 | 0 | 0 | 0 | 0 | 0 |
| | Group 4 | | | | | | | | | |
| Backpassage 3 | 549 | 0 | 0 | 0 | 0 | 0 | 0 | 0 | 0 | 0 |
| | 554 | 0 | 0 | 0 | 0 | 0 | 0 | 0 | 0 | 0 |
| | 563 | 0 | 0 | 0 | 0 | 0 | 0 | 0 | 0 | 0 |
| | 570 | 0 | 0 | 0 | 0 | 0 | 0 | 0 | 0 | 0 |
| | 803 | 0 | 0 | 0 | 0 | 0 | 0 | 0 | 0 | 0 |
| | Average | 0 | 0 | 0 | 0 | 0 | 0 | 0 | 0 | 0 |
| Backpassage 3A | 560 | 0 | 0 | 0 | 0 | 0 | 0 | 0 | 0 | 0 |
| | 571 | 0 | 0 | 0 | 0 | 0 | 0 | 0 | 0 | 0 |

TABLE 1-continued

| Treatment | Pig # | Day-1 | Day 0 | Day 1 | Day 2 | Day 3 | Day 4 | Day 5 | Day 6 | Average |
|---|---|---|---|---|---|---|---|---|---|---|
| | | Daily Clinical Scores | | | | | | | | |
| | 575 | 0 | 0 | 0 | 0 | 0 | 0 | 0 | 0 | 0 |
| | Average | 0 | 0 | 0 | 0 | 0 | 0 | 0 | 0 | 0 |
| | Group 5 | | | | | | | | | |
| Backpassage 4 | 1 | 0 | 2 | 0 | 0 | 2 | 0 | 2 | 2 | 1 |
| | 2 | 0 | 0 | 0 | 0 | 0 | 0 | 0 | 0 | 0 |
| | 3 | 2 | 0 | 2 | 2 | 2 | 2 | 2 | 2 | 1.75 |
| | 4 | 0 | 0 | 0 | 0 | 0 | 0 | 0 | 0 | 0 |
| | 5 | 0 | 0 | 0 | 0 | 0 | 0 | 0 | 0 | 0 |
| | Average | 0.4 | 0.4 | 0.4 | 0.4 | 0.8 | 0.4 | 0.8 | 0.8 | 0.55 |
| Backpassage 4A | 6 | 0 | 0 | 0 | 0 | 0 | 0 | 0 | 0 | 0 |
| | 7 | 0 | 0 | 2 | 2 | 2 | 2 | 2 | 2 | 1.5 |
| | 8 | 0 | 0 | 0 | 0 | 0 | 0 | 0 | 0 | 0 |
| | Average | 0 | 0.08 | 0.48 | 0.48 | 0.56 | 0.48 | 0.56 | 0.56 | 0.4 |
| | Group 6 | | | | | | | | | |
| Backpassage 5 | 10 | 0 | 0 | 0 | 0 | 2 | 0 | 0 | 2 | 0.5 |
| | 12 | 0 | 0 | 0 | 2 | 2 | 0 | 0 | 2 | 0.75 |
| | 14 | 0 | 0 | 0 | 0 | 0 | 0 | 0 | 0 | 0 |
| | 15 | 2 | 2 | 2 | 0 | 0 | 0 | 0 | 2 | 1 |
| | 16 | 2 | 2 | 2 | 0 | 0 | 1 | 1 | 2 | 1.25 |
| | Average | 0.8 | 0.8 | 0.8 | 0.4 | 0.8 | 0.2 | 0.2 | 1.6 | 0.7 |
| Backpassage 5A | 9 | 0 | 0 | 0 | 0 | 0 | 0 | 0 | 0 | 0 |
| | 11 | 2 | 2 | 0 | 0 | 0 | 0 | 0 | 0 | 0.5 |
| | 13 | 0 | 0 | 0 | 0 | 0 | 0 | 0 | 0 | 0 |
| | Average | 0.666667 | 0.56 | 0.16 | 0.08 | 0.16 | 0.04 | 0.04 | 0.32 | 0.253333 |

There were no significant differences between groups for rectal temperatures or daily weight gains. All lung scores were negative.

Serologically, ELISA S/P ratios and SN titers were negative throughout each group's trial period. Virus isolation was attempted on all serum samples and lung lavages. By day 6, 60–100% of the serum samples from the groups given JA-142, passage 200, and subsequent back passes were positive. The groups given saline were negative. In the first three passes, virus was recovered in the lung lavages from only 20–40% of the pigs, but by the last three passes, the virus was recovered from 50–80% of the pigs.

Based on this data, JA-142 passage 200 did not revert to virulence when passed through pigs six times.

EXAMPLE 3

Materials and Methods

This example demonstrated that the level of attenuation of safety of MSV, JA-142, passage 200 did not change significantly during six backpassages in the host animal. Evaluation of level of attenuation or safety was performed using the pregnant sow model and monitoring the effect on reproductive performance. This model is the most sensitive test system and does not rely upon subjective factors for virulence testing. This example consisted of four groups (A, B, C & D) having seven sows per group. Group A was inoculated intra-nasally with PRRS MSV, JA-142 passage 200. Group B was inoculated intra-nasally with JA-142, passage 200, Backpassage 6. Group C was inoculated intra-nasally with sterile diluent, to act as normal controls. Group D was inoculated intra-nasally with PRRSV JA-142, passage 4. The test articles (challenge with JA-142, passage 4) were given at about 93 days gestation. Body temperatures of the sows were monitored for the first seven days following vaccination. Blood samples were collected from the sows once a week and at time of farrowing. Blood samples were collected and weights were recorded from piglets at birth, 7, and 14 days of age. The health status of each animal was monitored daily for the duration of the study up to and following farrowing for 14 days. The farrowing performance was evaluated by observing the health status of the piglets born.

PRRS ELISA assays were performed following the exposures of the sows with the test article. PRRS ELISA assays were also performed on the piglet sera weekly following farrowing. Following exposure to the test article, attempts to isolate PRRSV from serum samples were performed on MA-104 cells. Rectal temperatures were measured periodically from 0 days post vaccination (DPV) to 7 DPV and the average temperature of each group was determined. Prior to and after inoculation, total white blood cell counts were determined as in Example 1. Clinical observations of the sows, as in Example 2, were made from −1 DPV through farrowing. Clinical observations of the piglets were made from farrowing until 14 days of age. Finally, at necropsy, the lungs of each piglet were scored for percent lung involvement.

Results

The ELISA results indicate that the animals used in this study were naive to PRRSV. Those animals that received virus inocula, groups A, B, and D, sero-converted at 14 days post treatment. Three sows of group B remained negative at 14 days post treatment. At the time of farrowing, the negative sows of group B tested positive for antibody to PRRSV.

The pigs' ELISA results indicated that the majority of the piglets born to sows of group A and group B were sampled after they had nursed. Those pigs that were negative at zero days post farrowing (0 DPF) tested positive at 7 DPF. All pigs born to sows of group C tested sero-negative throughout the study. Only a few pigs were tested from group D, since the majority were either stillborn or mummies. Half of those pigs that were tested were sero-positive. This indicated that the sero-negative pigs were sampled prior to nursing or they were not capable of nursing. All piglets born to sows of group D died before 7 DPF. Isolations of PRRSV from the sows of groups A and B were sporadic. Although the results of the ELISA test indicated that these sows were successfully inoculated with the viral test articles, many remained negative for virus isolation from serum.

The majority of pigs born to sows from groups A and B tested positive for virus isolation during the performance of the study. The litter born to one sow of group A never tested positive and the litter born to one sow of group B had only two of eight piglets test positive for virus isolation. No virus was recovered from the piglets born to sows from group C. Virus was recovered from the majority (71%) of piglets born from sows of group D.

Post treatment rectal temperatures were unremarkable. The groups that were treated with either MSV, backpassage 6 or sterile diluent experienced no measurements exceeding 101.7° F. Group D, treated with JA-142, passage 4, had four (out of seven) sows that experienced temperatures that exceeded 102° F. with one sow reaching 103.4° F. for one of the days. The weight gain performance of the piglets born to sows of groups A (treated with MSV) and B (treated with MSV, backpassage 6) was greater than that of the pigs born to the control sows of group C. The average weight gain for the 14 day observation period was 7.9 lbs. For group A, it was 7.7 lbs; for group B and group C it was 6.9 lbs. The difference in the weight gain was not related to the size of the litter remaining at 14 days. The average litter sizes at 14 days post farrowing (DPF) were 9 for group A, 7 for group B, and 10 for group C. No pig born to the sows of group D survived beyond 3 DPF.

The white blood cell (WBC) counts for the sows of groups A, B, and C remained relatively constant. The average percentages of the pre-challenge values were equal to or greater than 92% for the duration of the observation period. Three sows of group D experienced WBC counts that were lower than the expected normal range ($7-20\times10^6$/ml).

The post inoculation clinical scores were unremarkable for the sows of groups A and B. Several sows of group C were observed to experience clinical signs over a period of several days. The majority of the clinical symptoms observed were in the category of decreased appetite, respiratory symptoms, and depression. One sow of group C died on trial day 31 of chronic bacterial pneumonia. Six of the seven sows of group D were observed to have clinical signs, primarily of varying degrees in severity, of lost appetite, ranging from decreased to anorexic. Results of the clinical scoring for the sows are given in Table 2.

TABLE 2

Sow Clinical Scores

| Treatment | Sow# | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 0 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0 | 0 | 0 | 0 |
| | | 13 | 14 | 15 | 16 | 17 | 18 | 19 | 20 | 21 | 22 | 23 | 24 | 25 | 26 | 27 | 28 |
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 2 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 2 | 0 | 0 | 0 | 0 | 0 | 0 | 0 | 0 | 0 | 0 | 0 | 0 | 0 | 0 |
| | Avg. | 0 | 0.6 | 0 | 0 | 0 | 0 | 0 | 0 | 0 | 0 | 0 | 0 | 0 | 0 | 0 | 0 |
| | | 29 | 30 | 31 | 32 | 33 | 34 | 35 | 36 | 37 | 38 | 39 | 40 | 41 | 42 | 43 | 44 |
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 0 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0 | 0 | 0 | 0 |
| Treatment | Sow# | −3 | −2 | −1 | 0 | 1 | 2 | 3 | 4 | 5 | 6 | 7 | 8 | 9 | 10 | 11 | 12 |
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 0 | 0 | 0 | 0 | 0 | 1 | 1 | 1 | 1 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0.1 | 0.1 | 0.1 | 0.1 |

TABLE 2-continued

| | | Sow Clinical Scores | | | | | | | | | | | | | | | |
|---|---|---|---|---|---|---|---|---|---|---|---|---|---|---|---|---|---|
| | | 13 | 14 | 15 | 16 | 17 | 18 | 19 | 20 | 21 | 22 | 23 | 24 | 25 | 26 | 27 | 28 |
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 1 | 1 | 0 | 0 | 0 | 0 | 0 | 0 | 0 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0.1 | 0.1 | 0 | 0 | 0 | 0 | 0 | 0 | 0 |
| | | 29 | 30 | 31 | 32 | 33 | 34 | 35 | 36 | 37 | 38 | 39 | 40 | 41 | 42 | 43 | 44 |
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 0 | 0 | 0 | 2 | 2 | 2 | 2 | 2 | 2 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0.3 | 0.3 | 0.3 | 0.3 | 0.3 | 0.3 |
| Treatment | Sow# | −3 | −2 | −1 | 0 | 1 | 2 | 3 | 4 | 5 | 6 | 7 | 8 | 9 | 10 | 11 | 12 |
| Group C | 58 | 0 | 0 | 0 | 0 | 0 | 0 | 0 | 0 | 0 | 0 | 0 | 0 | 0 | 0 | 0 | 0 |
| Sterile | 113 | 0 | 0 | 0 | 0 | 0 | 0 | 0 | 0 | 0 | 0 | 1 | 3 | 3 | 5 | 3 | 3 |
| Diluent | 117 | 0 | 0 | 0 | 0 | 0 | 0 | 0 | 0 | 0 | 0 | 0 | 0 | 0 | 0 | 1 | 1 |
| | 144 | 0 | 0 | 0 | 0 | 0 | 0 | 0 | 0 | 0 | 0 | 0 | 0 | 0 | 0 | 0 | 0 |
| | 156 | 0 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0.2 | 0.5 | 0.5 | 0.8 | 0.7 | 0.7 |
| | | 13 | 14 | 15 | 16 | 17 | 18 | 19 | 20 | 21 | 22 | 23 | 24 | 25 | 26 | 27 | 28 |
| Group C | 58 | 0 | 0 | 0 | 0 | 0 | 0 | 0 | 0 | 0 | 0 | 0 | 0 | 0 | 0 | 0 | 0 |
| Sterile | 113 | 3 | 3 | 3 | 3 | 3 | 3 | 4 | 4 | 4 | 4 | 6 | 6 | 2 | 4 | 2 | 2 |
| Diluent | 117 | 0 | 0 | 0 | 0 | 0 | 0 | 1 | 5 | 5 | 5 | 5 | 5 | 2 | 4 | 1 | 1 |
| | 144 | 0 | 0 | 0 | 0 | 0 | 0 | 0 | 0 | 0 | 0 | 0 | 0 | 0 | 0 | 0 | 0 |
| | 156 | 2 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0.8 | 0.5 | 0.5 | 0.5 | 0.5 | 0.5 | 0.8 | 1.5 | 1.5 | 1.5 | 1.8 | 1.8 | 0.7 | 1.3 | 0.5 | 0.5 |
| | | 29 | 30 | 31 | 32 | 33 | 34 | 35 | 36 | 37 | 38 | 39 | 40 | 41 | 42 | 43 | 44 |
| Group C | 58 | 0 | 0 | 0 | 0 | 0 | 0 | 0 | 0 | 0 | 0 | 0 | 0 | 0 | 0 | 0 | 0 |
| Sterile | 113 | 2 | 2 | 30 | | | | | | | | | | | | | |
| Diluent | 117 | 2 | 2 | 0 | 0 | 0 | 0 | 0 | 0 | 0 | 0 | 0 | 0 | 0 | 0 | 0 | 0 |
| | 144 | 0 | 0 | 0 | 0 | 0 | 0 | 0 | 0 | 0 | 0 | 1 | 1 | 1 | 1 | 1 | 1 |
| | 156 | 0 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0.7 | 0.7 | 6 | 0 | 0 | 0 | 0 | 0 | 0 | 0 | 0.2 | 0.2 | 0.2 | 0.2 | 0.2 | 0.2 |
| Treatment | Sow# | −3 | −2 | −1 | 0 | 1 | 2 | 3 | 4 | 5 | 6 | 7 | 8 | 9 | 10 | 11 | 12 |
| Group D | 2 | 0 | 0 | 0 | 0 | 0 | 0 | 0 | 0 | 0 | 1 | 1 | 1 | 1 | 1 | 1 | 1 |
| JA-142 | 106 | 0 | 0 | 0 | 0 | 0 | 0 | 0 | 0 | 0 | 0 | 1 | 1 | 1 | 1 | 1 | 1 |
| Pass 4 | 159 | 0 | 0 | 0 | 0 | 0 | 0 | 0 | 0 | 0 | 3 | 1 | 1 | 1 | 1 | 1 | 1 |
| | 190 | 0 | 0 | 0 | 0 | 0 | 0 | 0 | 0 | 0 | 0 | 0 | 0 | 1 | 1 | 1 | 1 |
| | 206 | 0 | 0 | 0 | 0 | 0 | 0 | 0 | 0 | 0 | 0 | 1 | 1 | 0 | 0 | 0 | 0 |
| | 232 | 0 | 0 | 0 | 0 | 0 | 0 | 0 | 0 | 0 | 0 | 0 | 0 | 0 | 0 | 0 | 0 |
| | 234 | 0 | 0 | 0 | 0 | 0 | 0 | 0 | 0 | 0 | 0 | 0 | 0 | 0 | 1 | 1 | 1 |
| | Avg. | 0 | 0 | 0 | 0 | 0 | 0 | 0 | 0 | 0 | 0.6 | 0.6 | 0.6 | 0.6 | 0.7 | 0.7 | 0.7 |
| | | 13 | 14 | 15 | 16 | 17 | 18 | 19 | 20 | 21 | 22 | 23 | 24 | 25 | 26 | 27 | 28 |
| Group D | 2 | 1 | 1 | 3 | 3 | 1 | 0 | 0 | 0 | 0 | 0 | 0 | 0 | 0 | 0 | 0 | 0 |
| JA-142 | 106 | 0 | 0 | 0 | 0 | 0 | 0 | 0 | 0 | 0 | 0 | 0 | 0 | 0 | 0 | 0 | 0 |
| Pass 4 | 159 | 1 | 1 | 1 | 1 | 3 | 4 | 2 | 3 | 3 | 3 | 2 | 0 | 0 | 2 | 0 | 0 |
| | 190 | 1 | 2 | 0 | 0 | 0 | 0 | 0 | 0 | 0 | 0 | 0 | 0 | 0 | 0 | 0 | 0 |
| | 206 | 0 | 0 | 0 | 0 | 0 | 0 | 0 | 0 | 0 | 0 | 0 | 0 | 0 | 0 | 0 | 0 |
| | 232 | 0 | 0 | 0 | 0 | 0 | 0 | 0 | 0 | 0 | 0 | 0 | 0 | 0 | 0 | 0 | 0 |
| | 234 | 0 | 2 | 0 | 0 | 0 | 0 | 0 | 0 | 0 | 0 | 0 | 0 | 0 | 0 | 0 | 0 |
| | Avg. | 0.4 | 0.3 | 0.6 | 0.6 | 0.6 | 0.6 | 0.3 | 0.4 | 0.4 | 0.4 | 0.3 | 0 | 0 | 0.3 | 0 | 0 |

TABLE 2-continued

| Sow Clinical Scores | | | | | | | | | | | |
|---|---|---|---|---|---|---|---|---|---|---|---|
| | | 29 | 30 | 31 | 32 | 33 | 34 | 35 | 36 | 37 | 38 |
| Group D | 2 | 0 | 0 | 0 | 1 | 1 | 1 | 3 | 3 | 1 | 1 |
| JA-142 | 106 | 0 | 0 | 0 | 0 | 0 | 0 | 0 | 0 | 0 | 0 |
| Pass 4 | 159 | 0 | 0 | 0 | 0 | 0 | 0 | 0 | 0 | 0 | 0 |
| | 190 | 0 | 0 | 0 | 0 | 0 | 0 | 0 | 0 | 0 | 0 |
| | 206 | 0 | 0 | 0 | 0 | 0 | 0 | 0 | 0 | 0 | 0 |
| | 232 | 0 | 0 | 0 | 0 | 0 | 0 | 0 | 0 | 0 | 0 |
| | 234 | 0 | 0 | 0 | 0 | 0 | 0 | 0 | 0 | 0 | 0 |
| | Avg. | 0 | 0 | 0 | 0.1 | 0.1 | 0.1 | 0.4 | 0.4 | 0.1 | 0.1 |

Clinical observations of the piglets fell into two major categories, death and reduced appetite. There were no significant differences between groups A, B and C in the area of average deaths per litter (DPL). Group A had an average of 1.3 DPL, group B had an average of 2.4 DPL, group C had an average of 2.0 DPL, and no pigs from group D survived beyond three days post farrowing. Clinical scores for the piglets are given in Table 3.

TABLE 3

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| GroupA | 98 | 813 | 0 | 0 | 1 | 30 | | | | | | | | | | |
| JA-142 | | 814 | 0 | 0 | 0 | 0 | 0 | 0 | 0 | 0 | 0 | 0 | 0 | 0 | 0 | 0 |
| Pass 200 | | 815 | 0 | 0 | 0 | 0 | 0 | 0 | 0 | 0 | 0 | 0 | 0 | 0 | 0 | 0 |
| | | 816 | 0 | 0 | 0 | 0 | 0 | 0 | 0 | 0 | 0 | 0 | 0 | 0 | 0 | 0 |
| | | 817 | 1 | 0 | 1 | 0 | 0 | 0 | 0 | 0 | 0 | 0 | 0 | 0 | 0 | 0 |
| | | 818 | 0 | 0 | 0 | 0 | 0 | 0 | 0 | 0 | 0 | 0 | 0 | 0 | 0 | 0 |
| | | 819 | 0 | 0 | 0 | 0 | 0 | 0 | 0 | 0 | 0 | 0 | 0 | 0 | 0 | 0 |
| | | 820 | 0 | 0 | 0 | 0 | 0 | 0 | 0 | 0 | 0 | 0 | 0 | 0 | 0 | 0 |
| | | 821 | 1 | 0 | 0 | 0 | 0 | 0 | 0 | 0 | 0 | 0 | 0 | 0 | 0 | 0 |
| | | 822 | 1 | 30 | | | | | | | | | | | | |
| | | Avg. | 0.3 | 3 | 0.2 | 3.3 | 0 | 0 | 0 | 0 | 0 | 0 | 0 | 0 | 0 | 0 |
| | 133 | 720 | 30 | | | | | | | | | | | | | |
| | | 721 | 0 | 1 | 0 | 0 | 0 | 0 | 0 | 0 | 0 | 0 | 0 | 0 | 0 | 0 |
| | | 722 | 0 | 0 | 0 | 1 | 0 | 0 | 0 | 0 | 0 | 0 | 0 | 0 | 0 | 0 |
| | | 723 | 0 | 0 | 0 | 0 | 0 | 0 | 0 | 0 | 0 | 0 | 0 | 0 | 0 | 0 |
| | | 724 | 0 | 1 | 0 | 0 | 0 | 1 | 0 | 0 | 0 | 0 | 0 | 0 | 0 | 0 |
| | | 725 | 0 | 0 | 0 | 0 | 0 | 0 | 0 | 0 | 0 | 0 | 0 | 0 | 0 | 0 |
| | | 798 | 0 | 0 | 0 | 0 | 0 | 0 | 0 | 0 | 0 | 0 | 0 | 0 | 0 | 0 |
| | | 799 | 30 | | | | | | | | | | | | | |
| | | 800 | 0 | 0 | 0 | 0 | 0 | 0 | 0 | 0 | 0 | 0 | 0 | 0 | 0 | 0 |
| | | 807 | 0 | 0 | 0 | 0 | 0 | 0 | 0 | 0 | 0 | 0 | 0 | 1 | 0 | 0 |
| | | 809 | 0 | 0 | 0 | 0 | 0 | 0 | 0 | 0 | 0 | 0 | 0 | 0 | 0 | 0 |
| | | 810 | 0 | 0 | 0 | 0 | 0 | 0 | 0 | 0 | 0 | 0 | 0 | 0 | 0 | 0 |
| | | 812 | 0 | 0 | 0 | 0 | 0 | 0 | 0 | 0 | 0 | 0 | 0 | 0 | 0 | 0 |
| | | Avg. | 4.6 | 0.2 | 0 | 0.1 | 0 | 0.1 | 0 | 0 | 0 | 0 | 0 | 0.1 | 0 | 0 |
| | 147 | 823 | 0 | 0 | 0 | 0 | 0 | 0 | 0 | 0 | 0 | 0 | 0 | 0 | 0 | 0 |
| | | 824 | 0 | 0 | 0 | 0 | 0 | 0 | 0 | 3 | 1 | 1 | 1 | 1 | 1 | 1 |
| | | 825 | 0 | 0 | 0 | 0 | 0 | 0 | 0 | 0 | 0 | 0 | 0 | 0 | 0 | 0 |
| | | 845 | 0 | 0 | 0 | 0 | 0 | 0 | 0 | 0 | 0 | 0 | 0 | 0 | 0 | 0 |
| | | 846 | 0 | 0 | 0 | 0 | 0 | 0 | 0 | 0 | 0 | 0 | 0 | 0 | 0 | 0 |
| | | 847 | 0 | 0 | 0 | 0 | 0 | 0 | 0 | 0 | 0 | 0 | 0 | 0 | 0 | 0 |
| | | 848 | 0 | 0 | 0 | 0 | 0 | 0 | 1 | 0 | 0 | 0 | 0 | 0 | 0 | 0 |
| | | 849 | 0 | 0 | 0 | 0 | 0 | 0 | 0 | 0 | 0 | 0 | 0 | 0 | 0 | 2 |
| | | 850 | 30 | | | | | | | | | | | | | |
| | | 976 | 0 | 0 | 0 | 0 | 0 | 0 | 0 | 0 | 0 | 0 | 0 | 0 | 0 | 0 |
| | | 977 | 0 | 0 | 0 | 0 | 1 | 1 | 3 | 30 | | | | | | |
| | | 978 | 30 | | | | | | | | | | | | | |
| | | Avg. | 5 | 0 | 0 | 0 | 0.1 | 0.1 | 0.4 | 3.3 | 0.1 | 0.1 | 0.1 | 0.1 | 0.1 | 0.3 |
| | 178 | 486 | 30 | | | | | | | | | | | | | |
| | | 487 | 0 | 0 | 0 | 0 | 0 | 0 | 0 | 0 | 0 | 0 | 0 | 1 | 0 | 0 |
| | | 488 | 0 | 0 | 0 | 0 | 0 | 0 | 0 | 0 | 0 | 0 | 0 | 0 | 0 | 0 |
| | | 489 | 0 | 0 | 0 | 0 | 0 | 0 | 0 | 0 | 0 | 0 | 0 | 0 | 0 | 0 |
| | | 490 | 0 | 0 | 0 | 0 | 0 | 0 | 0 | 0 | 0 | 0 | 0 | 0 | 0 | 0 |
| | | 491 | 0 | 0 | 0 | 0 | 0 | 0 | 0 | 0 | 0 | 0 | 0 | 0 | 0 | 0 |
| | | 492 | 0 | 0 | 0 | 0 | 0 | 0 | 0 | 0 | 0 | 0 | 0 | 0 | 0 | 0 |
| | | 493 | 0 | 0 | 0 | 0 | 0 | 0 | 0 | 0 | 0 | 0 | 0 | 0 | 0 | 0 |
| | | 494 | 0 | 1 | 0 | 0 | 0 | 0 | 0 | 0 | 0 | 0 | 0 | 0 | 0 | 0 |
| | | Avg. | 3.3 | 0.1 | 0 | 0 | 0 | 0 | 0 | 0 | 0 | 0 | 0 | 0.1 | 0 | 0 |
| Group A | 215 | 495 | 0 | 0 | 0 | 0 | 0 | 0 | 0 | 0 | 0 | 0 | 0 | 0 | 0 | 0 |
| JA-142 | | 496 | 0 | 0 | 0 | 0 | 0 | 0 | 0 | 0 | 0 | 0 | 0 | 0 | 0 | 0 |
| Pass 200 | | 497 | 0 | 0 | 0 | 0 | 0 | 0 | 0 | 0 | 0 | 0 | 0 | 0 | 0 | 0 |
| | | 498 | 0 | 0 | 0 | 0 | 0 | 0 | 0 | 0 | 0 | 0 | 0 | 0 | 0 | 0 |
| | | 499 | 0 | 0 | 0 | 0 | 0 | 0 | 0 | 0 | 0 | 0 | 0 | 0 | 0 | 0 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 500 | 0 | 0 | 0 | 0 | 0 | 0 | 0 | 0 | 0 | 0 | 0 | 0 | 0 | 0 |
| | | 808 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 233 | 476 | 0 | 0 | 0 | 0 | 0 | 0 | 0 | 0 | 0 | 0 | 0 | 0 | 0 | 0 |
| | | 477 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 480 | 0 | 0 | 0 | 0 | 0 | 0 | 0 | 0 | 0 | 0 | 0 | 0 | 0 | 0 |
| | | 481 | 0 | 0 | 0 | 0 | 0 | 0 | 0 | 0 | 0 | 0 | 0 | 0 | 0 | 0 |
| | | 482 | 0 | 0 | 0 | 0 | 0 | 0 | 0 | 0 | 0 | 0 | 0 | 0 | 0 | 0 |
| | | 483 | 0 | 0 | 0 | 0 | 0 | 0 | 0 | 0 | 0 | 0 | 0 | 0 | 0 | 0 |
| | | 484 | 0 | 0 | 0 | 0 | 0 | 0 | 0 | 0 | 0 | 0 | 0 | 0 | 0 | 0 |
| | | 485 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 243 | 707 | 0 | 0 | 0 | 0 | 0 | 0 | 0 | 0 | 0 | 0 | 0 | 0 | 0 | 0 |
| | | 708 | 0 | 0 | 0 | 0 | 0 | 0 | 0 | 0 | 0 | 0 | 0 | 0 | 0 | 0 |
| | | 709 | 0 | 0 | 0 | 0 | 0 | 0 | 0 | 0 | 0 | 0 | 0 | 0 | 0 | 0 |
| | | 710 | 0 | 0 | 0 | 0 | 0 | 0 | 0 | 0 | 0 | 0 | 0 | 0 | 0 | 0 |
| | | 711 | 0 | 0 | 0 | 0 | 0 | 0 | 0 | 0 | 0 | 0 | 0 | 0 | 0 | 0 |
| | | 712 | 0 | 0 | 0 | 0 | 0 | 0 | 0 | 0 | 0 | 0 | 0 | 0 | 0 | 0 |
| | | 713 | 0 | 0 | 0 | 0 | 0 | 0 | 0 | 0 | 0 | 1 | 30 | | | |
| | | 714 | 0 | 0 | 0 | 0 | 0 | 0 | 0 | 0 | 0 | 0 | 0 | 0 | 0 | 0 |
| | | 715 | 0 | 0 | 0 | 0 | 0 | 0 | 0 | 0 | 0 | 0 | 0 | 0 | 0 | 0 |
| | | 716 | 0 | 0 | 0 | 0 | 0 | 0 | 0 | 0 | 0 | 0 | 0 | 0 | 0 | 0 |
| | | 717 | 0 | 0 | 0 | 0 | 0 | 0 | 0 | 0 | 0 | 0 | 0 | 1 | 0 | 0 |
| | | 718 | 0 | 0 | 0 | 0 | 0 | 0 | 0 | 0 | 0 | 0 | 0 | 1 | 0 | 0 |
| | | 719 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0.1 | 2.3 | 0.2 | 0 | 0 |
| Group B | | | | | | | | | | | | | | | | |
| Backpassage 6 | 49 | 430 | 0 | 0 | 0 | 0 | 0 | 0 | 0 | 0 | 0 | 0 | 0 | 0 | 0 | 0 |
| | | 431 | 0 | 0 | 0 | 0 | 0 | 0 | 0 | 0 | 0 | 0 | 0 | 0 | 0 | 0 |
| | | 432 | 0 | 0 | 0 | 0 | 0 | 0 | 0 | 0 | 0 | 0 | 0 | 0 | 0 | 0 |
| | | 433 | 0 | 0 | 0 | 0 | 0 | 0 | 0 | 0 | 0 | 0 | 0 | 0 | 0 | 0 |
| | | 434 | 0 | 0 | 0 | 0 | 0 | 0 | 0 | 0 | 0 | 0 | 0 | 0 | 0 | 0 |
| | | 435 | 0 | 0 | 0 | 0 | 0 | 0 | 0 | 0 | 0 | 0 | 0 | 0 | 0 | 0 |
| | | 436 | 0 | 0 | 0 | 0 | 0 | 0 | 0 | 0 | 0 | 0 | 0 | 0 | 0 | 0 |
| | | 437 | 0 | 0 | 0 | 0 | 0 | 0 | 0 | 0 | 0 | 0 | 0 | 0 | 0 | 0 |
| | | 438 | 30 | 0 | 0 | 0 | 0 | 0 | 0 | 0 | 0 | 0 | 0 | 0 | 0 | 0 |
| | | Avg. | 3.3 | 0 | 0 | 0 | 0 | 0 | 0 | 0 | 0 | 0 | 0 | 0 | 0 | 0 |
| | 100 | 459 | 0 | 0 | 0 | 0 | 0 | 0 | 0 | 0 | 0 | 0 | 0 | 0 | 0 | 0 |
| | | 460 | 0 | 0 | 0 | 0 | 0 | 0 | 0 | 0 | 0 | 0 | 0 | 0 | 0 | 0 |
| | | 461 | 0 | 0 | 0 | 0 | 0 | 0 | 1 | 1 | 1 | 0 | 0 | 0 | 0 | 0 |
| | | 462 | 0 | 0 | 0 | 0 | 1 | 1 | 1 | 1 | 1 | 1 | 1 | 1 | 1 | 1 |
| | | 463 | 0 | 0 | 0 | 0 | 0 | 0 | 0 | 0 | 0 | 0 | 0 | 0 | 0 | 0 |
| | | 464 | 0 | 0 | 1 | 1 | 1 | 1 | 30 | | | | | | | |
| | | 465 | 0 | 30 | | | | | | | | | | | | |
| | | Avg. | 0 | 4.3 | 0.2 | 0.2 | 0.3 | 0.3 | 5.3 | 0.4 | 0.4 | 0.2 | 0.2 | 0.2 | 0.2 | 0.2 |
| | 135 | 439 | 0 | 0 | 0 | 0 | 0 | 0 | 0 | 30 | | | | | | |
| | | 440 | 0 | 0 | 0 | 0 | 0 | 0 | 0 | 0 | 0 | 0 | 0 | 0 | 0 | 0 |
| | | 441 | 0 | 0 | 0 | 0 | 0 | 0 | 0 | 0 | 0 | 0 | 0 | 0 | 0 | 0 |
| | | 442 | 0 | 0 | 0 | 1 | 1 | 1 | 1 | 1 | 1 | 1 | 3 | 3 | 3 | 30 |
| | | 443 | 0 | 0 | 0 | 0 | 0 | 0 | 0 | 0 | 0 | 0 | 0 | 0 | 0 | 0 |
| | | 444 | 0 | 0 | 0 | 0 | 0 | 0 | 1 | 1 | 0 | 0 | 0 | 0 | 0 | 0 |
| | | 445 | 0 | 0 | 0 | 0 | 0 | 0 | 0 | 0 | 0 | 0 | 0 | 0 | 0 | 0 |
| | | 446 | 0 | 0 | 0 | 0 | 0 | 0 | 0 | 0 | 0 | 0 | 0 | 0 | 0 | 0 |
| | | 447 | 0 | 0 | 0 | 0 | 0 | 0 | 0 | 0 | 0 | 0 | 0 | 0 | 0 | 0 |
| | | Avg. | 0 | 0 | 0 | 0.1 | 0.1 | 0.1 | 0.2 | 3.6 | 0.1 | 0.1 | 0.4 | 0.4 | 0.4 | 3.8 |
| | 149 | 231 | 0 | 0 | 0 | 0 | 0 | 0 | 0 | 0 | 0 | 0 | 0 | 0 | 0 | 0 |
| | | 232 | 0 | 0 | 0 | 0 | 0 | 0 | 0 | 0 | 0 | 0 | 0 | 0 | 0 | 0 |
| | | 233 | 0 | 0 | 0 | 0 | 0 | 0 | 30 | | | | | | | |
| | | 234 | 0 | 0 | 0 | 0 | 0 | 0 | 3 | 1 | 1 | 3 | 1 | 1 | 1 | 1 |
| | | 235 | 0 | 0 | 0 | 0 | 0 | 0 | 3 | 2 | 3 | 3 | 0 | 0 | 0 | 0 |
| | | 236 | 0 | 0 | 0 | 0 | 0 | 0 | 0 | 0 | 0 | 0 | 0 | 0 | 0 | 0 |
| | | 237 | 0 | 0 | 0 | 0 | 0 | 0 | 1 | 1 | 1 | 1 | 1 | 1 | 1 | 1 |
| | | 238 | 0 | 0 | 0 | 0 | 0 | 2 | 0 | 0 | 0 | 0 | 0 | 0 | 0 | 0 |
| | | 239 | 0 | 0 | 30 | | | | | | | | | | | |
| | | 240 | 30 | | | | | | | | | | | | | |
| | | 241 | 3 | 30 | | | | | | | | | | | | |
| | | 242 | 0 | 0 | 0 | 0 | 0 | 2 | 3 | 3 | 30 | | | | | |
| | | Avg. | 2.8 | 2.7 | 3 | 0 | 0 | 0.4 | 4.4 | 0.9 | 4.4 | 1 | 0.3 | 0.3 | 0.3 | 0.3 |
| Group B Backpassage 6 | 209 | 448 | 0 | 0 | 0 | 0 | 0 | 0 | 0 | 0 | 0 | 0 | 0 | 0 | 0 | 0 |
| | | 449 | 0 | 0 | 0 | 0 | 0 | 0 | 0 | 0 | 0 | 0 | 0 | 0 | 0 | 0 |
| | | 450 | 0 | 0 | 0 | 0 | 0 | 0 | 0 | 0 | 0 | 0 | 0 | 0 | 0 | 0 |
| | | 451 | 0 | 0 | 0 | 0 | 0 | 0 | 0 | 0 | 1 | 1 | 1 | 1 | 1 | 1 |
| | | 452 | 0 | 0 | 0 | 0 | 0 | 0 | 0 | 0 | 0 | 0 | 0 | 0 | 0 | 0 |
| | | 453 | 0 | 0 | 0 | 0 | 0 | 0 | 0 | 0 | 0 | 0 | 0 | 0 | 0 | 0 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 454 | 0 | 0 | 0 | 0 | 0 | 0 | 0 | 0 | 1 | 1 | 1 | 1 | 1 | 1 |
| | | 455 | 0 | 0 | 0 | 0 | 0 | 0 | 0 | 0 | 0 | 1 | 1 | 1 | 1 | 1 |
| | | 456 | 30 | | | | | | | | | | | | | |
| | | 457 | 0 | 0 | 0 | 0 | 0 | 0 | 0 | 0 | 2 | 1 | 1 | 1 | 1 | 1 |
| | | 458 | 30 | | | | | | | | | | | | | |
| | | Avg. | 5.5 | 0 | 0 | 0 | 0 | 0 | 0 | 0 | 0.4 | 0.4 | 0.4 | 0.4 | 0.4 | 0.4 |
| | 212 | 243 | 0 | 0 | 0 | 0 | 0 | 0 | 0 | 0 | 0 | 0 | 0 | 0 | 0 | 0 |
| | | 244 | 0 | 0 | 0 | 0 | 0 | 0 | 0 | 0 | 0 | 0 | 0 | 0 | 0 | 0 |
| | | 245 | 0 | 0 | 0 | 0 | 3 | 1 | 30 | | | | | | | |
| | | 246 | 0 | 0 | 0 | 0 | 0 | 0 | 0 | 0 | 0 | 0 | 0 | 0 | 0 | 0 |
| | | 247 | 0 | 0 | 0 | 0 | 0 | 2 | 2 | 0 | 0 | 0 | 0 | 0 | 0 | 0 |
| | | 248 | 0 | 0 | 0 | 0 | 2 | 0 | 0 | 0 | 0 | 0 | 0 | 0 | 0 | 0 |
| | | 249 | 0 | 0 | 0 | 0 | 0 | 0 | 2 | 2 | 0 | 0 | 2 | 0 | 0 | 0 |
| | | 250 | 0 | 0 | 0 | 3 | 30 | | | | | | | | | |
| | | 426 | 0 | 0 | 0 | 0 | 0 | 0 | 0 | 0 | 0 | 0 | 0 | 0 | 0 | 0 |
| | | 427 | 0 | 0 | 0 | 1 | 3 | 1 | 1 | 30 | | | | | | |
| | | 428 | 0 | 0 | 0 | 1 | 3 | 3 | 30 | | | | | | | |
| | | 429 | 0 | 0 | 0 | 0 | 2 | 3 | 3 | 3 | 3 | 3 | 3 | 1 | 30 | |
| | | Avg. | 0 | 0 | 0 | 0.4 | 3.6 | 0.9 | 6.2 | 3.9 | 0.4 | 0.4 | 0.6 | 0.1 | 3.8 | 0 |
| | 226 | Not Preg. | | | | | | | | | | | | | | |
| Group C Sterile Diluent | 58 | 24 | 0 | 0 | 0 | 0 | 0 | 0 | 0 | 0 | 0 | 0 | 0 | 0 | 0 | 0 |
| | | 25 | 0 | 0 | 0 | 0 | 0 | 0 | 0 | 0 | 0 | 0 | 0 | 0 | 0 | 0 |
| | | 46 | 0 | 0 | 0 | 0 | 0 | 0 | 0 | 0 | 0 | 0 | 0 | 0 | 0 | 0 |
| | | 47 | 0 | 0 | 0 | 0 | 0 | 0 | 0 | 0 | 0 | 0 | 0 | 0 | 0 | 0 |
| | | 48 | 0 | 0 | 0 | 0 | 0 | 0 | 0 | 0 | 0 | 0 | 0 | 0 | 0 | 0 |
| | | 49 | 0 | 0 | 0 | 0 | 0 | 0 | 0 | 0 | 0 | 0 | 0 | 0 | 0 | 0 |
| | | 50 | 0 | 0 | 0 | 0 | 0 | 0 | 0 | 0 | 0 | 0 | 0 | 0 | 0 | 0 |
| | | 51 | 0 | 0 | 0 | 2 | 2 | 1 | 1 | 1 | 30 | | | | | |
| | | Avg. | 0 | 0 | 0 | 0.3 | 0.3 | 0.1 | 0.1 | 0.1 | 3.8 | 0 | 0 | 0 | 0 | 0 |
| | 113 | 17 | 30 | | | | | | | | | | | | | |
| | | 18 | 30 | | | | | | | | | | | | | |
| | | 19 | 30 | | | | | | | | | | | | | |
| | | 20 | 30 | | | | | | | | | | | | | |
| | | 21 | 0 | 30 | | | | | | | | | | | | |
| | | 22 | 30 | | | | | | | | | | | | | |
| | | 23 | 30 | | | | | | | | | | | | | |
| | | Avg. | 25.7 | 30 | | | | | | | | | | | | |
| | 117 | 52 | 1 | 0 | 0 | 0 | 0 | 0 | 0 | 0 | 0 | 0 | 0 | 0 | 0 | 0 |
| | | 53 | 0 | 0 | 0 | 0 | 0 | 0 | 0 | 0 | 0 | 0 | 0 | 0 | 0 | 0 |
| | | 54 | 0 | 0 | 0 | 0 | 0 | 0 | 0 | 0 | 0 | 0 | 0 | 0 | 0 | 0 |
| | | 55 | 0 | 0 | 0 | 0 | 0 | 0 | 0 | 0 | 0 | 0 | 0 | 0 | 0 | 0 |
| | | 56 | 1 | 0 | 0 | 0 | 30 | | | | | | | | | |
| | | 57 | 1 | 0 | 0 | 0 | 0 | 0 | 0 | 0 | 0 | 0 | 0 | 0 | 0 | 0 |
| | | 58 | 0 | 0 | 0 | 0 | 0 | 0 | 0 | 0 | 0 | 0 | 0 | 0 | 0 | 0 |
| | | 59 | 0 | 0 | 0 | 0 | 0 | 0 | 0 | 0 | 0 | 0 | 0 | 0 | 0 | 0 |
| | | 60 | 0 | 0 | 0 | 0 | 0 | 0 | 0 | 0 | 0 | 0 | 0 | 1 | 0 | 0 |
| | | 61 | 1 | 0 | 0 | 0 | 0 | 0 | 0 | 0 | 1 | 1 | 1 | 0 | 0 | 0 |
| | | 62 | 1 | 0 | 0 | 0 | 0 | 0 | 0 | 0 | 0 | 0 | 0 | 0 | 0 | 0 |
| | | Avg. | 0.5 | 0 | 0 | 0 | 2.7 | 0 | 0 | 0 | 0.1 | 0.1 | 0.1 | 0.1 | 0 | 0 |
| | 144 | 146 | 0 | 0 | 0 | 0 | 0 | 0 | 0 | 0 | 0 | 0 | 0 | 0 | 0 | 0 |
| | | 147 | 0 | 0 | 0 | 0 | 0 | 0 | 0 | 0 | 0 | 0 | 0 | 0 | 0 | 0 |
| | | 148 | 0 | 0 | 0 | 0 | 0 | 0 | 0 | 0 | 0 | 0 | 0 | 0 | 0 | 0 |
| | | 149 | 0 | 0 | 0 | 0 | 0 | 0 | 0 | 0 | 0 | 0 | 0 | 0 | 0 | 0 |
| | | 150 | 0 | 0 | 0 | 0 | 0 | 0 | 0 | 0 | 1 | 0 | 1 | 1 | 1 | 0 |
| | | 221 | 0 | 0 | 0 | 0 | 0 | 2 | 2 | 0 | 0 | 0 | 0 | 0 | 0 | 0 |
| | | 222 | 0 | 0 | 0 | 0 | 0 | 2 | 2 | 1 | 1 | 1 | 1 | 1 | 0 | 1 |
| | | 223 | 0 | 0 | 0 | 0 | 0 | 0 | 0 | 0 | 0 | 0 | 0 | 0 | 0 | 0 |
| | | 224 | 0 | 0 | 0 | 0 | 0 | 0 | 0 | 0 | 0 | 0 | 0 | 0 | 0 | 0 |
| | | 225 | 0 | 0 | 0 | 0 | 0 | 0 | 0 | 0 | 0 | 0 | 0 | 0 | 0 | 0 |
| | | 970 | 0 | 0 | 0 | 0 | 0 | 0 | 0 | 0 | 0 | 0 | 0 | 0 | 0 | 0 |
| | | 971 | 0 | 0 | 0 | 0 | 0 | 0 | 0 | 0 | 0 | 0 | 0 | 0 | 0 | 0 |
| | | Avg. | 0 | 0 | 0 | 0 | 0 | 0.3 | 0.3 | 0.1 | 0.2 | 0.1 | 0.2 | 0.2 | 0.1 | 0.1 |
| Group C Sterile Diluent | 156 | 63 | 0 | 0 | 0 | 0 | 0 | 0 | 0 | 0 | 0 | 0 | 0 | 0 | 0 | 0 |
| | | 64 | 0 | 0 | 1 | 0 | 30 | | | | | | | | | |
| | | 65 | 0 | 0 | 0 | 0 | 0 | 0 | 0 | 1 | 1 | 1 | 1 | 1 | 0 | 0 |
| | | 66 | 0 | 0 | 0 | 0 | 1 | 0 | 0 | 0 | 0 | 0 | 0 | 0 | 0 | 0 |
| | | 67 | 0 | 0 | 0 | 0 | 1 | 0 | 1 | 1 | 30 | | | | | |
| | | 68 | 0 | 0 | 0 | 0 | 0 | 0 | 0 | 0 | 0 | 0 | 0 | 0 | 0 | 0 |
| | | 69 | 0 | 0 | 0 | 0 | 0 | 0 | 0 | 1 | 0 | 0 | 0 | 0 | 0 | 0 |
| | | 70 | 0 | 0 | 0 | 0 | 0 | 0 | 0 | 0 | 0 | 0 | 0 | 0 | 0 | 0 |
| | | 71 | 0 | 0 | 0 | 0 | 0 | 2 | 2 | 0 | 0 | 0 | 0 | 0 | 1 | 0 |
| | | 72 | 0 | 0 | 0 | 0 | 0 | 0 | 0 | 0 | 0 | 0 | 0 | 0 | 0 | 0 |
| | | 73 | 0 | 0 | 0 | 0 | 0 | 0 | 0 | 0 | 0 | 0 | 0 | 0 | 0 | 0 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 74 | 0 | 0 | 0 | 0 | 1 | 0 | 0 | 0 | 0 | 0 | 0 | 0 | 0 | 0 |
| | | 75 | 0 | 0 | 0 | 0 | 0 | 0 | 0 | 0 | 0 | 0 | 0 | 0 | 0 | 0 |
| | | Avg. | 0 | 0 | 0.1 | 0 | 2.5 | 0.2 | 0.3 | 0.3 | 2.6 | 0.1 | 0.1 | 0.1 | 0.1 | 0 |
| | 166 | 76 | 0 | 0 | 0 | 0 | 0 | 0 | 0 | 0 | 0 | 0 | 0 | 0 | 0 | 0 |
| | | 77 | 0 | 0 | 0 | 0 | 0 | 0 | 0 | 0 | 0 | 0 | 0 | 0 | 0 | 0 |
| | | 78 | 0 | 0 | 0 | 0 | 0 | 0 | 0 | 0 | 0 | 0 | 0 | 0 | 0 | 0 |
| | | 79 | 0 | 0 | 0 | 0 | 0 | 0 | 0 | 0 | 0 | 0 | 0 | 0 | 0 | 0 |
| | | 80 | 0 | 0 | 0 | 0 | 0 | 0 | 0 | 0 | 0 | 0 | 0 | 0 | 0 | 0 |
| | | 81 | 1 | 0 | 0 | 0 | 0 | 0 | 0 | 0 | 0 | 0 | 0 | 0 | 0 | 0 |
| | | 141 | 0 | 0 | 0 | 0 | 0 | 0 | 0 | 0 | 0 | 0 | 0 | 0 | 0 | 0 |
| | | 142 | 0 | 0 | 0 | 0 | 0 | 0 | 0 | 0 | 0 | 0 | 0 | 0 | 0 | 0 |
| | | 143 | 0 | 0 | 0 | 0 | 0 | 0 | 0 | 0 | 0 | 0 | 0 | 0 | 0 | 0 |
| | | 144 | 0 | 0 | 0 | 0 | 0 | 0 | 0 | 0 | 0 | 0 | 0 | 0 | 0 | 0 |
| | | 145 | 1 | 30 | | | | | | | | | | | | |
| | | Avg. | 0.2 | 2.7 | 0 | 0 | 0 | 0 | 0 | 0 | 0 | 0 | 0 | 0 | 0 | 0 |
| Group D | | | | | | | | | | | | | | | | |
| JA-142 | 2 | 891 | 1 | 3 | 30 | | | | | | | | | | | |
| Passage 4 | | 892 | 1 | 30 | | | | | | | | | | | | |
| | | Avg. | 1 | 16.5 | 30 | | | | | | | | | | | |
| | 106 | Aborted | NA | | | | | | | | | | | | | |
| | 159 | 883 | 30 | | | | | | | | | | | | | |
| | | 884 | 30 | | | | | | | | | | | | | |
| | | Avg. | 30 | | | | | | | | | | | | | |
| | 190 | Aborted | NA | | | | | | | | | | | | | |
| | 206 | 890 | 30 | | | | | | | | | | | | | |
| | | Avg. | 30 | | | | | | | | | | | | | |
| | 232 | 888 | 30 | | | | | | | | | | | | | |
| | | 889 | 30 | | | | | | | | | | | | | |
| | | Avg. | 30 | | | | | | | | | | | | | |
| | 234 | Aborted | NA | | | | | | | | | | | | | |

The farrowing performance results provided the most dramatic differences and similarities between the various treatment groups. Since the treatments would not have an effect on the size of the litters, the most appropriate way to compare the farrowing results would be by using percentage values. Group A had an average percentage of live/born of 85% (SD+/−9.6). Group B had an average percentage of live/born of 89% (SD+/−11.6). The control group (group C) had an average percentage of live/born of 83.4% (SD+/−7.9). The average percentages for stillborns for groups A, B and C were 8.8 (SD+/−9.66), 6.6 (SD+/−9.7), and 14 (SD+/−11.39), respectively. The average percentages of mummies born to sows of groups A, B, and C were 6.1 (SD+/−6.01), 3.9 (SD+/−4.45), and 2.6 (SD+/−4.01), respectively. The average percentages of live/born, stillborn and mummies born to the sows of group D were 8.7 (SD+/−8.92), 10.7 (SD+/−11.39), and 81.9 (SD+/−17.18), respectively.

The results of this example demonstrated the stability of the MSV, JA-142, passage 200 after being passed in the host animal six times. There were no significant differences between the group of sows treated with the MSV (group A) and those sows that were exposed to the Backpassage 6 virus (group B) in the categories of farrowing performance, leukopenia, rectal temperatures, and the clinical observations of either the sows or the piglets. In addition, the results in these same categories for the groups A and B were comparable to those achieved by group C that had been treated with sterile diluent. Finally, the performance of the sows that had been exposed to the virulent parent virus of MSV, JA-142, passage 4, clearly illustrated the level of attenuation of the MSV and the lack of reversion to virulence by the Backpassage 6, JA-142 virus.

EXAMPLE 4

Materials and Methods

This example evaluated the safety and level of attenuation of administering a 10× concentration of MSV, JA-142, passage 201. The study was performed on the pregnant sow model and monitored the effect of this dosage on reproductive performance. The study consisted of three groups, A, C, and D. Group A was inoculated intra-nasally with PRRS MSV, JA-142, passage 200. Group C was inoculated intra-nasally with sterile diluent, to act as a normal control group. Group D was inoculated intra-nasally with 10× JA-142, passage 201. All inoculations were given at about 93 days gestation. Body temperatures of the sows were monitored for the first seven days following inoculation (vaccination). Blood samples were collected from the sows once a week and at time of farrowing. Prior to and following inoculation, total white blood cell counts were determined as in Example 2. The health status of each animal was monitored daily for the duration of the study up to and following farrowing for 14 days. Clinical observations of the sows were made from −1 DPV through farrowing. The farrowing performance was evaluated by observing the health status of the piglets born. PRRSV ELISA assays were preformed following the exposures of the sows with the test article. Attempts to isolate PRRSV from serum samples were performed on MA-104 cells following exposure to the test article. Clinical observations of the piglets were made from farrowing until 14 days of age. Blood samples were collected from the piglets at birth, 7 and 14 days of age. PRRSV ELISA assays were performed on the piglet sera weekly following farrowing. Piglets were also weighed at birth, day 7 post farrowing, and at necropsy. At necropsy, the lungs of each piglet were scored for percent lung involvement.

Results and Discussion

There were no significant differences between groups given a 10× dose of MSV, JA-142, passage 201, groups given a regular dose of MSV, JA-142, passage 200, and groups given sterile diluent. Therefore, based on the safety and attenuation of MSV, JA-142, passage 200 and the lack of any significant difference in the results comparing these groups, a 10× dose of MSV, JA-142, passage 201 was shown to be safe, attenuated and effective in inducing antibodies against PRRSV.

EXAMPLE 5

Materials and Methods

This example demonstrated that a minimal vaccine dose of PRRSV, JA-142, passage 205, representing MSV+5, is efficacious in an experimental respiratory challenge model in feeder pigs. Pigs were divided into three groups. Group 1 was inoculated intramuscularly with PRRS MSV, JA-142, passage 205 at a titer of 2.0 logs/dose. Group 2 was inoculated intramuscularly with sterile diluent. Group 3 acted as normal controls. Pigs from groups 1 and 2 were challenged with a PRRSV isolate with an RFLP pattern of 144 on day 28 post vaccination. Body temperatures of the pigs were monitored for the first seven days following vaccination and daily following challenge. Each animal was weighed at vaccination, challenge, weekly throughout the study, and necropsy. Blood samples were collected weekly following vaccination and every two days following challenge. The health status of each animal was monitored daily for the duration of the study. At necropsy, each animal was sacrificed and the lungs were scored for percent lung involvement as in Example 2. PRRSV ELISA assays were performed following the exposures of the pigs with the test articles and challenge. Following exposure to the test articles, attempts to isolate PRRSV from serum samples were performed on MA-104 cells. Virus isolation and ELISA results were analyzed using a Chi-square analysis which tests whether the percentage of positive animals is the same in each group. White blood cell counts were performed as in Example 2.

Results and Discussion

Pigs from group 1 (vaccinated pigs) fared better in all aspects of this example than did the pigs from group 2 (pigs given sterile diluent). Clinical scores, rectal temperatures, and percent lung involvement were all higher for the pigs given sterile diluent. Weight gain and white blood cell counts were lower for the pigs receiving the sterile diluent. There was also a significant reduction in viremia beginning on day 4 post-challenge in the group given vaccine. On days 10 and 11 post-challenge, the number of animals positive for viremia decreased further in the vaccinated group, but remained the same in the group receiving sterile diluent.

An ELISA was used to monitor anti-PRRSV serological status prior to and following vaccination and challenge. All pigs were negative (S/P ratio<0.4) at the time of vaccination. All pigs including the vaccinates were negative at 7 DPV (Days Post Vaccination). Seven days later, 21 of 22 vaccinated pigs were tested as positive for antibody to PRRSV. Two pigs of group 1 remained negative during the pre-challenge period and serological converted at 8 days post challenge (8 DPC). All of the pigs in group 2 were negative at trial day 0 and remained negative throughout the pre-challenge period. On trial day 39 (8 DPC) 17 of the 22 non-vaccinated challenged pigs (Group 2) tested as sero positive. All of the pigs in group 3 (normal controls) remained sero-negative throughout the study.

Virus isolations from sera were performed before and after vaccination. Of the 22 vaccinated pigs, 17 were positive by 2 DPV, 18 were positive by 4 DPV and 19 were positive by 7 DPV. Following vaccination, vaccine virus was not recovered at all from one pig and not until 0 DPC for another. These results correspond to the sero-negative status of these pigs during the post vaccination observation period. At the time of challenge, 55% of the vaccinated pigs were viremic positive. Following challenge, this percentage rose to 82% (at 2 DPC) and gradually decreased to 9% on 11 DPC. All pigs in group 2 were negative at 0 DPC and increased to 82% positive at 2 DPC and 91% at 4 DPC. On 6 and 10 DPC, group 2 was approximately 82% virus positive and 73% of this group was positive on 11 DPC. The normal controls, group 3, remained negative for the duration of the study.

Rectal temperature monitoring showed an overall group increase experienced by group 2. One-half of the pigs in this group experienced a rise of 1° F. over the pre-challenge average for 2 or more days during the 11 day observation period. In comparison, only four of the 22 pigs in the vaccinated group experienced temperatures of 1° F. over their pre-challenge average. The average duration of those animals experiencing elevated temperatures for two or more days was 2.2 days for group 1 and 4 days for group 2. None of the pigs in group 3 experienced increases of 1° F. over their pre-challenge average for two days or longer.

Weight gain was monitored over the 11 day observation period. Pigs in group 3 gained an average of 1.06 pounds/day, pigs in group 2 gained an average of 0.94 pounds/day and pigs in group 1 gained an average of 0.53 pounds/day. Therefore, non-vaccinated challenged pigs gained only about 57% as much weight as did vaccinated challenged pigs and only 50% as much weight as the control group.

Leukopenia (white blood cell counts) were monitored during the post challenge observation period. Group 3 experienced a 5% reduction in the group average on trial day 33 (2 DPC) when compared to the pre-challenge average. For group 2, white blood cell counts dropped an average of 41% and did not return to pre-challenge levels until 11 DPC. The vaccinated group experienced a group average drop of 12% on trial day 34 (3 DPC). The counts returned to pre-challenge level on the next day and remained equal to the pre-challenge level for the duration of the observation period.

Daily clinical observations were made from trial day 28 (−4 DPC) through trial day 42 (11 DPC). All pigs were free of any observable clinical signs during the pre-challenge period. Group 3 remained free of any clinical signs for the duration of the post challenge period. Five of the pigs in group 2 were observed to have post challenge clinical signs. These signs became evident at 6 DPC and were not considered to be severe. The vaccinated pigs had only 1 clinical sign observed during the 11 day post challenge observation period.

At the termination of the study, lungs were evaluated for observable lung lesions. Group 3 had normal lungs and a group average score of 0.02. The individual pig scores for group 2 ranged from a low of 33 to a high of 98 for a group average of 78.33. The scores of the vaccinated group ranged from 30 to a high of 90 with a group average of 53.20.

The data in this example demonstrated the efficacy of a modified live Atypical PRRS viral vaccine. The vaccine was administered at a minimal dose of 2.0 logs per dose containing the fifth passage beyond the MSV (JA-142, passage 205). Efficacy of the vaccine was demonstrated by significantly reducing the extent of lung lesions, the severity of post challenge leukopenia, and post challenge fever. Additionally, a normal growth rate was maintained in vaccinated/challenged pigs compared to that achieved by the normal control pigs and significantly better than that achieved by non-vaccinated/challenged pigs.

EXAMPLE 6

Materials and Methods

This example compared four groups, groups 1, 2, and 3 having twenty pigs each, and group 4 having 10 pigs. Group 1 was inoculated intramuscularly (IM) with PRRS MSV, JA-142, passage 205, at a titer of about 2,5 logs/dose. Group 2 was inoculated intra-nasally with PRRS MSV, JA-142, passage 205, at a titer of about 5.0 logs/dose. Group 3 was inoculated IM with sterile diluent. Group 4 acted as strict controls. Pigs were challenged with a PRRSV isolate from South Dakota State University (SDSU) with an RFLP pattern of 144 on day 28 post-vaccination. Body temperatures of the pigs were monitored daily following challenge. Each animal was weighed at vaccination, challenge, weekly for the duration of the study, and necropsy. Blood samples were collected weekly following vaccination and every two days following challenge. The health status of each animal was monitored daily for the duration of the study. At the termination of the study, animals were sacrificed and their lungs scored for percent lung involvement.

PPRSV ELISA assays were performed following the exposures of the pigs with the test articles and challenge. Attempts to isolate PRRSV from serum samples were also performed on MA-104 cells following exposure to the test articles. WBC counts and clinical observations were determined post inoculation as in Example 2.

Results and Discussion

At zero days post vaccination (DPV), all pigs in this example were serologically negative to PRRSV as indicated by having a S/P ratio<0.4. At 14 DPV, 70% of the pigs in group 1 and 95% of the pigs in group 2 tested positive for the presence of anti-PRRSV antibody. Only one vaccinated pig of group 1, remained sero-negative throughout the pre-challenge period. This pig became sero-positive at seven days post challenge (DPC). All of the pigs in groups 3 and 4 remained negative throughout the pre-challenge period. At nine DPC, all of the pigs in group 3, the sterile diluent treated group, tested positive by ELISA for PRRSV antibody. The normal controls, group 4, remained negative for the duration of the study.

The virus isolation results correlated well with serological results. Only one pig remained negative for virus isolation from serum and this corresponded to the sero-negative status during the post vaccination period. These results indicate a relationship between post vaccination viremia and serological conversion with vaccine dosage. Group 2 was 100% sero-positive at 14 DPV as compared to 70% for group 1. The high dose group (group 2) was 85% and 90% viremia positive at 14 and 21 DPV, respectively. In comparison, the low dose group (group 1) was 55% and 85% positive for the same test days.

Following challenge, 89% of the animals in group 3 experienced temperatures that were one degree F or greater than the pre-challenge values for two or more days. In group 1, 75% of the animals experienced temperatures of one degree or greater for two or more days. While only 45% of the animals of group 2 experienced elevated temperatures. In comparison, 30% of the animals in the normal control group (group 4) experienced elevated temperatures for two or more days during the 11 day observation period.

Treatment with either the high vaccine dose or the low vaccine dose appeared to have no detrimental effect on the growth performance during the post-vaccination period (−3 DPV to 28 DPV). The average daily weight gain for groups 1 and 2 was 0.77 lbs./day and 0.76 lbs./day, respectively. For comparison, groups 3 and 4 had average daily weight gains of 0.77 lbs. and 0.78 lbs., respectively. Following challenge, the vaccinated groups outperformed the sterile diluent group by 0.05 lbs./day (group 1) and 0.15 lbs./day (group 2). The normal controls outgained the vaccinates during the same time period by an average of 0.4 to 0.5 lbs./day.

Eighty-four percent (16 of 19) of group 3, the sterile diluent treatment group, experienced a 25% or greater drop in their WBC count for one or more days after challenge. The normal controls had 3 of 10 (30%) that had experienced similar decreases. Following challenge, the vaccinated groups, the low dose (group 1)and the high dose (group 2) had 11 of 20 (55%) and 3 of 20 (15%) experiencing leukopenia of 25% for one or more days.

The clinical observations made prior to the challenge indicated that the pigs were of good health status. Following challenge, the level of health status did not significantly change for those pigs that were challenged (groups 1, 2, & 3). Lethargy, respiratory signs, and lost appetite were the clinical signs observed and these were described as mild in severity. The clinical signs reported for one pig in group 2 could be attributed to the bacterial pneumonia (see discussion below on lung lesions) that it was experiencing. The normal control group (group 4) was free of any observable clinical signs during the 11 day observation period.

At the termination of the study, pigs were sacrificed and the lungs were observed for PRRS-like lesions to score the extent of lung involvement. The percent of involvement was scored for each lobe then multiplied by the percent the lung represented for the total lung capacity. For example, 50% lung involvement for a diaphragmatic lobe was then multiplied by 25% to equal 12.5% of the total lung capacity. The maximum score that could be obtained was 100. The group average lung score for the normal controls (group 4) was zero. The group average score for the sterile diluent treatment group (group 3) was 70.08. The vaccinated treatment groups average scores were 48.83 for the low dose (group 1) and 17.76 for the high dose (group 2). One pig was observed to have a lung score of 62.5, the highest score within group 2. The lesions noted on this pig's lungs were described to be associated with bacterial pneumonia.

From the results of this study, both dosage levels of the atypical PRRS MSV vaccine reduced the severity of the clinical signs associated with the respiratory disease caused by the PRRSV. A full field dose outperformed the minimal dose as indicated by the significant reduction in lung lesion scores.

EXAMPLE 7

Materials and Methods

This example determined the sequence of the attenuated MSV, JA-142 from the 201st passage as well as the sequence of passage 3 of the field isolate virus, JA-142. The attenuated virus isolate was obtained from the master seed stock representing the 201st passage in MA-104 simian cells of a PRRSV isolated from swine affected with PRRS.

The virus was grown on 2621 cells, a monkey kidney cell line, also referred to as MA-104 and as USU-104 (Gravell et al., 181 Proc. Soc. Exp. Biol. Med. 112–119 (1986), Collins et al., Isolation of Swine Infertility and Respiratory Syndrome Virus (Isolate ATCC VR-2332) in North America and Experimental Reproduction of the Disease in Gnotobiotic Pigs, 4 J. Vet. Diagn. Invest. 117–126 (1992)) (the teachings of which are hereby incorporated by reference). Cells were cultured in 50 ml Dulbecco modified Eagle's MEM medium (Life Technologies, Inc., Gaithersburg, Md.), supplemented with 10% fetal calf serum and 50 µg/ml gentamicin (Sigma Chemical Co., St. Louis, Mo.) in a 5% humidified $CO_2$ atmosphere at 37° C. in 75 $cm^2$ plastic tissue culture flasks. Cells were maintained by passage at 5–7 day intervals. Cells were dislodged from the surface with trypsin-versene and split 1:4. To infect cells, media was decanted and 1 ml of cell supernatant containing virus at a titer of approximately $10^5$–$10^6$ tissue culture infective doses ($TCID_{50}$) was added for 30 min. Thirty ml fresh media containing 4% fetal calf serum was added. Cells were incubated as described above for 5 days, at which time cytopathic effect was evident in the culture. Culture medium containing virus was centrifuged at 2000 rpm in a Beckman TJ6 centrifuge to pellet cellular debris.

Viral genomic RNA was purified by adding 1120 µl of prepared Buffer AVL (QIAamp Viral RNA Isolation Kit, Qiagen)(QIAGEN, Inc. Valencia, Calif.)/carrier RNA to a 280 µl sample of virus-containing culture medium. The mixture was vortexed and incubated at room temperature for 10 min. 1120 µl ethanol was added and the mixture was inverted several times. RNA was absorbed to the matrix of a QIAamp spin column by repeated centrifugation of 630 µl aliquots at 6,000× g for 1 min. The column was washed with 500 µl buffer AW and centrifuged to remove all traces of wash solution. RNA was eluted from the column with 60 µl of diethylpyrocarbonate-treated water at room temperature. Purified RNA was stored at –70° C. or used immediately for synthesis of cDNA.

For cDNA synthesis, viral RNA was heated at 67° C. for 7 min, primed with random hexamers or PRRSV-specific primers, and reverse transcribed with Superscript II RNase H⁻ reverse transcriptase (RT) (Life Technologies, Inc.). Reactions contained 5 mM $MgCl_2$, 1× standard buffer II (Perkin Elmer Corp. Wellesley, Mass.), 1 mM each of dATP, dCTP, dGTP and dTTP, 1 unit/µl of RNase inhibitor, 2 units of RT, and 1 µl of RNA in a 40 µl reaction. Reaction mixtures were incubated for 15 min at 42° C., for 5 min at 99° C. and for 5 min at 5° C.

Polymerase chain reaction (PCR) was performed to obtained DNA fragments for sequencing as follows: 10 µl portions of cDNA reaction mixture were combined with the following reagents, resulting in a 25 µl reaction containing 2 mM $MgCl_2$, 1× standard buffer II (Perkin Elmer), 0.2 mM each of dATP, dCTP, dGTP and dTTP, 0.3 µM of 5'- and 3'-PRRSV-specific primer, and 0.375 units AmpliTaq Taq polymerase (Perkin Elmer). Reactions were prepared by heating for 4 min at 93° C. in a thermal cycler, then 35 cycles consisting of 50–59° C. for 30 sec, 72° C. for 30–60 sec, and 94° C. for 30 sec. Specific times and temperatures varied depending on the annealing temperatures of the primers in each reaction and the predicted length of the amplification product. A final incubation was performed for 10 min at 72° C. and reactions were placed at 4° C. PCR products were purified with a Microcon 100 kit (Amicon, Bedford, Mass.).

Rapid amplification of cDNA ends (RACE) PCR was performed to obtain the extreme 5'-end sequence of the genomic RNA, based on the method of Frohman, MA.,On Beyond Classic RACE (Rapid Amplification of cDNA Ends), 4 PCR Methods and Applications S40-S58 (1994) (the teachings of which are hereby incorporated by reference). Viral RNA was isolated and converted to cDNA as described above, with random hexamers as primers. Reaction products were purified on a Microcon 100 column (Amicon). A poly(dA) tail was added to the 3'-end by incubating 10 µl of cDNA in a 20 µl volume containing 1× buffer 4 (New England Biolabs, Beverly, Mass.), 2.5 mM $CoCl_2$, 0.5 mM dATP and 2 units terminal transferase (New England Biolabs), for 15 min at 37° C. The reaction was stopped by heating for 5 min at 65° C. and then was diluted to 200 µl with water.

PCR was performed using the Expand$^a$ Long Template PCR System (Boehringer Mannheim, Mannheim, Germany) in a 50 µl reaction volume containing 10 µl of diluted, poly(dA)-tailed cDNA, 1× buffer 3, 0.35 mM each of dATP, dCTP, dGTP and dTTP, 0.625 mM $MgCl_2$, 0.04 µM $Q_t$ primer (Frohman, 1994), 0.3 µM $Q_o$ primer (Frohman, 1994), 0.3 µM 5'-CGCCCTAATTGAATAGGTGAC-3' and 0.75 µl of enzyme mix. Reactions were heated at 93° C. for 2 min in a thermal cycler and cycled 25 times with each cycle consisting of 93° C. for 10 sec, 63° C. for 30 sec, and 68° C. for 12 min. After 25 cycles, the reaction was incubated at 68° C. for 7 min and held at 4° C. An aliquot of the reaction was diluted 100-fold and 5 µl of diluted product was added to a second PCR reaction containing, in 50 µl, 1× buffer 1, 0.35 mM each of dATP, dCTP, dGTP and dTTP, 0.3 µM primer Qi (Frohman, 1994), 0.3 µM 5'-CCTTCGGCAGGCGGGGAGTAGTGTTTGAGGTGCTCAGC-3', and 0.75 µl enzyme mix. Reactions were heated at 93° C. for 2 min in a thermal cycler and cycled 25 times with each cycle consisting of 93° C. for 10 sec, 63° C. for 30 sec, and 68° C. for 4 min. After 25 cycles, the reaction was incubated at 68° C. for 7 min and held at 4° C. Reaction products were electrophoresed on a 1% agarose gel and the band of approximately 1500 bp was purified using the QIAgen QXII gel purification kit. Eluted DNA was cloned into the pGEM-T vector (Promega, Madison, Wis.) using standard procedures. Individual clones were isolated and grown for isolation of plasmid DNA using QIAgen plasmid isolation kits.

PCR products and plasmid DNA were combined with appropriate primers based on related PRRSV sequences in Genbank or derived from known sequences, and subjected to automated sequencing reactions with Taq DyeDeoxy terminator cycle sequencing kits (Applied Biosystems, Foster City, Calif.) and a PR 2400 Thermocycler (Perkin Elmer) at the University of Minnesota Advanced Genetic Analysis Center. Reactions were electrophoresed on an Applied Biosystems 3700 DNA sequencer. Sequence base calling and proofreading were performed primarily with the Phred program (University of Washington Genome Center) and fragment assembly was performed primarily with the Phrap program (University of Washington Genome Center). Additional computer software including the Lasergene Package (DNASTAR Inc., Madison, Wis.), Wisconsin package version 9.1 (Genetics Computer Group, Madison, Wis.), and EuGene (Molecular Biology Information Resource, Houston, Tex.) was used to analyze the sequence. The final viral genomic sequence was assembled from approximately 100 PCR reactions and 428 DNA sequencing reactions.

Results

The results of Example 7 are given as SEQ ID Nos. 1 and 2 wherein SEQ ID No. 1 represents the DNA sequence of the 201st passage of the Master Seed Virus, JA 142 and SEQ ID No.2 represents the DNA sequence of the field-isolated virulent virus, JA 142 after three passages. Additionally, RNA sequences of the 201st passage JA-142 and the field isolated virulent virus, JA-142 are provided as SEQ ID Nos. 3 and 4, respectively. These RNA sequences vary slightly from the DNA sequences at the 5' end of the genome.

EXAMPLE 8

Materials and Methods

This example demonstrated the presence or absence of a NspI restriction endonuclease site for differentiation between field strains of PRRSV and an attenuated strain of PRRSV. Thus, this example provides a diagnostic testing method using restriction fragment length polymorphism (RFLP) analysis. RFLP is useful as a diagnostic tool because the NspI site is present in most field strains of PRRSV. Samples, preferably of serum, should be gathered from a suspected infected individual for RT-PCR/RFLP based diagnostic testing. In this case, known virulent field strains were used for testing to provide known result standards for later diagnostic testing. While Qiagen products and specific method steps are disclosed, it is understood that other methods and products known in the art can be utilized.

For performance of the diagnostic test (and to obtain the standards disclosed below) viral genomic RNA was isolated using a QIAamp Viral RNA Isolation Kit (Qiagen, Inc. Valencia, Calif.) and following the mini spin protocol. The following steps were used:

1. Carrier RNA was added to Buffer AVL and placed at 80° C. for five minutes or until dissolution of the precipitate to form solution 1. Do not heat Buffer AVL over 5 minutes or more than 6 times. Frequent warming/extended incubation will cause degradation of carrier-RNA, leading to reduced recovery of Viral RNA and eventually false negative RT-PCR results.
2. 1120 μl of solution 1 was pipetted into a microfuge tube.
3. 280 μl of serum sample was added to the microfuge tube holding solution 1 and the resulting mixture was vortexed thoroughly to ensure that solution 1 and the sample were well mixed together. This is done to lyse the sample under highly denaturing conditions, inactivate RNases, and ensure isolation of intact viral RNA. Carrier-RNA improves binding of viral RNA to the QIAamp membrane, and limits possible degradation of the viral RNA due to any residual RNase activity.
4. This mixture was incubated at room temperature for 10 minutes. Viral particle lysis is substantially complete after lysis for 10 minutes at room temperature, although longer times may be used with little or no effect on the yield or quality of the purified RNA.
5. 1120 μl of ethanol (EtOH) (96–100%) was added to the incubated mixture and mixed thoroughly by inverting the tube several times.
6. A QIAamp spin column was placed in a 2 ml collection tube and 630 μl of the mixture obtained in step five was added. This mixture was then centrifuged at 6000× g for one minute.
7. The filtrate in the collection tube was discarded.
8. The QIAamp spin column was placed into a clean 2 ml collection tube and another 630 μl of the mixture obtained in step five was added to the spin column and centrifuged at 6000× g.
9. The filtrate in the collection tube was discarded.
10. The QIAamp spin column was placed into a clean 2 ml collection tube and another 630 μl of the mixture obtained in step five was added to the spin column and centrifuged at 6000× g.
11. 500 μl of Buffer AW1 was added to the spin column and centrifuged at 6000× g for one minute.
12. The tube containing the filtrate was discarded.
13. The spin column was placed into a clean 2 ml collection tube and 500 μl of Buffer AW2 was added and centrifuged at 18,500× g for three minutes. The filtrate was discarded.
14. The spin column was placed into a new 2 ml collection tube and centrifuged at 6000× g for one minute to remove the last traces of AW2. The filtrate was discarded.
15. The spin column was placed into a clean 1.5 ml microcentrifuge tube and 60 μl of Buffer AVE at room temperature. This mixture was incubated for one minute at room temperature before being centrifuged at 6000× g for one minute to elute the RNA.
16. The eluted RNA was pipetted into a 1.5 ml microfuge tube and stored at −70° C. if the RT-PCR is not able to be done immediately.

RT-PCR was performed on the eluted RNA obtained in the above method. A 20 μl "master mix" containing the following: 5 μl of 1× RT-PCR buffer, 1 μl of 0.4 mM DNTP mixture (containing equal amounts each of dATP, dCTP, dGTP and dUTP), 0.1 μl of 0.08 units/Rx RNAse inhibitor, 0.5 μl 500 nM BVDV forward primer, 0.5 μl 500 nM BVDV reverse primer, 11.9 μl RNAse/DNAse free water, and 1 μl Qiagen "secret" enzyme mix was added to a tube. 5 μl of the eluted RNA was then added to the tube.

Reactions were initially heated at 50° C. for 30 minutes followed by heating at 95° C. for 15 minutes in a thermal cycler and then cycled 35 times with each cycle consisting of 57° C. for 30 seconds, 72° C. for 45 seconds, and 94° C. for 45 seconds. After 35 cycles, the reaction was incubated at 57° C. for 30 seconds followed by 72° C. for 7 minutes and finally held at 4° C. To check the PCR on an agarose gel, 1 g of agarose was added to 100 ml of 1× TAE buffer before microwaving on high for two minutes. Next, 4 μl of 10 mg/ml EtBr was added to the heated gel before casting the gel and allowing it to solidify for 15–30 minutes. 4 μl of the PCR product was mixed with 1 μl loading dye. 3.5 μl of a 1 Kb ladder was added to 13.2 μl of water and 3.3 μl of loading dye for use as a marker. 4 μl of the marker mixture was electrophoresed on the gel, indicating a 1 Kb product. A band from the PCR product should be approximately 1 Kb in size. The gel was then run at 140 volts for 1 hour or 75 volts for two hours.

The band of approximately 1 Kb was purified using the QIAgen Qiaquick PCR Purification Kit (Qiagen, Inc. Valencia, Calif.). A column was placed in a collection tube and 20 μl PCR reaction sample and 100 μl PB buffer were added. This mixture was mixed thoroughly before spinning for 1 minute at full speed in an Eppendorf microfuge. The flow-through products were discarded and the column was replaced in the tube. The tube was spun for another full minute and allowed to stand for at least one minute at room temperature. The column was then spun a third time at full speed. The eluent remaining contains purified PCR product and water.

The PCR/water product from above was then digested with Nsp I, a restriction enzyme and then electrophoresed on a 1.5% agarose gel to determine fragment numbers and lengths.

Results

The results of Example 8 are used for diagnostic results. It was found that most of the field strains for the PRRS virus contain one Nsp I restriction site, therefore yielding digestion products of 549 and 476 bp from the 1 Kb RT-PCR product. The parent strain of the JA-142 passage 200 possesses this phenotype. Only one PRRS strain, BI-Vetmedica 142 passage 200 (+5), contains two Nsp I sites, yielding digestion products of 476, 380, and 173 bp from the 1 Kb RT-PCR product. Some field strains possess no Nsp I site within this RT-PCR product, and therefore exhibit no digestion and electrophoresis of one fragment of 1021 bp. Thus, the presence of the attenuated virus can be determined.

EXAMPLE 9

Materials and Methods:

This Example tested the degree of protective immunity against maternal reproductive failure of swine vaccinated by one or two attenuated strains of PRRSV.

Fifty gilts were separated into five experimental groups designated A–E and having ten gilts in each group. Gilts of group A were neither vaccinated nor challenged and were therefore used as strict controls. Gilts of group B were used as the challenge controls and therefore received no vaccinations but were challenged at or about day 90 of gestation. Gilts of groups C, D, and E were each vaccinated twice before conception with one month between vaccinations. These gilts were then challenged at or about day 90 of gestation. Two strains of vaccine virus (strains RespPRRS/Repro and JA-142) were used to challenge the gilts. The challenge consisted of oronasal exposure to virulent PRRSV. Gilts of group C were vaccinated twice with strain RespPRRS/Repro. Gilts of group D were vaccinated first with RespPRRS/Repro and then with JA-142. Gilts of group E were vaccinated twice with strain JA-142. Gilts and their progeny were observed at least twice daily for clinical signs and tested for both PRRSV and homologous antibody at selected intervals. The gilts of groups C, D, and E were bled just before their first vaccination and at selected times thereafter until they were necropsied, usually at or about 14 days after farrowing or sooner if they aborted. Gilts of group A and B were bled just before challenge and at identical selected times thereafter. Beginning one month after the second vaccination of groups C, D, and E, all gilts were bred as they came into estrus. All of the boars used for breeding purposes were free of antibody against PRRSV. Near the time of challenge, each gilt was moved to an isolation room and was kept in isolation until the experiment was ended for that gilt and her litter at two weeks after farrowing or sooner in the case of abortion or premature death of all progeny. All surviving pigs were weighed when they were two weeks old. Gilts that failed to conceive at their first, second, or third estrocycle were excluded from the experiment. This reduced the numbers of pregnant gilts for groups B, C, D, and E to 9, 8, 9, and 9, respectively. The same limitation did not apply to group A because for this group, there were more than ten nonvaccinated gilts available from which to make a random selection for inclusion in group A.

Results and Discussion:

All vaccinated gilts (groups C, D, and E) responded to vaccination with the production of antibodies against PRRSV. These results are provided in FIG. 1 which is a graph representing the ratio of the total number of samples to samples positive for PRRSV antibodies. Blood samples were collected from the gilts just before their first vaccination and at selected times thereafter during an interval of 196 days. Depending on when gilts conceived (breeding was started on day 60), they were progressively removed from this group. Beginning at or about 90 days of gestation, blood samples were collected just before they were challenged, seven days after challenge, fourteen days after challenge, at the time of delivery (which was at or about 24 days after challenge if the gilt farrowed normally, or sooner if the gilt aborted), and at the time of necropsy (which was at or about 38 days, i.e. 2 weeks after farrowing, or sooner if the gilt lost all of her live born pigs before 2 weeks after farrowing). These results are provided in FIG. 2.

Figure 2:
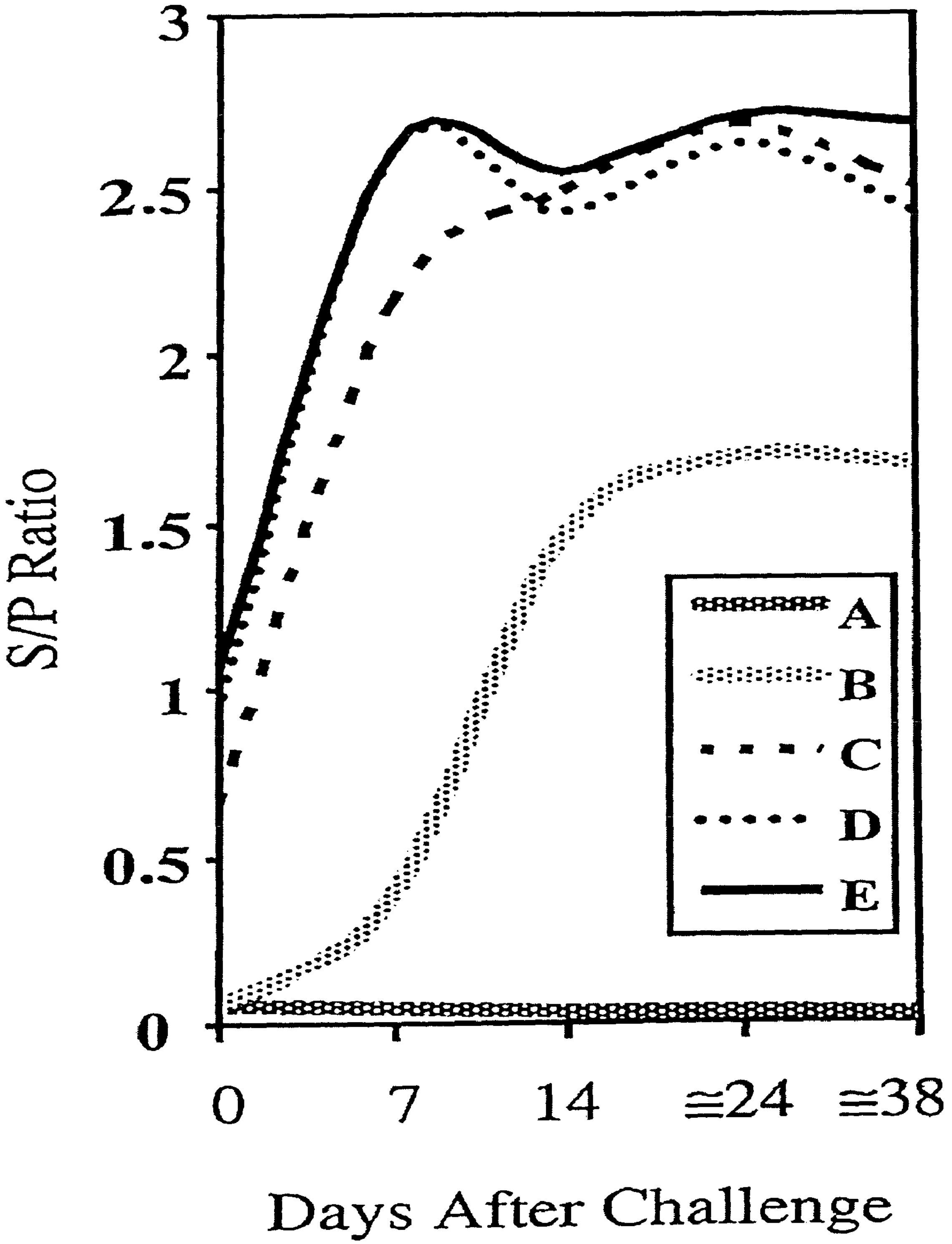
FIG. 2 is a graph illustrating the ratio of samples which tested positive for antibodies against PRRSV to the total number of samples over a 38 day testing period after challenge.

As shown in FIGS. 1 and 2, antibody levels increased after challenge for groups B, C, D, and E. For group B, the nonvaccinated group, these antibodies appeared only after challenge while they were present prior to challenge for groups C, D, and E. Gilts of group A and all boars used for breeding both vaccinated and nonvaccinated gilts remained free of antibody against PRRSV throughout the experiment. None of the vaccinated gilts had any obvious vaccine-related clinical signs after vaccination. Conversely, all of the gilts (both vaccinated and nonvaccinated) had moderate to severe clinical signs following challenge. A summary of the number of live born and still born pigs, the number of aborted, late term dead, and mummified fetuses, and the number and weight of pigs still alive 14 days after farrowing is presented in Table 4. All of the pigs of groups C, D, and E that survived through day 14 were robust and were judged to be in excellent health. None of these pigs yielded infectious virus from either serum or lung lavage samples. In contrast, all pigs of group B that survived through day 14 were unthrifty and were shown by virus isolation to be infected. A measure of the difference in general health is provided by the relative body weights of pigs of group B versus those of pigs of groups A, C, D, and E. The appearance of pigs of group B suggested that few, if any, would have recovered or would have recovered sufficiently to warrant any expectation of their continued survival under conditions of commercial swine production.

TABLE 4

Effect of Vaccination Against Porcine Reproductive and Respiratory Syndrome Virus (PRRSV) on the Health and Survival of Fetuses and Pigs of Gilts Subsequently Exposed to Highly Virulent PRRSV

| | | Day 0[1] | | | | | Day 14[2] | | |
|---|---|---|---|---|---|---|---|---|---|
| Group | Gilts[3] | Liveborn pigs | Stillborn pigs | Late-term dead fetuses | Mummified fetuses | Aborted fetuses | Live pigs | Mean pig weight (lbs) | Mean litter weight (lbs) |
| A | 10 | 102 | 17 | 1 | 2 | 0 | 95 | 9.8 | 93.1 |
| B | 9 | 24 | 3 | 62 | 5 | 0 | 16 | 5.6 | 10.0 |

TABLE 4-continued

Effect of Vaccination Against Porcine Reproductive and Respiratory Syndrome Virus (PRRSV) on the Health and Survival of Fetuses and Pigs of Gilts Subsequently Exposed to Highly Virulent PRRSV

| | | Day 0[1] | | | | | | Day 14[2] | |
|---|---|---|---|---|---|---|---|---|---|
| Group | Gilts[3] | Liveborn pigs | Stillborn pigs | Late-term dead fetuses | Mummified fetuses | Aborted fetuses | Live pigs | Mean pig weight (lbs) | Mean litter weight (lbs) |
| C | 8 | 37 | 8 | 31 | 4 | 13 | 27 | 11.1 | 37.5 |
| D | 9 | 47 | 10 | 14 | 0 | 39 | 38 | 8.7 | 36.7 |
| E | 9 | 50 | 13 | 38 | 3 | 0 | 33 | 10.4 | 38.1 |

[1]At the time of farrowing.
[2]On the day the experiment was ended.
[3]Pregnant gilts that aborted or farrowed.

Vaccination with either strain (RespPRRS/Repro and JA-142) of attenuated PRRSV provided a level of protective immunity that was demonstrated by challenge exposure. Although protection was incomplete regardless of the vaccine strain or method of vaccination, it was sufficient to recommend vaccination as an economically beneficial procedure. Whereas the loss of pigs of group B was essentially complete either due to death or ill health, about 40% of the pigs of litters of groups C, D, and E (on a per litter basis and using 100% as the value for litters of group A) would have survived to market. The excellent health status of the surviving pigs of groups C, D, and E is emphasized by the fact that the mean body weight of pigs of these groups (when calculated collectively) is the same as that of pigs of group A. The economic impact of saving about 3.6 pigs/litter through vaccination is difficult to project with certainty, however, if a reasonable assumption is made that each pig is worth about $20.00 in profit and reduced overhead through sharing of fixed costs, then two vaccinations at an estimated cost of about $1.00 each would return $72.00 for each $2.00 invested. On the basis of these assumptions, anything more than a prevalence of PRRSV-induced reproductive failure of one case for every 36 pregnancies (or a severe clinical epidemic once every 18 months assuming 2 pregnancies/year) would make vaccination cost effective. Moreover, it seems likely that the results of this study present the worst case scenario. Namely, the strain used for challenge was selected to represent the most virulent field strains of PRRSV currently present in North America and may not accurately reflect the majority of field strains against which vaccines are likely to be more protective.

We claim:

1. A method of differentiating between attenuated and virulent strains of PRRSV, said strains having RNA which is cleaved into known fragment numbers or lengths after cleavage by the Nsp1 restriction enzyme, depending upon whether the strain is attenuated or virulent, said method comprising the steps of:
  - obtaining a sample containing PRRSV viral RNA;
  - isolating said RNA from said sample;
  - digesting said RNA with said restriction enzyme;
  - determining fragment numbers or lengths after said digesting;
  - correlating said determined fragment numbers or lengths with said known fragment numbers or lengths; and
  - differentiating between attenuated and virulent strains of PRRSV based on the results of said correlating step.

2. The method of claim 1, said known fragment lengths including fragments of about 476, 380, and 173 base pairs in length.

3. The method of claim 1, said isolated RNA including a portion approximately 1 Kb in length.

4. The method of claim 3, said 1 Kb portion being subjected to said digesting.

5. The method of claim 3, further including the step of performing RT-PCR on said 1 Kb portion.

6. A method of predicting whether a PRRSV strain will be virulent or avirluent comprising the steps of:
  - digesting isolated PRRSV RNA with the Nsp1 restriction enzyme;
  - determining the number of fragments resulting from said digesting step; and
  - basing the prediction on the number of said resultant fragments, wherein a prediction of virulence will result when the digestion results in two or fewer fragments.

7. A method of predicting whether a PRRSV strain will be virulent comprising the steps of:
  - counting the number of Nsp1 restriction sites in a PRRSV RNA sequence; and
  - predicting that the strain will be virulent when there is one or zero Nsp1 restriction sites in said sequence.

* * * * *

SEQUENCE LISTING

```
<160> NUMBER OF SEQ ID NOS: 4

<210> SEQ ID NO 1
<211> LENGTH: 15424
<212> TYPE: DNA
<213> ORGANISM: Porcine reproductive and respiratory syndrome virus

<400> SEQUENCE: 1

tcgcccgggc aggtgttggc tctatgcctt ggcatttgta ttgtcaggag ctgcgaccat      60

tggcacagcc caaaactagc tgcacagaaa acgcccttct gtgacagccc tcttcagggg     120

agcttagggg tctgtcccta gcaccttgct tccggagttg cactgcttta cggtctctcc     180

aaccctttaa ccatgtctgg gatacttgat cggtgcacgt gcacccccaa tgccagggtg     240

tttatggcgg agggccaagt ctactgcaca cgatgtctca gtgcacggtc tctccttcct     300

ctgaatctcc aagttcctga gcttggagtg ctgggcctat tttacaggcc cgaagagcca     360

ctccggtgga cgttgccacg tgcattcccc actgttgagt gctcccccgc cggggcctgc     420

tggctttctg cgatctttcc aattgcacga atgaccagtg gaaacctgaa ctttcaacaa     480

agaatggtgc gggtcgcagc tgagatttac agagccggcc agctcacccc tgcagtcttg     540

aaggctctac aagtttatga acggggttgc cgctggtacc ctatagtcgg acctgtccct     600

ggagtggccg attttgccaa ctccctacat gtgagtgata aacctttccc gggagcaact     660
```

-continued

```
catgtgctaa ccaacctgcc actcccagag aggcctaagc ctgaagactt ttgcccttct    720
gagtgtgcta tggctgacgt ctatgatatt ggccatggcg ccgtcatgta tgtggccaaa    780
gggaaagtct cctgggcccc tcgtggcggg gatgaggcga aatttgaacc tgtccctagg    840
gagttgaagt tgatcgcgaa ccaactccac atctccttcc cgccccacca cgcagtggac    900
atgtctaagt ttgtgttcat agcccctggg agtggtgtct ctatgcgggt cgagtgccca    960
cacggctgtc tccccgctaa tactgtccct gaaggtaact gctggtggcg cttgtttgac   1020
tcgctcccac tggacgttca gaacaaagaa attcgccgtg ccaaccaatt cggctatcaa   1080
accaagcatg gtgtcgctgg caagtaccta caacggaggc tgcaagctaa tggtctccga   1140
gcagtgactg atacagatgg acccattgtc gtacagtatt tctctgttag ggagagctgg   1200
atccgccact tcagactggc ggaagagcct agcctccctg ggtttgaaga cctcctcaga   1260
ataagggtag agcccaatac gtcgccattg agtgacaagg gtggaaaaat cttccggttt   1320
ggcagtcaca aatggtacgg tgctggaaag agagcaagga aagcacgctc tggtatgacc   1380
accacagtcg ctcaccgcgc cttgcccgct cgtgaaatcc agcaagccaa aaagcacgag   1440
gatgccggcg ctgataaggc tgtgcatctc aggcactatt ctccgcctgc cgacgggaac   1500
tgtggttggc actgcatttc cgccatcgcc aaccgaatgg tgaattccaa atttgaaact   1560
actcttcccg agagggtgag accttcagat gactgggcta ctgacgagga ccttgtgaac   1620
accatccaaa ttctcaagct ccctgcggcc ttggacagga acggtgcttg tgttggcgcc   1680
aaatacgtgc ttaagctgga aggcgagcat tggactgtct ctgtgaccct tgggatgtcc   1740
ccttctttgc tccccccttga atgtgttcag ggctgttgtg agcataagag cggacttggt   1800
cccccagatg cggtcgaagt tttcggattt gaccctgcct gccttgaccg actggctgag   1860
gtaatgcact tgcctagcag tgtcatccca gctgctctgg ccgaaatgtc cggcgacccc   1920
aaccgtccgg cttccccggt cactactgtg tggactgttt cacaattctt tgcccgccac   1980
agaggaggag agcaccctga tcaggtgcgc ttaggaaaaa tcatcagcct ttgtcaagtt   2040
gttgaggaat gctgttgcca tcagaataaa accaaccggg ccaccccgga agaggttgcg   2100
gcaaggattg atcagtacct ccatggtgca acaagtcttg aagaatgctt gattaggctt   2160
gagagggttt gcccgccgag cgctgcggac accttctttg attggaatgt tgtgctccct   2220
ggggttgggg cttcaactca gacaaccaaa cagctccatg tcaaccagtg ccgcgctctg   2280
gttcctgtcg tgactcaaga gcctttggac aaagacccag tccctctgac cgccttctcg   2340
ctgtccaatt gctactatcc tgcacaaggt gacgaggttc gtcaccgtga gaggctaaac   2400
tccgtactct ctaagctgga gggggttgtt cgtgaggaat atgggctcac gccaactgga   2460
cctggcccgc gacccgcact accgaacggg ctcgtcgaac ttaaagacca gatggaggag   2520
gatctgctaa aactagtcaa cgcccaggca acttcagaaa tgatggcctg ggcagccgag   2580
caggttgatc tgaaagcttg ggtcaaaaac tacccacggt ggacaccgtc acccccctcca   2640
ccaagagttc agcctcgaaa aacaaagcct gtcaagagct tgccagggaa caaacctgtc   2700
cccgctccac gcaggaaggt cagatctgat tgtggcagcc cgatttcgat gggcgacaat   2760
gttcctgacg gtcgggaaga tttgactgtt ggtggccccc ttgatctttc gacaccatcc   2820
gagccgatga cacctctgag tgagcctgca cctatgcccg cgttgcaata tatttctagg   2880
ccagtgacac ctttgagtgt gctggcccca gtacctgcac cgcgtagaac tgtgtcccga   2940
ccggtgacgc ccttgagtga gccaattttt gtgtctgcac cgcgacacaa atttcagcag   3000
gtggaagaag cgaatctggc ggcaacaatg ctgacgcacc aggacgaacc tctagatttg   3060
```

-continued

```
tctgcatcct cacagactga atatgaggct tctcccctaa caccactgca gaacatgggt   3120
attctggagg tgggggggca agaagctgag gaagttctga gtgaaaactc ggatacactg   3180
aatgacatca accctgcacc tgtgtcatca agcagctccc tgtcaagtgt taagatcaca   3240
cgcccaaaac actctgctca agccatcatt gactcgggcg ggccctgcag tgggcatctc   3300
cgaaagggaa aagaagcatg cctcagcatc atgcgtgagg cttgtgatgc ggctaagctt   3360
agtgaccctg ccacgcagga atggctttct cgcatgtggg atagggttga tatgctgact   3420
tggcgcaaca cgtctgctta ccaggcgttc cgcatcttag atggtaggtt tgagtttctc   3480
ccaaagatga tactcgagac accgccgccc tacccgtgtg ggtttgtgat gctgcctcgc   3540
acgcctgcac cttccgtggg tgcagagagt gaccttacca ttggttcagt cgccactgaa   3600
gatgttccac gcatcctcgg gaaaatagaa aacgccggca agatgcccaa ccaggggctc   3660
ttgacatcct tcggggaaga accggtgtgc gaccaacctg tcaaggactc ctggatgtcg   3720
tcgcgggggt ttgacgagag cacaacggct ccgtccgctg gtacaggtgg tgctgactta   3780
cccaccgatt tgccaccttc agatggtttg gatgcggacg agtgggggcc gttacggacg   3840
gtaagaaaga aagctgaaag gctcttcgac caattgagcc gtcaggtttt taacctcgtc   3900
tcccatctcc ctgttttctt ctcacacctc ttcaaatctg acagtggtta ttctccgggt   3960
gattggggtt ttgcagcttt tactttattt tgcctctttt tgtgttacag ctacccattc   4020
tttggttttg ttcccctctt gggtgttttt tctgggtctt ctcggcgtgt gcgcatgggg   4080
gtttttggct gttggttggc ttttgctgtt ggcctgttca agcctgtgtc cgacccagtc   4140
ggcactgctt gtgagtttga ctcgccagag tgtaggaacg tccttcattc ttttgagctt   4200
ctcaaacctt gggaccctgt tcgcagcctt gttgtgggcc ccgtcggtct cggccttgcc   4260
attcttggca ggttactggg cggggcacgc tacatctggc attttttgct taggcttggc   4320
attgttgcag attgtatctt ggctggagct tatgtgcttt ctcaaggtag gtgtaaaaag   4380
tgctggggat cttgtgtaag aactgctcct aatgaaatcg ccttcaacgt gttccctttt   4440
acgcgtgcga ccaggtcgtc actcatcgac ctgtgcgatc ggttttgtgc gccaaaaggc   4500
atggacccca ttttcctcgc tactgggtgg cgcgggtgct ggaacggccg aagtcccatt   4560
gagcaaccct ctgaaaaacc catcgcgttc gcccagttgg atgaaaagag gatcacggct   4620
agaactgtgg tcgctcagcc ttatgatcct aaccaagccg taaagtgctt gcgggtgtta   4680
caggcgggtg gggcgatagt ggccgaggca gtcccaaaag tggtcaaggt ttccgctatt   4740
ccattccgag ctcccttttt tcccaccgga gtgaaggttg atcctgagtg caggatcgtg   4800
gtcgaccccg acacttttac tacagctctc cggtctggtt actccaccac aaacctcgtc   4860
cttggtgtag ggactttgc  ccaactgaat ggattaaaaa tcaggcaaat ttccaagccc   4920
tcgggaggag gcccgcacct cattgctgcc ctgcatgttg cttgctcgat ggcgttgcac   4980
atgcttgctg gagtttatgt aactgcagtg gggtcttgcg gtaccggcac caacgatccg   5040
tggtgcacta acccattcgc cgtccctggc tacggacctg gctccctctg cacgtccaga   5100
ttgtgcatct cccaacatgg ccttaccctg cccttgacag cacttgtggc aggattcggt   5160
cttcaggaaa ttgccctagt cgttttgatt ttcgtttcca tcggaggcat ggctcatagg   5220
ttgagttgta aggctgatat gctgtgcgtc ttacttgcaa tcgccagcta tgtttgggta   5280
ccccttacct ggttgctctg tgtgtttcct tgctggttgc gctggttctc tttgcaccct   5340
ctcaccattc tatggttggt gtttttcttg atgtctgtaa atatgccttc gggaatctta   5400
```

-continued accgtggtgt tattggttgc tctttggctt ctaggccgtt atactaatgt tgttggtctt 5460
gttacccccct atgatattca ccattacacc aatggccccc gcggtgttgc cgccttggct 5520
accgcaccag atgggactta cttggccgct gtccgccgcg ctgcgttgac tggccgcacc 5580
gtgctgttta ccccgtctca gcttgggtcc cttcttgagg gcgctttcag aactcgaaag 5640
ccctcactga acaccgtcaa tgtggtcggg tcctccatgg gctctggcgg agtgttcact 5700
atcgatggga aaattaagtg cgtgactgcc gcacatgtcc ttacgggtaa ttcagccagg 5760
gtttccgggg tcggctttaa tcaaatgctt gactttgatg taaaagggga cttcgccata 5820
gctgactgcc cgaattggca aggggctgct cctaagaccc aattctgcga ggatggatgg 5880
actggccgcg cctattggct gacatcctct ggcgtcgaac ccggtgtcat tgggaatgga 5940
ttcgccttct gcttcaccgc gtgcggcgat tccgggtccc cagtgatcac cgaagccggt 6000
gagcttgtcg gcgttcacac aggatcaaac aaacaaggag gaggcattgt tacgcgcccc 6060
tctggccagt tttgcaatgt ggcacccatc aagctgagcg aattaagtga gttctttgct 6120
ggacctaagg tcccgctcgg tgatgtgaag gttggcagcc acataattaa agacatatgc 6180
gaggtacctt cagatctttg cgccttgctt gctgccaaac ccgaactgga aggaggcctc 6240
tccaccgtcc aacttctgtg tgtgtttttc ctcctgtgga gaatgatggg acatgcctgg 6300
acgcccttgg ttgctgttgg gttttttatc ttgaatgagg ttctcccagc tgtactggtc 6360
cggagtgttt tctcctttgg aatgtttgtg ctatcttggc tcacaccatg gtctgcgcaa 6420
gttctgatga tcaggcttct aacagcagct cttaacagga acagattgtc actcgccttt 6480
tacagccttg gtgcagcgac cggttttgtc gcagatctgg cggcaactca agggcacccg 6540
ttgcaggcag taatgaattt aagtacctat gccttcctgc ctcggataat ggtcgtgacc 6600
tcaccagtcc cagtgattgc gtgtggtgtt gtgcacctcc ttgccataat tttgtacttg 6660
tttaagtacc gctgcctgca caatgtcctt gttggcgatg gtgcgttctc tgcggctttc 6720
ttcttgcgat actttgccga ggggaaattg agggaagggg tgtcgcaatc ctgcgggatg 6780
aatcatgagt cgctgactgg tgccctcgct atgagactta atgacgagga cttggatttt 6840
cttacgaaat ggactgattt taagtgtttt gtttctgcat ccaacatgag gaatgcggcg 6900
ggccagttca tcgaggctgc ctatgctaaa gcacttagaa ttgaacttgc ccagttggtg 6960
caggttgata aggttcgagg tactttggcc aaacttgaag cttttgctga taccgtggca 7020
ccccaactct cgcccggtga cattgttgtt gctcttggcc atacgcctgt tggcggtatc 7080
ttcgacctaa aggttggtag caccaagcat accctccaag ccattgagac cagagttctt 7140
gccgggtcca aaatgaccgt ggcgcgtgtc gttgatccaa cccccacacc cccacccgca 7200
cccgtgccta tccccccttcc accgaaagtt ctggagaatg gtcccaacgc ctggggggat 7260
gaggatcgtt tgaataagaa gaagaggcgc aagatggaag ccgtcggcat ctttgttatg 7320
ggtggaaaga aatatcagaa attttgggac aagaactccg gtgatgtgtt ttatgaggag 7380
gtccatgata acacagacgc gtgggagtgc ctcagagttg acaaccctgc cgactttgac 7440
cctgagaagg gaactctgtg cgggcatact accattgaag ataagactta cagtgtctac 7500
gcctccccat ctggcaagaa attcctggtc cccgcctacc cagagagcaa aaaaaaccaa 7560
tgggaagctg cgaagctttc cgtggaacag gcccttggca tgatgaatgt cgacggtgaa 7620
ctgacagcca aagaagtgga gaaactgaaa agaataattg acaaactcca gggcctgact 7680
aaggagcagt gtttaaactg ctagccgcca gcggcttgac ccgctgtggt cgcggcggct 7740
tggttattac tgagacagcg gtaaaaatag tcaaatttca caaccggacc ttcaccctag 7800

-continued

```
gacctgtgaa tttaaaagtg gccagtgagg ttgagctaaa agacgcggtc gagcataacc   7860
aacacccggt tgcaagaccg gttgatggtg gtgttgtgct cctgcgctcc gcagttcctt   7920
cgcttataga cgtcttaatc tccggcgctg atgcatctcc caagttactc gcccgccacg   7980
ggccgggaaa cactgggatc gatggcacgc tttgggattt tgaggccgag gccactaaag   8040
aggaaattgc actcagtgcg caaataatac aggcttgtga cattaggcgc ggcgacgcac   8100
ctgaaattgg tcttccttat aagctgtacc ctgtcagggg caaccctgag cgggtaaaag   8160
gagttttaca gaatacaagg tttggagata taccttataa aacccccagt gacactggaa   8220
gcccagtgca cgcggctgcc tgcctcacgc ccaatgccac tccggtgact gatgggcgct   8280
ccgtcttggc cacgactatg ccctccggtt ttgagttgta tgtaccgacc attccagcgt   8340
ctgtccttga ttatcttgat tctaggcctg actgccccaa acagttgaca gagcacggct   8400
gtgaggacgc cgcattaaga gacctctcca agtatgactt gtccacccaa ggctttgttt   8460
tacctggagt tcttcgcctt gtgcgtaagt acctgtttgc tcatgtgggt aagtgcccgc   8520
ccgttcatcg gccttccact taccctgcca agaattctat ggctggaata aatgggaaca   8580
ggtttccaac caaggacatc cagagcgtcc ctgaaatcga cgttctgtgc gcacaggccg   8640
ttcgggaaaa ctggcaaact gttacccctt gtaccctcaa gaaacagtat tgtgggaaga   8700
agaagactag gacaatactc ggcaccaata acttcattgc gctggctcac cgggcagcgt   8760
tgagtggtgt cacccagggc ttcatgaaaa aggcgtttaa ctcgcccatt gccctcggta   8820
aaaacaaatt taaagagctt cagactccgg tcttaggcag gtgccttgaa gctgatcttg   8880
catcctgcga tcgctccaca cctgcaattg tccgctggtt tgccgccaat cttctttatg   8940
aacttgcctg tgctgaagag caccagccgt cgtacgtgtt gaactgctgc cacgacctac   9000
tggtcacgca gtccggcgca gtaactaaga gaggtggcct gtcgtctggc gacccgatca   9060
cttctgtgtc caacaccatt tacagcttgg tgatatatgc acaacacatg gtgctcagtt   9120
actttaaaag tggtcaccct catggccttc tgtttctaca agaccagctg aagtttgagg   9180
acatgctcaa ggttcaaccc ctgatcgtct attcggacga cctcgtactg tatgccgagt   9240
ctcccaccat gccaaactac cactggtggg ttgaacatct gaacctgatg ctgggttttc   9300
agacggaccc aaagaagaca gccataacag actcgccatc atttctaggc tgtaggataa   9360
taaatggacg ccagctcgtc cctaaccgtg acaggattct cgcggccctc gcctaccata   9420
tgaaggcaag caatgtctct gaatactacg cctcggcggc tgcgatactc atggacagct   9480
gtgcttgttt agagtatgat cccgaatggt ttgaagagct tgtagttggg atagcgcagt   9540
gtgcccgcaa ggacggctac agttttcccg gcccgccgtt cttcttgtcc atgtgggaaa   9600
aactcagatc caatcatgag gggaagaagt ccagaatgtg cgggtactgc ggggccccgg   9660
ctccgtacgc cactgcctgt ggcctcgacg tctgtattta ccacacccac ttccaccagc   9720
attgtccagt catcatctgg tgtggccacc cggctggttc tggttcttgt agtgagtgca   9780
aacccccccct agggaaaggc acaagccctc tagatgaggt gttagaacaa gtcccgtata   9840
agcctccacg gactgtaatc atgcatgtgg agcagggtct caccccctctt gacccaggca   9900
gataccagac tcgccgcgga ttagtctccg ttaggcgtgg cattagagga aatgaggttg   9960
atctaccaga cggtgattat gctagcaccg ccctactccc tacttgtaaa gagattaaca  10020
tggtcgctgt cgcctctaat gtgttgcgca gcaggttcat catcggcccg cctggtgctg  10080
ggaaaacata ctggctcctt caacaggtcc aggatggtga tgccatttac acgccaactc  10140
```

-continued

```
accagaccat gctcgatatg attagggctt tggggacgtg ccggttcaac gtcccagcag  10200
gtacgacgct gcaattccct gccccctccc gtaccggccc ttgggttcgc atcctagccg  10260
gcggttggtg tcctggcaag aattccttcc tggatgaagc agcgtattgt aatcaccttg  10320
atgtcttgag gcttcttagc aaaactaccc tcacctgtct gggagatttc aaacaactcc  10380
acccagtggg ttttgattct cattgctatg tttttgacat catgcctcag actcaactga  10440
agaccatctg gagatttgga cagaatatct gtgaggccat tcagccagat tacagggaca  10500
aacttgtatc catggtcaac acaacccgtg taacctacgt ggaaaaacct gtcaagtatg  10560
ggcaagtcct cacccccttac cacagggacc gagaggacgg cgccatcaca attgactcca  10620
gtcaaggcgc cacatttgat gtggttacac tgcatttgcc cactaaagat tcactcaaca  10680
ggcaaagagc ccttgttgct attaccaggg caagacatgc tgtctttgtg tatgacccac  10740
acaggcaact gcagagcatg tttgatcttc ctgcgaaagg cacacccgtc aacctcgctg  10800
tgcaccgtga cgagcagctg atcgtgctag atagaaataa caaagaatgc acggttgctc  10860
aggctctagg caatggggat aaattcaggg ccacagacaa gcgcgttgta gattctctcc  10920
gcgccatttg tgcagatctg gaagggtcga gctccccgct ccccaaggtc gcacacaact  10980
tgggatttta tttctcgcct gatttgacac agtttgctaa actcccggta gaacttgcac  11040
cccactggcc cgtggtgaca acccagaaca atgaaaagtg gccagaccgg ttggttgcta  11100
gccttcgccc cgtccataag tatagccgcg cgtgcatcgg tgccggctac atggtgggcc  11160
cctcagtgtt tctgggcacc cctggggttg tgtcatacta tctcacaaaa tttgtcaggg  11220
gcgaggctca aatgcttccg gagacagtct tcagcaccgg ccgaattgag gtagattgcc  11280
gtgagtatct cgatgaccgg gagcgagaaa ttgctgagtc cctcccccat gctttcattg  11340
gcgacgtcaa aggcactacc gttggaggat gtcaccatgt cacctccaaa taccttccgc  11400
gcttccttcc caaggaatca gtcgcggtag tcggggtttc aagccccggg aaagccgcaa  11460
aagcagtttg cacattaaca gatgtgtatc tcccagatct cgaagcttac ctccacccag  11520
agacccagtc caagtgctgg aaaatgatgt tggacttcaa ggaagttcga ctgatggtct  11580
ggaaggacaa gacggcctat tttcaacttg aaggccgcca tttcacctgg taccagcttg  11640
caagctatgc ctcgtacatc cgagttcctg ttaactctac ggtgtatttg gacccctgca  11700
tgggccctgc cctttgcaac agaagagttg tcgggtccac tcattgggga gctgacctcg  11760
cagtcacccc ttatgattac ggtgccaaaa tcatcctgtc tagtgcatac catggtgaaa  11820
tgccccctgg gtacaaaatc ctggcgtgcg cggagttctc gcttgacgat ccagtgaggt  11880
acaaacacac ctgggggttt gaatcggata cagcgtatct gtacgagttc accggaaacg  11940
gtgaggactg ggaggattac aatgatgcgt ttcgtgcgcg ccagaaaggg aaaatttata  12000
aggccactgc caccagcatg aggtttcatt ttcccccggg ccctgtcatt gaaccaactt  12060
taggcctgaa ttgaaatgaa atggggtcca tgcaaagcct ctttgacaaa attggccaac  12120
ttttcgtgga tgctttcacg gaatttttgg tgtccattgt tgatatcatc atatttttgg  12180
ccattttgtt tggctttacc atcgctggct ggctggtggt cttctgcatc cgattggttt  12240
gctccgcggt actccgtgcg cgccctacca ttcaccctga gcaattacag aagatcctat  12300
gaggcctttc tttctcagtg ccaggtggat attcccacct ggggaactag acatcccctg  12360
gggatgcttt ggcaccataa ggtgtcaacc ctgattgatg aaatggtgtc gcgtcggatg  12420
taccgcacca tggaaaaagc aggacaggct gcctggaaac aggtggtgag cgaggccacg  12480
ctgtctcgca ttagtggttt ggatgtggtg gctcattttc agcatcttgc cgccattgaa  12540
```

-continued

```
gccgagacct gtaaatattt ggcctctcgg ctgcccatgc tacacaatct gcgcatgaca  12600
gggtcaaatg taaccatagt gtataatagt actttgaatc aggtgtttgc tatttttcca  12660
acccctggat cccggccaaa gcttcatgat tttcagcaat ggctaatagc tgtgcactcc  12720
tccatatttt cctccgttgc ggcttcttgt actctttttg ttgtgctgtg gttgcggatt  12780
ccaatgctac gtactgtttt tggtttccgc tggttagggg caatttttcc ttcgaactca  12840
cggtgaatta cacggtgtgt ccgccttgcc tcacccggca agcagccgct gaggtctacg  12900
aaccaggcag gtctctttgg tgcaggatag ggcatgaccg atgtagtgag gaagaccatg  12960
acgatctagg gttcatggtt ccgtctggcc tctccagcga aggccacttg accagtgttt  13020
acgcctggtt ggcgttcctg tccttcagct acacggccca gttccatccc gagatatttg  13080
ggatagggaa tgtgagtcaa gtttatgttg acatcaagca ccaattcatc tgcgccgttc  13140
acgacgggga gaacgccacc ttgcctcgtc atgacaatat ttcagccgta tatcagacct  13200
actaccaaca tcaagtcgac ggcggcaatt ggtttcacct agaatggctg cgcccottct  13260
tttcctcttg gttggtttta aatgtttctt ggtttctcag gcgttcgcct gcaagccatg  13320
tttcagttca agtctttcgg acatcaaaac caacacaacc gcagcatcag gctttgttgt  13380
cctccaggac atcagctgcc ttaggcatgg cgactcgtcc tctcagacga ttcgcaaaag  13440
ctctcagtgc cgcgcggcga tagggacgcc cgtgtacatc actgtcacag ccaatgtcac  13500
agatgagaat tatttacatt cttctgatct ccttatgctt tcttcttgcc ttttctatgc  13560
ttctgagatg agtgaaaagg gattcaaggt gatgtttggc aatgtgtcag gcatcgtggc  13620
tgtgtgtgtc aactttacca gctacgtcca acatgtcaag gagtttaccc aacgctcctt  13680
ggtggtcgat catgtgcggc tgctccattt catgacacct gagaccatga ggtgggcaac  13740
cgttttagcc tgttttcttg ccatcttact ggcaatttga atgttcaagt atgttgggga  13800
gatgcttgac cgcgggctgt tgctcgcgat tgctttcttt gtggtgtatc gtgccatttt  13860
gttttgctgc gctcgtcaac gccaacagca acagcagctc tcatcttcag ttaatttaca  13920
acttgacgct atgtgagctg aatggcacag attggctgaa agacaaattt gattgggcat  13980
tggagacttt tgtcatcttt cccgtgttga ctcacattgt ctcatatagt gcactcacca  14040
ctagccattt ccttgacaca gtcggtctgg ttactgtgtc tactgccggg ttctaccacg  14100
ggcggtatgt tctgagtagc atctacgcgg tctgcgctct ggccgcattg acttgcttcg  14160
tcattaggct tgcgaagaac tgcatgtcct ggcgctactc ttgtaccaga tatactaact  14220
tccttctgga cactaagggc agactctatc gctggcggtc gcccgttatc atagagaaag  14280
ggggtaaggt tgaggtcgaa ggtcacctga tcgacctcaa aagagttgtg cttgatggtt  14340
ccgtggcaac ccctttatac agagtttcag cggaacaatg ggtcgtctt tagacgactt  14400
ttgctatgat agcacggctc cacaaaaggt gcttttggcg ttttccatta cctacacgcc  14460
agtgatgata tatgctctaa aggtaagtcg cggccgactt ttagggcttc tgcacctttt  14520
gatctttctg aattgtactt ttaccttcgg gtacatgaca tgcgtgcact ttaatagcac  14580
aaataaggtc gcgctcacta tgggagcagt agttgcactt ctttgggggg tgtactcagc  14640
catagaaacc tggaagttca tcacctccag atgtcgtttg tgcttgctag gccgcaagta  14700
cattctggcc cccgcccacc acgtcgaaag tgccgcgggc tttcatccga tcgcggcaaa  14760
tgataaccac gcatttgtcg tccggcgtcc cggctccact acggttaacg gcacattggt  14820
gcccgggttg aaaagcctcg tgttgggtgg cagaaaagct gttaaacagg gagtggtaaa  14880
```

-continued

```
ccttgtcaaa tatgccaaat aacaacggca agcagcaaaa gaaaaagagg gggaatggcc  14940

agccagtcaa tcagctgtgc cagatgctgg gtaagatcat cgcccagcaa aaccagtcca  15000

gaggcaaggg accggggaag aaaattaaga ataaaaaccc ggagaagccc cattttcctc  15060

tagcgactga agatgacgtc aggcatcact tcacccctag tgagcggcaa ttgtgtctgt  15120

cgtcgatcca gactgccttt aaccagggcg ctggaacctg taccctatca gattcaggta  15180

ggataagtta cactgtggag tttagtttgc cgacgcatca tactgtgcgc ctgatccgcg  15240

tcacagcgcc atcatcagcg taatgggctg gcattcctta agcacctcag tgttagaatt  15300

ggaagaatgt gtggtgaatg gcactgattg gcactgtgcc tctaagtcac ctattcaatt  15360

agggcgaccg tgtgggggtt aagtttaatt ggcgagaacc atgcggccga aattaaaaaa  15420

aaaa                                                               15424
```

<210> SEQ ID NO 2
<211> LENGTH: 15424
<212> TYPE: DNA
<213> ORGANISM: Porcine reproductive and respiratory syndrome virus

<400> SEQUENCE: 2

```
tcgcccgggc aggtgttggc tctatgcctt ggcatttgta ttgtcaggag ctgcgaccat     60

tggtacagcc caaaactagc tgcacagaaa acgcccttct gtgacagccc tcttcagggg    120

agcttagggg tctgtcccta gcaccttgct tccggagttg cactgcttta cggtctctcc    180

aaccctttaa ccatgtctgg gatacttgat cggtgcacgt gcacccccaa tgccagggtg    240

tttatggcgg agggccaagt ctactgcaca cgatgtctca gtgcacggtc tctccttcct    300

ctgaatctcc aagttcctga gcttggagtg ctgggcctat tttacaggcc cgaagagcca    360

ctccggtgga cgttgccacg tgcattcccc actgttgagt gctcccccgc cggggcctgc    420

tggctttctg cgatctttcc aattgcacga atgaccagtg gaaacctgaa ctttcaacaa    480

agaatggtgc gggtcgcagc tgagatttac agagccggcc agctcacccc tgcagtcttg    540

aaggctctac aagtttatga acggggttgc cgctggtacc ctatagtcgg acctgtccct    600

ggagtggccg tttttgccaa ctccctacat gtgagtgata aacctttccc gggagcaact    660

catgtgctaa ccaacctgcc actcccgcag aggcctaagc ctgaagactt ttgccctttt    720

gagtgtgcta tggctgacgt ctatgatatt ggtcatggcg ccgtcatgta tgtggccaaa    780

gggaaagtct cctgggcccc tcgtggcggg gatgaggcga aatttgaaac tgtccctagg    840

gagttgaagt tgatcgcgaa ccaactccac atctccttcc cgccccacca cgcagtggac    900

atgtctaagt ttgtgttcat agcccctggg agtggtgtct ctatgcgggt cgagtgccca    960

cacggctgtc tccccgctaa tactgtccct gaaggtaact gctggtggcg cttgtttgac   1020

tcgctcccac tggacgttca gaacaaagaa attcgccgtg ccaaccaatt cggctatcaa   1080

accaagcatg gtgtcgctgg caagtaccta caacggaggc tgcaagctaa tggtctccga   1140

gcagtgactg atacagatgg acccattgtc gtacagtatt tctctgttag ggagagctgg   1200

atccgccact tcagactggc ggaagagcct agcctccctg ggtttgaaga cctcctcaga   1260

ataagggtag agcccaatac gtcgccattg agtgacaagg gtggaaaaat cttccggttt   1320

ggcagtcaca aatggtacgg tgctggaaag agagcaagga aagcacgctc tggtatgacc   1380

accacagtcg ctcaccgcgc cttgcccgct cgtgaaatcc agcaagccaa aaagcacgag   1440

gatgccggcg ctgataaggc tgtgcatctc aggcactatt ctccgcctgc cgacgggaac   1500

tgtggttggc actgcatttc cgccatcgcc aaccgaatgg tgaattccaa atttgaaact   1560
```

-continued

```
actcttcccg agagggtgag accttcagat gactgggcta ctgacgagga ccttgtgaac   1620
accatccaaa ttctcaagct ccctgcggcc ttggacagga acggtgcttg tgttggcgcc   1680
aaatacgtgc ttaagctgga aggcgagcat tggactgtct ctgtgaccct tgggatgtcc   1740
ccttctttgc tccccccttga atgtgttcag ggctgttgtg agcataagag cggacttggt   1800
cccccagatg cggtcgaagt tttcggattt gaccctgcct gccttgaccg actggctgag   1860
gtaatgcact tgcctagcag tgtcatccca gctgctctgg ccgaaatgtc cggcgacccc   1920
aactgtccgg cttccccggt cactactgtg tggactgttt cacaattctt tgcccgccac   1980
agaggaggag agcaccctga tcaggtgcgc ttaggaaaaa tcatcagcct ttgtcaagtt   2040
gttgaggaat gctgttgcca tcagaataaa accaaccggg ccaccccgga agaggttgcg   2100
gcaaggattg atcagtacct ccatggtgca acaagtcttg aagaatgctt gattaggctt   2160
gagagggttt gcccgccgag cgctgcggac accttctttg attggaatgt tgtgctccct   2220
ggggttgggg cttcaactca gacaaccaaa cagctccatg tcaaccagtg ccgcgctctg   2280
gttcctgtcg tgactcaaga gcctttggac aaagactcag tccctctgac cgccttctcg   2340
ctgtccaatt gctactatcc tgcacaaggt gacgaggttc gtcaccgtga gaggctaaac   2400
tccgtactct ctaagctgga gggggttgtt cgtgaggaat atgggctcac gccaactgaa   2460
cctggcccgc gacccgcact accgaacggg ctcgtcgaac ttaaagacca gatggaggag   2520
gatctgctga aactagtcaa cgcccaggca acttcagaaa tgatggcctg ggcagccgag   2580
caggttgatc tgaaagcttg ggtcaaaaac tacccacggt ggacaccgcc acccccctcca   2640
ccaagagttc agcctcgaaa aacaaagtct gtcaagagct tgccagggaa caaacctgtc   2700
cccgctccac gcaggaaggt cagatctgat tgtggcagcc cgattttgat gggcgacaat   2760
gttcctgacg gtcgggaaga tttgactgtt ggtggccccc ttgatctttc gacaccatcc   2820
gagccgatga cacctctgag tgagcctgca cttatgcccg cgttgcaata tatttctagg   2880
ccagtgacat ctttgagtgt gctggcccca gttcctgcac cgcgtagaac tgtgtcccga   2940
ccggtgacgc ccttgagtga gccaattttt gtgtctgcac cgcgacacaa atttcagcag   3000
gtggaagaag cgaatctggc ggcaacaacg ctgacgcacc aggacgaacc tctagatttg   3060
tctgcatcct cacagactga atatgaggct tctcccctaa caccactgca gaacatgggt   3120
attctggagg tgggggggca agaagctgag gaagttctga gtgaaatctc ggatacactg   3180
aatgacatca accctgcacc tgtgtcatca agcagctccc tgtcaagtgt taagatcaca   3240
cgcccaaaac actctgctca agccatcatt gactcgggcg ggccctgcag tgggcatctc   3300
cgaagggaaa aagaagcatg cctcagcatc atgcgtgagg cttgtgatgc ggctaagctt   3360
agtgaccctg ccacgcagga atggctttct cgcatgtggg atagggttga catgctgact   3420
tggcgcaaca cgtctgctta ccaggcgttc cgcatcttag atggtaggtt tgagtttctc   3480
ccaaagatga tactcgagac accgccgccc tacccgtgtg ggtttgtgat gctgcctcac   3540
acgcctgcac cttccgtggg tgcagagagt gaccttacca ttggttcagt cgccactgaa   3600
gatgttccac gcatcctcgg gaaaatagaa aacgccggcg agatgcccaa ccaggggctc   3660
ttgacatcct tcggggaaga accggtgtgc gaccaacctg tcaaggactc ctggatgtcg   3720
tcgcgggggt ttgacgagag cacaacggct ccgtccgctg gtacaggtgg tgctgactta   3780
cccaccgatt tgccaccttc agatggtttg gatgcggacg agtgggggcc gttacggacg   3840
gtaagaaaga aagctgaaag gctcttcgac caattgagcc gtcaggtttt taacctcgtc   3900
```

-continued

```
tcccatctcc ctgttttctt ctcacacctc ttcaaatctg acagtggtta ttctccgggt   3960
gattggggtt ttgcagcttt tactttattt tgcctctttt tgtgttacag ctacccattc   4020
tttggttttg ttcccctctt gggtgttttt tctgggtctt ctcggcgtgt gcgcatgggg   4080
gtttttggct gttggttggc ttttgctgtt ggcctgttca agcctgtgtc cgacccagtc   4140
ggcactgctt gtgagtttga ctcgccagag tgtaggaacg tccttcattc ttttgagctt   4200
ctcaaacctt gggaccctgt tcgcagcctt gttgtgggcc ccgtcggtct cggccttgcc   4260
attcttggca ggttactggg cggggcacgc tacatctggc attttttgct taggcttggc   4320
attgttgcag attgtatctt ggctggagct tatgtgcttt ctcaaggtag gtgtaaaaag   4380
tgctggggat cttgtgtaag aactgctcct aatgaaatcg ccttcaacgt gttccctttt   4440
acgcgtgcga ccaggtcgtc actcatcgac ctgtgcgatc ggttttgtgc gccaaaaggc   4500
atggacccca ttttcctcgc tactgggtgg cgcgggtgct ggaccggccg aagtcccatt   4560
gagcaaccct ctgaaaaacc catcgcgttc gcccagttgg atgaaaagag gattacggct   4620
agaactgtgg gcgctcagcc ttatgatcct aaccaagccg taaagtgctt gcgggtgtta   4680
caggcgggtg gggcgatagt ggccgaggca gtcccaaaag tggtcaaggt ttccgctatt   4740
ccattccgag ctcccttttt tcccaccgga gtgaaggttg atcctgagtg caggatcgtg   4800
gtcgaccccg acacttttac tacagctctc cggtctggtt actccaccac aaacctcgtc   4860
cttggtgtgg gggactttgc ccaactgaat ggattaaaaa tcaggcaaat ttccaagccc   4920
tcgggaggag gcccgcacct cattgctgcc ctgcatgttg cttgctcgat ggcgttgcac   4980
atgcttgctg gagtttatgt aactgcagtg gggtcttgcg gtaccggcac caacgatccg   5040
tggtgcacta acccattcgc cgtccctggc tacggacctg gctccctctg cacgtccaga   5100
ttgtgcatct cccaacatgg ccttaccctg cccttgacag cacttgtggc aggattcggt   5160
cttcaggaaa ttgccctagt cgttttgatt ttcgtttcca tcggaggcat ggctcatagg   5220
ttgagttgta aggctgatat gctgtgcgtc ttacttgcaa tcgccagcta tgtttgggta   5280
ccccttacct ggttgctctg tgtgtttcct tgctggttgc gctggttctc tttgcaccct   5340
ctcaccattc tatggttggt gtttttcttg atgtctgtaa atatgccttc gggaatctta   5400
accgtggtgt tattggttgc tctttggctt ctaggccgtt atactaatgt tgttggtctt   5460
gttaccccct atgatattca tcattacacc aatggccccc gcggtgttgc cgccttggct   5520
accgcaccag atgggactta cttggccgct gtccgccgcg ctgcgttgac tggccgcacc   5580
gtgctgttta ccccgtctca gcttgggtcc cttcttgagg gcgctttcag aactcgaaag   5640
ccctcactga acaccgtcaa tgtggtcggg tcctccatgg gctctggcgg agtgttcact   5700
atcgatggga aaattaagtg cgtgactgcc gcacatgtcc ttacgggtaa ttcagccagg   5760
gtttccgggg tcggcttcaa tcaaatgctt gactttgatg taaaagggga cttcgccata   5820
gctgattgcc cgaattggca aggggctgct cctaagaccc aattctgcga ggatggatgg   5880
actggccgcg cctattggct gacatcctct ggcgtcgaac ccggtgtcat tgggaatgga   5940
ttcgccttct gcttcaccgc gtgcggcgat tccgggtccc cagtgatcac cgaagccggt   6000
gagcttgtcg gcgttcacac aggatcaaac aaacaaggag gaggcattgt tacgcgcccc   6060
tctggccagt tttgcaatgt ggcacccatc aagctgagcg aattaagtga gttctttgct   6120
ggacctaagg tcccgctcgg tgatgtgaag gttggcagcc acataattaa agacatatgc   6180
gaggtacctt cagatctttg cgccttgctt gctgccaaac ccgaactgga aggaggcctc   6240
tccaccgtcc aacttctgtg tgtgtttttc ctcctgtgga gaatgatggg acatgcctgg   6300
```

-continued

```
acgcccttgg ttgctgttgg gttttttatc ttgaatgagg ttctcccagc tgtactggtc   6360
cggagtgttt tctcctttgg aatgtttgtg ctatcttggc tcacaccatg gtctgcgcaa   6420
gttctgatga tcaggcttct aacagcagct cttaacagga acagattgtc actcgccttt   6480
tacagccttg gtgcagcgac cggttttgtc gcagatctgg cggcaactca agggcacccg   6540
ttgcaggcag taatgaattt aagtacctat gccttcctgc ctcggataat ggtcgtgacc   6600
tcaccagtcc cagtgattgc gtgtggtgtt gtgcacctcc ttgccataat tttgtacttg   6660
tttaagtacc gctgcctgca caatgtcctt gttggcgatg gtgcgttctc tgcggctttc   6720
ttcttgcgat actttgccga ggggaaattg agggaagggg tgtcgcaatc ctgcgggatg   6780
aatcatgagt cgctgactgg tgccctcgct atgagactta atgacgagga cttggatttt   6840
cttacgaaat ggactgattt taagtgtttt gtttctgcat ccaacatgag gaatgcggcg   6900
ggccagttca tcgaggctgc ctatgctaaa gcacttagaa ttgaacttgc ccagttggtg   6960
caggttgata aggttcgagg tactttggcc aaacttgaag cttttgctga taccgtggca   7020
ccccaactct cgcccggtga cattgttgtt gctcttggcc atacgcctgt tggcggtatc   7080
ttcgacctaa aggttggtag caccaagcat accctccaag ccattgagac cagagttctt   7140
gccgggtcca aaatgaccgt ggcgcgtgtc gttgatccaa cccccacacc cccacccgca   7200
cccgtgccta tccccccttcc accgaaagtt ctggagaatg gtcccaacgc ctggggggat   7260
gaggatcgtt tgaataagaa gaagaggcgc aggatggaag ccgtcggcat ctttgttatg   7320
ggtggaaaga aatatcagaa attttgggac aagaactccg gtgatgtgtt ttatgaggag   7380
gtccatgata acacagacgc gtgggagtgc ctcagagttg acaaccctgc cgactttgac   7440
cctgagaagg gaactctgtg cgggcatact accattgaag ataagactta cagtgtctac   7500
gcctccccat ctggcaagaa attcctggtc cccgtctacc cagagagcaa aaaaaaccaa   7560
tgggaagctg cgaagctttc cgtggaacag gcccttggca tgatgaatgt cgacggtgaa   7620
ctgacagcca aagaagtgga gaaactgaaa agaataattg acaaactcca gggcctgact   7680
aaggagcagt gtttaaactg ctagccgcca gcggcttgac ccgctgtggt cgcggcggct   7740
tggttgttac tgagacagcg gtaaaaatag tcaaatttca caaccggacc ttcaccctag   7800
gacctgtgaa tttaaaagtg gccagtgagg ttgagctaaa agacgcggtc gagcataacc   7860
aacacccggt tgcaagaccg gttgatggtg gtgttgtgct cctgcgctcc gcagttcctt   7920
cgcttataga cgtcttaatc tccggcgctg atgcatctcc caagttactc gcccgccacg   7980
ggccgggaaa cactgggatc gatggcacgc tttgggattt tgaggccgag gccactaaag   8040
aggaaattgc actcagtgcg caaataatac aggcttgtga cattaggcgc ggcgacgcac   8100
ctgaaattgg tcttccttat aagctgtacc ctgtcagggg caaccctgag cgggtaaaag   8160
gagttttaca gaatacaagg tttggagaca taccttataa aacccccagt gacactggaa   8220
gcccagtgca cgcggctgcc tgcctcacgc ccaatgccac tccggtgact gatgggcgct   8280
ccgtcttggc cacgactatg ccctccggtt ttgagttgta tgtaccgacc attccagcgt   8340
ctgtccttga ttatcttgat tctaggcctg actgccccaa acagttgaca gagcacggct   8400
gtgaggacgc cgcattaaga gacctctcca agtatgactt gtccacccaa ggctttgttt   8460
tacctggagt tcttcgcctt gtgcgtaagt acctgtttgc tcatgtgggt aagtgcccgc   8520
ccgttcatcg gccttccact taccctgcca agaattctat ggctggaata aatgggaaca   8580
ggtttccaac caaggacatc cagagcgtcc ctgaaatcga cgttctgtgc gcacaggccg   8640
```

-continued

```
tgcgggaaaa ctggcaaact gttacccctt gtaccctcaa gaaacagtat tgtgggaaga   8700
agaagactag gacaatactc ggcaccaata acttcattgc gctggcccac cgggcagcgt   8760
tgagtggtgt cacccagggc ttcatgaaaa aggcgtttaa ctcgcccatt gccctcggta   8820
aaaacaaatt taaagagctt cagactccgg tcttaggcag gtgccttgaa gctgatcttg   8880
catcctgcga tcgctccaca cctgcaattg tccgctggtt tgccgccaat cttctttatg   8940
aacttgcctg tgctgaagag cacctgccgt cgtacgtgtt gaactgctgc cacgacctac   9000
tggtcacgca gtccggcgca gtaactaaga gaggtggcct gtcgtctggc gacccgatca   9060
cttctgtgtc caacaccatt tacagcttgg tgatatatgc acaacacatg gtgctcagtt   9120
actttaaaag tggtcaccct catggccttc tgtttctaca agaccagctg aagtttgagg   9180
acatgctcaa ggttcaaccc ctgatcgtct attcggacga cctcgtactg tatgccgagt   9240
ctcccaccat gccaaactac cactggtggg ttgaacatct gaacctgatg ctgggttttc   9300
agacggaccc aaagaagaca gccataacag actcgccatc atttctaggc tgtaggataa   9360
taaatggacg ccagctcgtc cctaaccgtg acaggattct cgcggccctc gcctaccata   9420
tgaaggcaag caatgtctct gaatactacg cctcggcggc tgcgatactc atggacagct   9480
gtgcttgttt agagtatgat cccgaatggt ttgaagagct tgtagttggg atagcgcagt   9540
gtgcccgcaa ggacggctac agttttcccg gcccgccgtt cttcttgtcc atgtgggaaa   9600
aactcagatc caatcatgag ggaagaagt ccagaatgtg cgggtactgc ggggccccgg   9660
ctccgtacgc cactgcctgt ggcctcgacg tctgtattta ccacacccac ttccaccagc   9720
attgtccagt catcatctgg tgtggccacc cggctggttc tggttcttgt agtgagtgca   9780
aacccccccct agggaaaggc acaagccctc tagatgaggt gttagaacaa gtcccgtata   9840
agcctccacg gactgtaatc atgcatgtgg agcagggtct caccccctctt gacccaggca   9900
gataccagac tcgccgcgga ttagtctccg ttaggcgtgg cattagagga aatgaggttg   9960
atctaccaga cggtgattat gctagcaccg ccctactccc tacttgtaaa gagattaaca  10020
tggtcgctgt cgcctctaat gtgttgcgca gcaggttcat catcggcccg cctggtgctg  10080
ggaaaacata ctggctcctt caacaggtcc aggatggtga tgtcatttac acgccaactc  10140
accagaccat gctcgatatg attagggctt tggggacgtg ccggttcaac gtcccagcag  10200
gtacgacgct gcaattccct gccccctccc gtaccggccc ttgggttcgc atcctagccg  10260
gcggttggtg tcctggcaag aattccttcc tggatgaagc agcgtattgt aatcaccttg  10320
atgtcttgag gcttcttagc aaaactaccc tcacctgtct gggagatttc aaacaactcc  10380
acccagtggg ttttgattct cattgctatg tttttgacat catgcctcag actcaactga  10440
agaccatctg gagatttgga cagaatatct gtgatgccat tcagccagat tacagggaca  10500
aacttgtatc catggtcaac acaacccgtg taacctacgt ggaaaaacct gtcaagtatg  10560
ggcaagtcct cacccccttac cacagggacc gagaggacgg cgccatcaca attgactcca  10620
gtcaaggcgc cacatttgat gtggttacac tgcatttgcc cactaaagat tcactcaaca  10680
ggcaaagagc ccttgttgct attaccaggg caagacatgc tatctttgtg tatgacccac  10740
acaggcaact gcagagcatg tttgatcttc ctgcgaaagg cacacccgtc aacctcgctg  10800
tgcaccgtga cgagcagctg atcgtgctag atagaaataa caaagaatgc acggttgctc  10860
aggctctagg caatggggat aaattcaggg ccacagacaa gcgcgttgta gattctctcc  10920
gcgccatttg tgcagatctg gaagggtcga gctccccgct ccccaaggtc gcacacaact  10980
tgggatttta tttctcgcct gatttgacac agtttgctaa actcccggta gaacttgcac  11040
```

-continued cccactggcc cgtggtgaca acccagaaca atgaaaagtg gccagaccgg ttggttgcta 11100
gccttcgccc cgtccataag tatagccgcg cgtgcatcgg tgccggctac atggtgggcc 11160
cctcagtgtt tctgggcacc cctggggttg tgtcatacta tctcacaaaa tttgtcaggg 11220
gcgaggctca aatgcttccg gagacagtct tcagcaccgg ccgaattgag gtagattgcc 11280
gtgagtatct tgatgaccgg gagcgagaaa ttgctgagtc cctcccccat gctttcattg 11340
gcgacgtcaa aggcactacc gttggaggat gtcaccatgt cacctccaaa taccttccgc 11400
gcttccttcc caaggaatca gtcgcggtag tcggggtttc aagccccggg aaagccgcaa 11460
aagcagtttg cacattaaca gatgtgtatc tcccagatct cgaagcttac ctccacccag 11520
agacccagtc caagtgctgg aaaatgatgt tggacttcaa ggaagttcga ctgatggtct 11580
ggaaggacaa gacggcctat tttcaacttg aaggccgcca tttcacctgg taccagcttg 11640
caagctatgc ctcgtacatc cgagttcctg ttaactctac ggtgtatttg gacccctgca 11700
tgggccctgc cctttgcaac agaagagttg tcgggtccac tcattgggga gctgacctcg 11760
cagtcacccc ttatgattac ggtgccaaaa tcatcctgtc tagtgcatac catggtgaaa 11820
tgcccccctgg gtacaaaatc ctggcgtgcg cggagttctc gcttgacgat ccagtgaggt 11880
acaaacacac ctggggggttt gaatcggata cagcgtatct gtacgagttc accggaaacg 11940
gtgaggactg ggaggattac aatgatgcgt ttcgtgcgcg ccagaaaggg aaaatttata 12000
aggccactgc caccagcatg aggtttcatt ttcccccggg ccctgtcatt gaaccaactt 12060
taggcctgaa ttgaaatgaa atggggtcca tgcaaagcct ctttgacaaa attggccaac 12120
tttttgtgga tgctttcacg gaatttttgg tgtccattgt tgatatcatc atatttttgg 12180
ccattttgtt tggctttacc atcgctggct ggctggtggt cttctgcatc cgattggttt 12240
gctccgcggt actccgtgcg cgccctacca ttcaccctga gcaattacag aagatcctat 12300
gaggcctttc tttctcagtg ccaggtggat attcccacct ggggaactag acatcccctg 12360
gggatgtttt ggcaccataa ggtgtcaacc ctgattgatg aaatggtgtc gcgtcggatg 12420
taccgcacca tggaaaaagc aggacaggct gcctggaaac aggtggtgag cgaggccacg 12480
ctgtctcgca ttagtggttt ggatgtggtg gctcattttc agcatcttgc cgccattgaa 12540
gccgagacct gtaaatattt ggcctctcgg ctgcccatgc tacacaatct gcgcatgaca 12600
gggtcaaatg taaccatagt gtataatagt actttgaatc aggtgtttgc tatttttcca 12660
acccctggat cccggccaaa gcttcatgat tttcagcaat ggctaatagc tgtgcactcc 12720
tccatatttt cctccgttgc ggcttcttgt actcttttg ttgtgctgtg gttgcggatt 12780
ccaatactac gtactgtttt tggtttccgc tggttagggg caatttttcc ttcgaactca 12840
cggtgaatta cacggtgtgt ccgccttgcc tcacccggca agcagccgct gaggtctacg 12900
aaccaggcag gtctctttgg tgcaggatag ggcatgaccg atgtagtgag gacgaccatg 12960
acgatctagg gttcatggtt ccgcctggcc tctccagcga aggccacttg accagtgttt 13020
acgcctggtt ggcgttcctg tccttcagct acacggccca gttccatccc gagatatttg 13080
ggatagggaa tgtgagtcaa gtttatgttg acatcaagca ccaattcatc tgcgccgttc 13140
acgacgggga gaacgccacc ttgcctcgtc atgacaatat ttcagccgta tttcagacct 13200
actaccaaca tcaagtcgac ggcggcaatt ggtttcacct agaatggctg cgccccttct 13260
tttcctcttg gttggtttta aatgtttctt ggtttctcag gcgttcgcct gcaagccatg 13320
tttcagttca agtctttcgg acatcaaaac caacactacc gcagcatcag gctttgttgt 13380

-continued cctccaggac atcagctgcc ttaggcatgg cgactcgtcc tctcagacga ttcgcaaaag 13440
ctctcagtgc cgcgcggcga tagggacgcc cgtgtacatc actgtcacag ccaatgtcac 13500
agatgagaat tatttacatt cttctgatct ccttatgctt tcttcttgcc ttttctatgc 13560
ttctgagatg agtgaaaagg gattcaaggt gatatttggc aatgtgtcag gcatcgtggc 13620
tgtgtgtgtc aactttacca gctacgtcca acatgtcaag gagtttaccc aacgctcctt 13680
ggtggtcgat catgtgcggc tgctccattt catgacacct gagaccatga ggtgggcaac 13740
cgttttagcc tgttttttg ccatcttact ggcaatttga atgttcaagt atgttgggga 13800
gatgcttgac cgcgggctgt tgctcgcgat tgctttcttt gtggtgtatc gtgccatttt 13860
gttttgctgc gctcgtcaac gccaacagca acagcagctc tcatcttcag ttgatttaca 13920
acttgacgct atgtgagctg aatggcacag attggctgaa agacaaattt gattgggcag 13980
tggagacttt tgtcatcttt cccgtgttga ctcacattgt ctcatatggt gcactcacca 14040
ctagccattt ccttgacaca gtcggtctgg ttactgtgtc taccgccggg ttctaccacg 14100
ggcggtatgt tctgagtagc atctacgcgg tctgcgctct ggccgcattg atttgcttcg 14160
tcattaggct tgcgaagaac tgcatgtcct ggcgctactc ttgtaccaga tatactaact 14220
tccttctgga cactaagggc agactctatc gctggcggtc gcccgttatc atagagaaag 14280 gggtaaggt tgaggtcgaa ggtcacctga tcgacctcaa aagagttgtg cttgatggtt 14340
ccgtggcaac ccctttaacc agagtttcag cggaacaatg ggtcgtcctt tagacgactt 14400
ttgctatgat agcacggctc cacaaaaggt gcttttggcg ttttccatta cctacacgcc 14460
agtgatgata tatgctctaa aggtaagtcg cggccgactt ttagggcttc tgcacctttt 14520
gatctttctg aattgtactt ttaccttcgg gtacatgaca ttcgtgcact ttaatagcac 14580
aaataaggtc gcgctcacta tgggagcagt agttgcactt ctttgggggg tgtactcagc 14640
catagaaacc tggaagttca tcacctccag atgccgtttg tgcttgctag gccgcaagta 14700
cattctggcc cccgcccacc acgtcgaaag tgccgcgggc tttcatccga tcgcggcaaa 14760
tgataaccac gcatttgtcg tccggcgtcc cggctccact acggttaacg gcacattggt 14820
gcccgggttg aaaagcctcg tgttgggtgg cagaaaagct gttaaacagg gagtggtaaa 14880
ccttgtcaaa tatgccaaat aacaacggca agcagcaaaa gaaaaagagg gggaatggcc 14940
agccagtcaa tcagctgtgc cagatgctgg gtaagatcat cgcccagcaa aaccagtcca 15000
gaggcaaggg accggggaag aaaattaaga ataaaaaccc ggagaagccc cattttcctc 15060
tagcgactga agatgacgtc aggcatcact tcacccctag tgagcggcaa ttgtgtctgt 15120
cgtcgatcca gactgccttt aaccagggcg ctggaacctg taccctatca gattcaggta 15180
ggataagtta cactgtggag tttagtttgc cgacgcatca tactgtgcgc ctgatccgcg 15240
tcacagcgcc atcatcagcg taatgggctg gcattcctta agcacctcag tgttagaatt 15300
ggaagaatgt gtggtgaatg gcactgattg gcactgtgcc tctaagtcac ctattcaatt 15360
agggcgaccg tgtgggggtt aagtttaatt ggcgagaacc atgcggccga aattaaaaaa 15420
aaaa 15424

<210> SEQ ID NO 3
<211> LENGTH: 15413
<212> TYPE: RNA
<213> ORGANISM: Porcine reproductive and respiratory syndrome virus

<400> SEQUENCE: 3
augacguaua gguguuggcu cuaugccuug gcauuuguau ugucaggagc ugcgaccauu 60

-continued

```
ggcacagccc aaaacuagcu gcacagaaaa cgcccuucug ugacagcccu cuucagggga    120
gcuuaggggu cugucccuag caccuugcuu ccggaguugc acugcuuuac ggucucucca    180
acccuuuaac caugucuggg auacuugauc ggugcacgug cacccccaau gccagggugu    240
uuauggcgga gggccaaguc uacugcacac gaugucucag ugcacggucu cuccuuccuc    300
ugaaucucca aguuccugag cuuggagugc ugggccuauu uuacaggccc gaagagccac    360
uccgguggac guugccacgu gcauucccca cuguugagug cucccccgcc ggggccugcu    420
ggcuuucugc gaucuuucca auugcacgaa ugaccagugg aaaccugaac uuucaacaaa    480
gaauggugcg ggucgcagcu gagauuuaca gagccggcca gcucaccccu gcagucuuga    540
aggcucuaca aguuuaugaa cgggguugcc gcugguaccc uauagucgga ccugucccug    600
gaguggccga uuuugccaac ucccuacaug ugagugauaa accuuucccg ggagcaacuc    660
augugcuaac caaccugcca cucccagaga ggccuaagcc ugaagacuuu ugcccuucug    720
agugugcuau ggcugacguc uaugauauug gccauggcgc cgucauguau guggccaaag    780
ggaaagucuc cugggccccu cguggcgggg augaggcgaa auuugaaccu gucccuaggg    840
aguugaaguu gaucgcgaac caacuccaca ucuccuuccc gccccaccac gcaguggaca    900
ugucuaaguu uguguucaua gccccuggga guggugucuc uaugcggguc gagugcccac    960
acggcugucu ccccgcuaau acugucccug aagguaacug cugguggcgc uuguuugacu   1020
cgcucccacu ggacguucag aacaaagaaa uucgccgugc caaccaauuc ggcuaucaaa   1080
ccaagcaugg ugucgcuggc aaguaccuac aacggaggcu gcaagcuaau ggucuccgag   1140
cagugacuga uacagaugga cccauugucg uacaguauuu cucuguuagg gagagcugga   1200
uccgccacuu cagacuggcg gaagagccua gccucccugg guuugaagac cuccucagaa   1260
uaaggguaga gcccaauacg ucgccauuga gugacaaggg uggaaaaauc uuccgguuug   1320
gcagucacaa augguacggu gcuggaaaga gagcaaggaa agcacgcucu gguaugacca   1380
ccacagucgc ucaccgcgcc uugcccgcuc gugaaaucca gcaagccaaa aagcacgagg   1440
augccggcgc ugauaaggcu gugcaucuca ggcacuauuc uccgccugcc gacgggaacu   1500
gugguuggca cugcauuucc gccaucgcca accgaauggu gaauuccaaa uuugaaacua   1560
cucuucccga gagggugaga ccuucagaug acugggcuac ugacgaggac cuugugaaca   1620
ccauccaaau ucucaagcuc ccugcggccu uggacaggaa cggugcuugu guuggcgcca   1680
aauacgugcu uaagcuggaa ggcgagcauu ggacugucuc ugugacccuu gggauguccc   1740
cuucuuugcu cccccuugaa uguguucagg gcuguuguga gcauaagagc ggacuugguc   1800
ccccagaugc ggucgaaguu uucggauuug acccugccug ccuugaccga cuggcugagg   1860
uaaugcacuu gccuagcagu gucaucccag cugcucuggc cgaaaugucc ggcgacccca   1920
accguccggc uuccccgguc acuacugugu ggacuguuuc acaauucuuu gcccgccaca   1980
gaggaggaga gcacccugau caggugcgcu uaggaaaaau caucagccuu ugucaaguug   2040
uugaggaaug cuguugccau cagaauaaaa ccaaccgggc caccccggaa gagguugcgg   2100
caaggauuga ucaguaccuc cauggugcaa caagucuuga agaaugcuug auuaggcuug   2160
agaggguuug cccgccgagc gcugcggaca ccuucuuuga uuggaauguu gugcuccug    2220
ggguuggggc uucaacucag acaaccaaac agcuccaugu caaccagugc cgcgcucugg   2280
uuccugucgu gacucaagag ccuuuggaca aagacccagu cccucugacc gccuucucgc   2340
uguccaauug cuacuauccu gcacaaggug acgagguucg ucaccgugag aggcuaaacu   2400
```

-continued

```
ccguacucuc uaagcuggag gggguuguuc gugaggaaua ugggcucacg ccaacuggac   2460
cuggcccgcg acccgcacua ccgaacgggc ucgucgaacu uaaagaccag auggaggagg   2520
aucugcuaaa acuagucaac gcccaggcaa cuucagaaau gauggccugg gcagccgagc   2580
agguugaucu gaaagcuugg gucaaaaacu acccacggug gacaccguca cccccuccac   2640
caagaguuca gccucgaaaa acaaagccug ucaagagcuu gccagggaac aaaccugucc   2700
ccgcuccacg caggaagguc agaucugauu guggcagccc gauuucgaug ggcgacaaug   2760
uuccugacgg ucgggaagau uugacuguug guggcccccu ugaucuuucg acaccauccg   2820
agccgaugac accucugagu gagccugcac cuaugcccgc guugcaauau auuucuaggc   2880
cagugacacc uuugagugug cuggccccag uaccugcacc gcguagaacu gugucccgac   2940
cggugacgcc cuugagugag ccaauuuuug ugucugcacc gcgacacaaa uuucagcagg   3000
uggaagaagc gaaucuggcg gcaacaaugc ugacgcacca ggacgaaccu cuagauuugu   3060
cugcauccuc acagacugaa uaugaggcuu cuccccuaac accacugcag aacaugggua   3120
uucuggaggu gggggggcaa gaagcugagg aaguucugag ugaaaacucg gauacacuga   3180
augacaucaa cccugcaccu gugucaucaa gcagcucccu gucaaguguu aagaucacac   3240
gcccaaaaca cucugcucaa gccaucauug acucgggcgg gcccugcagu gggcaucucc   3300
gaaagggaaa agaagcaugc cucagcauca ugcgugaggc uugugaugcg gcuaagcuua   3360
gugacccugc cacgcaggaa uggcuuucuc gcauguggga uaggguugau augcugacuu   3420
ggcgcaacac gucugcuuac caggcguucc gcaucuuaga ugguagguuu gaguuucucc   3480
caaagaugau acucgagaca ccgccgcccu acccgugugg guuugugaug cugccucgca   3540
cgccugcacc uuccgugggu gcagagagug accuuaccau ugguucaguc gccacugaag   3600
auguuccacg cauccucggg aaaauagaaa acgccggcaa gaugcccaac caggggcucu   3660
ugacauccuu cggggaagaa ccggugugcg accaaccugu caaggacucc uggaugucgu   3720
cgcgggggguu ugacgagagc acaacggcuc cguccgcugg uacagguggu gcugacuuac   3780
ccaccgauuu gccaccuuca gaugguuugg augcggacga gugggggccg uuacggacgg   3840
uaagaaagaa agcugaaagg cucuucgacc aauugagccg ucagguuuuu aaccucgucu   3900
cccaucuccc uguuuucuuc ucacaccucu ucaaaucuga caguggguau ucuccgggug   3960
auuggggguuu ugcagcuuuu acuuuauuuu gccucuuuuu guguuacagc uacccauucu   4020
uugguuuugu uccccucuug gguguuuuuu cugggucuuc ucggcgugug cgcauggggg   4080
uuuuuggcug uugguuggcu uuugcuguug gccuguucaa gccugugucc gacccagucg   4140
gcacugcuug ugaguuugac ucgccagagu guaggaacgu ccuucauucu uuugagcuuc   4200
ucaaaccuug ggacccuguu cgcagccuug uugugggccc cgucggucuc ggccuugcca   4260
uucuuggcag guuacugggc ggggcacgcu acaucuggca uuuuuugcuu aggcuuggca   4320
uuguugcaga uuguaucuug gcuggagcuu augugcuuuc ucaagguagg uguaaaaagu   4380
gcuggggauc uuguguaaga acugcuccua augaaaucgc cuucaacgug uucccuuuua   4440
cgcgugcgac caggucguca cucaucgacc ugugcgaucg guuuugugcg ccaaaaggca   4500
uggaccccau uuuccucgcu acuggguggc gcgggugcug gaacggccga agucccauug   4560
agcaacccuc ugaaaaaccc aucgcguucg cccaguugga ugaaaagagg aucacggcua   4620
gaacugugggu cgcucagccu uaugauccua accaagccgu aaagugcuug cggguguuac   4680
aggcgggugg ggcgauagug gccgaggcag ucccaaaagu ggucaagguu uccgcuauuc   4740
cauuccgagc ucccuuuuuu cccaccggag ugaagguuga uccugagugc aggaucgugg   4800
```

-continued

```
ucgaccccga cacuuuuacu acagcucucc ggucugguua cuccaccaca aaccucgucc   4860
uuggguguagg ggacuuugcc caacugaaug gauuaaaaau caggcaaauu uccaagcccu   4920
cgggaggagg cccgcaccuc auugcugccc ugcauguugc uugcucgaug gcguugcaca   4980
ugcuugcugg aguuuaugua acugcagugg ggucuugcgg uaccggcacc aacgauccgu   5040
ggugcacuaa cccauucgcc gucccuggcu acggaccugg cucccucugc acguccagau   5100
ugugcaucuc ccaacauggc cuuacccugc ccuugacagc acuuguggca ggauucgguc   5160
uucaggaaau ugcccuaguc guuuugauuu ucguuuccau cggaggcaug gcucauaggu   5220
ugaguuguaa ggcugauaug cugugcgucu uacuugcaau cgccagcuau guuuggguac   5280
cccuuaccug guugcucugu guguuuccuu gcugguugcg cugguucucu uugcacccuc   5340
ucaccauucu augguuggug uuuuucuuga ugucuguaaa uaugccuucg ggaaucuuaa   5400
ccgugguguu auugguugcu cuuuggcuuc uaggccguua uacuaauguu guuggucuug   5460
uuacccccua ugauauucac cauuacacca auggcccccg cgguguugcc gccuuggcua   5520
ccgcaccaga ugggacuuac uuggccgcug uccgccgcgc ugcguugacu ggccgcaccg   5580
ugcuguuuac cccgucucag cuugggucce uucuugaggg cgcuuucaga acucgaaagc   5640
ccucacugaa caccgucaau gugguucgggu ccuccauggg cucuggcgga guguucacua   5700
ucgaugggaa aauuaagugc gugacugccg cacauguccu uacggguaau ucagccaggg   5760
uuuccggggu cggcuuuaau caaaugcuug acuuugaugu aaaaggggac uucgccauag   5820
cugacugccc gaauuggcaa ggggcugcuc cuaagaccca auucugcgag gauggaugga   5880
cuggccgcgc cuauuggcug acauccucug gcgucgaacc cggugucauu gggaauggau   5940
ucgccuucug cuucaccgcg ugcggcgauu ccgggucccc agugaucacc gaagccggug   6000
agcuugucgg cguucacaca ggaucaaaca aacaaggagg aggcauuguu acgcgccccu   6060
cuggccaguu uugcaaugug gcacccauca agcugagcga auuaagugag uucuuugcug   6120
gaccuaaggu cccgcucggu gaugugaagg uuggcagcca cauaauuaaa gacauaugcg   6180
agguaccuuc agaucuuugc gccuugcuug cugccaaacc cgaacuggaa ggaggccucu   6240
ccaccgucca acuucugugu guguuuuucc uccuguggag aaugauggga caugccugga   6300
cgcccuuggu ugcuguuggg uuuuuuaucu ugaaugaggu ucucccagcu guacuggucc   6360
ggaguguuuu cuccuuugga auguuugugc uaucuuggcu cacaccaugg ucugcgcaag   6420
uucugaugau caggcuucua acagcagcuc uuaacaggaa cagauuguca cucgccuuuu   6480
acagccuugg ugcagcgacc gguuuugucg cagaucuggc ggcaacucaa gggcacccgu   6540
ugcaggcagu aaugaauuua aguaccuaug ccuuccugcc ucggauaaug gucgugaccu   6600
caccaguccc agugauugcg uguggugaug ugcaccuccu ugccauaauu uuguacuugu   6660
uuaaguaccg cugccugcac aauguccuug uuggcgaugg ugcguucucu gcggcuuucu   6720
ucuugcgaua cuuugccgag gggaaauuga gggaaggggu gucgcaaucc ugcgggauga   6780
aucaugaguc gcugacuggu gccccucgcua ugagacuuaa ugacgaggac uuggauuuuc   6840
uuacgaaaug gacugauuuu aaguguuuug uuucugcauc caacaugagg aaugcggcgg   6900
gccaguucau cgaggcugcc uaugcuaaag cacuuagaau ugaacuugcc caguuggugc   6960
agguugauaa gguucgaggu acuuuggcca aacuugaagc uuuugcugau accguggcac   7020
cccaacucuc gcccggugac auuguuguug cucuuggcca uacgccuguu ggcgguaucu   7080
ucgaccuaaa gguugguagc accaagcaua cccuccaagc cauugagacc agaguucuug   7140
```

-continued

```
ccggguccaa aaugaccgug gcgcgugucg uugauccaac ccccacaccc ccacccgcac   7200
ccgugccuau cccccuucca ccgaaaguuc uggagaaugg ucccaacgcc ugggggggaug   7260
aggaucguuu gaauaagaag aagaggcgca agauggaagc cgucggcauc uuuguuaugg   7320
guggaaagaa auaucagaaa uuuugggaca agaacuccgg ugauguguuu uaugaggagg   7380
uccaugauaa cacagacgcg ugggagugcc ucagaguuga caacccugcc gacuuugacc   7440
cugagaaggg aacucugugc gggcauacua ccauugaaga uaagacuuac agugucuacg   7500
ccuccccauc uggcaagaaa uuccuggucc ccgccuaccc agagagcaaa aaaaaccaau   7560
gggaagcugc gaagcuuucc guggaacagg cccuuggcau gaugaauguc gacggugaac   7620
ugacagccaa agaaguggag aaacugaaaa gaauaauuga caaacuccag ggccugacua   7680
aggagcagug uuuaaacugc uagccgccag cggcuugacc cgcugugguc gcggcggcuu   7740
gguuauuacu gagacagcgg uaaaaauagu caaauuucac aaccggaccu ucacccuagg   7800
accugugaau uuaaaagugg ccagugaggu ugagcuaaaa gacgcggucg agcauaacca   7860
acacccgguu gcaagaccgg uugauggugg uguugugcuc cugcgcuccg caguuccuuc   7920
gcuuauagac gucuuaaucu ccggcgcuga ugcaucuccc aaguuacucg cccgccacgg   7980
gccgggaaac acugggaucg auggcacgcu uugggauuuu gaggccgagg ccacuaaaga   8040
ggaaauugca cucagugcgc aaauaauaca ggcuugugac auuaggcgcg gcgacgcacc   8100
ugaaauuggu cuuccuuaua agcuguaccc ugucaggggc aacccugagc ggguaaaagg   8160
aguuuuacag aauacaaggu uuggagauau accuuauaaa acccccagug acacuggaag   8220
cccagugcac gcggcugccu gccucacgcc caaugccacu ccggugacug augggcgcuc   8280
cgucuuggcc acgacuaugc ccuccgguuu ugaguuguau guaccgacca uuccagcguc   8340
uguccuugau uaucuugauu cuaggccuga cugccccaaa caguugacag agcacggcug   8400
ugaggacgcc gcauuaagag accucuccaa guaugacuug uccacccaag gcuuuguuuu   8460
accuggaguu cuucgccuug ugcguaagua ccuguuugcu cauguggua agugcccgcc   8520
cguucaucgg ccuuccacuu acccugccaa gaauucuaug gcuggaauaa augggaacag   8580
guuuccaacc aaggacaucc agagcguccc ugaaaucgac guucugugcg cacaggccgu   8640
ucgggaaaac uggcaaacug uuaccccuug uacccucaag aaacaguauu gugggaagaa   8700
gaagacuagg acaauacucg gcaccaauaa cuucauugcg cuggcucacc gggcagcguu   8760
gaguggguguc acccagggcu ucaugaaaaa ggcguuuaac ucgcccauug cccucgguaa   8820
aaacaaauuu aaagagcuuc agacuccggu cuuaggcagg ugccuugaag cugaucuugc   8880
auccugcgau cgcuccacac cugcaauugu ccgcugguuu gccgccaauc uucuuuauga   8940
acuugccugu gcugaagagc accagccguc guacguguug aacugcugcc acgaccuacu   9000
ggucacgcag uccggcgcag uaacuaagag agguggccug ucgucuggcg acccgaucac   9060
uucuguguccc aacaccauuu acagcuuggu gauauaugca caacacaugg ugcucaguua   9120
cuuuaaaagu ggucacccuc auggccuucu guuucuacaa gaccagcuga aguuugagga   9180
caugcucaag guucaacccc ugaucgucua uucggacgac cucguacugu augccgaguc   9240
ucccaccaug ccaaacuacc acugguggguu ugaacaucug aaccugaugc uggguuuuca   9300
gacggaccca aagaagacag ccauaacaga cucgccauca uuucuaggcu guaggauaau   9360
aaauggacgc cagcucgucc cuaaccguga caggauucuc gcggcccucg ccuaccauau   9420
gaaggcaagc aaugucucug aauacuacgc cucggcggcu gcgauacuca uggacagcug   9480
ugcuuguuua gaguaugauc ccgaaugguu ugaagagcuu guaguuggga uagcgcagug   9540
```

-continued

```
ugcccgcaag gacggcuaca guuuucccgg cccgccguuc uucuugucca ugugggaaaa   9600
acucagaucc aaucaugagg ggaagaaguc cagaaugugc ggguacugcg gggccccggc   9660
uccguacgcc acugccugug gccucgacgu cuguauuuac cacacccacu uccaccagca   9720
uuguccaguc aucaucuggu guggccaccc ggcugguucu gguucuugua gugagugcaa   9780
acccccccua gggaaaggca caagcccucu agaugaggug uuagaacaag ucccguauaa   9840
gccuccacgg acuguaauca ugcaugugga gcagggucuc accccucuug acccaggcag   9900
auaccagacu cgccgcggau uagucuccgu uaggcguggc auuagaggaa augagguuga   9960
ucuaccagac ggugauuaug cuagcaccgc ccuacucccu acuuguaaag agauuaacau  10020
ggucgcuguc gccucuaaug uguugcgcag cagguucauc aucggcccgc cuggugcugg  10080
gaaaacauac uggcuccuuc aacaggucca ggauggugau gccauuuaca cgccaacuca  10140
ccagaccaug cucgauauga uuagggcuuu ggggacgugc cgguucaacg ucccagcagg  10200
uacgacgcug caauucccug cccccucccg uaccggcccu uggguucgca uccuagccgg  10260
cgguuggugu ccuggcaaga auuccuuccu ggaugaagca gcguauugua aucaccuuga  10320
ugucuugagg cuucuuagca aaacuacccu caccugucug ggagauuuca aacaacucca  10380
cccaguggu uuugauucuc auugcuaugu uuuugacauc augccucaga cucaacugaa  10440
gaccaucugg agauuuggac agaauaucug ugaggccauu cagccagauu acagggacaa  10500
acuuguaucc auggucaaca caacccgugu aaccuacgug gaaaaaccug ucaaguaugg  10560
gcaaguccuc accccuuacc acagggaccg agaggacggc gccaucacaa uugacuccag  10620
ucaaggcgcc acauuugaug ugguuacacu gcauuugccc acuaaagauu cacucaacag  10680
gcaaagagcc cuuguugcua uuaccagggc aagacaugcu gucuuugugu augacccaca  10740
caggcaacug cagagcaugu uugaucuucc ugcgaaaggc acacccguca accucgcugu  10800
gcaccgugac gagcagcuga ucgugcuaga uagaaauaac aaagaaugca cgguugcuca  10860
ggcucuaggc aauggggaua aauucagggc cacagacaag cgcguuguag auucucuccg  10920
cgccauuugu gcagaucugg aagggucgag cucccccgcuc cccaaggucg cacacaacuu  10980
gggauuuuau uucucgccug auuugacaca guuugcuaaa cucccgguag aacuugcacc  11040
ccacuggccc guggugacaa cccagaacaa ugaaaagugg ccagaccggu ugguugcuag  11100
ccuucgcccc guccauaagu auagccgcgc gugcaucggu gccggcuaca uggugggccc  11160
cucaguguuu cugggcaccc cuggggugu gucauacuau cucacaaaau uugucagggg  11220
cgaggcucaa augcuuccgg agacagucuu cagcaccggc cgaauugagg uagauugccg  11280
ugaguaucuc gaugaccggg agcgagaaau ugcugagucc cucccccaug cuuucauugg  11340
cgacgucaaa ggcacuaccg uuggaggaug ucaccauguc accuccaaau accuuccgcg  11400
cuuccuuccc aaggaaucag ucgcgguagu cggggguuuca agccccggga aagccgcaaa  11460
agcaguuugc acauuaacag auguguaucu cccagaucuc gaagcuuacc uccacccaga  11520
gacccagucc aagugcugga aaaugauguu ggacuucaag gaaguucgac ugauggucug  11580
gaaggacaag acggccuauu uucaacuuga aggccgccau uucaccuggu accagcuugc  11640
aagcuaugcc ucguacaucc gaguuccugu uaacucuacg guguauuugg accccugcau  11700
gggcccugcc cuuugcaaca gaagaguugu cggguccacu cauuggggag cugaccucgc  11760
agucaccccu uaugauuacg gugccaaaau cauccugucu agugcauacc auggugaaau  11820
gcccccuggg uacaaaaucc uggcgugcgc ggaguucucg cuugacgauc cagugaggua  11880
```

-continued

```
caaacacacc ugggggguuug aaucggauac agcguaucug uacgaguuca ccggaaacgg  11940
ugaggacugg gaggauuaca augaugcguu ucgugcgcgc cagaaaggga aaauuuauaa  12000
ggccacugcc accagcauga gguuucauuu ucccccgggc ccugucauug aaccaacuuu  12060
aggccugaau ugaaaugaaa uggggguccau gcaaagccuc uuugacaaaa uuggccaacu  12120
uuucguggau gcuuucacgg aauuuuuggu guccauuguu gauaucauca uauuuuuggc  12180
cauuuuguuu ggcuuuacca ucgcuggcug gcuggugguc uucugcaucc gauugguuug  12240
cuccgcggua cuccgugcgc gcccuaccau ucacccugag caauuacaga agauccuaug  12300
aggccuuucu uucucagugc cagguggaua uucccaccug gggaacuaga cauccccugg  12360
ggaugcuuug gcaccauaag gugucaaccc ugauugauga aauggugucg cgucggaugu  12420
accgcaccau ggaaaaagca ggacaggcug ccuggaaaca gguggugagc gaggccacgc  12480
ugucucgcau uagugguuug gauguggugg cucauuuuca gcaucuugcc gccauugaag  12540
ccgagaccug uaaauauuug gccucucggc ugcccaugcu acacaaucug cgcaugacag  12600
ggucaaaugu aaccauagug uauaauagua cuuugaauca gguguuugcu auuuuuccaa  12660
ccccuggauc ccggccaaag cuucaugauu uucagcaaug gcuaauagcu gugcacuccu  12720
ccauauuuuc cuccguugcg gcuucuugua cucuuuuugu ugugcugugg uugcggauuc  12780
caaugcuacg uacuguuuuu gguuuccgcu gguuaggggc aauuuuuccu ucgaacucac  12840
ggugaauuac acggugugu cgccuugccu cacccggcaa gcagccgcug aggucuacga  12900
accaggcagg ucucuuuggu gcaggauagg gcaugaccga uguagugagg aagaccauga  12960
cgaucuaggg uucaugguuc cgucuggccu cucccagcgaa ggccacuuga ccaguguuua  13020
cgccugguug gcguuccugu ccuucagcua cacggcccag uuccaucccg agauauuugg  13080
gauagggaau gugagucaag uuuauguuga caucaagcac caauucaucu gcgccguuca  13140
cgacggggag aacgccaccu ugccucguca ugacaauauu ucagccguau aucagaccua  13200
cuaccaacau caagucgacg gcggcaauug guuucaccua gaauggcugc gccccuucuu  13260
uuccucuugg uugguuuuaa auguuucuug guuucucagg cguucgccug caagccaugu  13320
uucaguucaa gucuuucgga caucaaaacc aacacaaccg cagcaucagg cuuuguuguc  13380
cuccaggaca ucagcugccu uaggcauggc gacucguccu cucagacgau ucgcaaaagc  13440
ucucagugcc gcgcggcgau agggacgccc guguacauca cugucacagc caaugucaca  13500
gaugagaauu auuuacauuc uucugaucuc cuuaugcuuu cuucuugccu uuucuaugcu  13560
ucugagauga gugaaaaggg auucaaggug auguuuggca augugucagg caucguggcu  13620
gugugugucca acuuuaccag cuacguccaa caugucaagg aguuuaccca acgcuccuug  13680
gugggucgauc augugcggcu gcuccauuuc augacaccug agaccaugag gugggcaacc  13740
guuuuagccu guuuucuugc caucuuacug gcaauuugaa uguucaagua uguuggggag  13800
augcuugacc gcgggcuguu gcucgcgauu gcuuucuuug ugguguaucg ugccauuuug  13860
uuuugcugcg cucgucaacg ccaacagcaa cagcagcucu caucuucagu uaauuuacaa  13920
cuugacgcua ugugagcuga auggcacaga uuggcugaaa gacaaauuug auugggcauu  13980
ggagacuuuu gucaucuuuc ccguguugac ucacauuguc ucauauagug cacucaccac  14040
uagccauuuc cuugacacag ucggucuggu uacugugucu acugccgggu ucuaccacgg  14100
gcgguauguu cugaguagca ucuacgcggu cugcgcucug gccgcauuga cuugcuucgu  14160
cauuaggcuu gcgaagaacu gcauguccug gcgcuacucu uguaccagau auacuaacuu  14220
ccuucuggac acuaagggca gacucuaucg cuggcggucg cccguuauca uagagaaagg  14280
```

-continued ggguaagguu gaggucgaag gucaccugau cgaccucaaa agaguugugc uugaugguuc 14340
cguggcaacc ccuuuaacca gaguuucagc ggaacaaugg ggucgucuuu agacgacuuu 14400
ugcuaugaua gcacggcucc acaaaaggug cuuuuggcgu uuuccauuac cuacacgcca 14460
gugaugauau augcucuaaa gguaagucgc ggccgacuuu uagggcuucu gcaccuuuug 14520
aucuuucuga auuguacuuu uaccuucggg uacaugacau gcgugcacuu uaauagcaca 14580
aauaaggucg cgcucacuau gggagcagua guugcacuuc uuuggggggu guacucagcc 14640
auagaaaccu ggaaguucau caccuccaga ugucguuugu gcuugcuagg ccgcaaguac 14700
auucuggccc ccgcccacca cgucgaaagu gccgcgggcu uucauccgau cgcggcaaau 14760
gauaaccacg cauuugucgu ccggcguccc ggcuccacua cgguuaacgg cacauuggug 14820
cccggguuga aaagccucgu guuggguggc agaaaagcug uuaaacaggg aguggoaaac 14880 cuugucaaau augccaaaua acaacggcaa gcagcaaaag aaaaagaggg ggaauggcca 14940
gccagucaau cagcugugcc agaugcuggg uaagaucauc gcccagcaaa accaguccag 15000
aggcaaggga ccggggaaga aaauuaagaa uaaaaacccg gagaagcccc auuuuccucu 15060
agcgacugaa gaugacguca ggcaucacuu caccccuagu gagcggcaau ugugucuguc 15120
gucgauccag acugccuuua accagggcgc uggaaccugu acccuaucag auucagguag 15180
gauaaguuac acuguggagu uuaguuugcc gacgcaucau acugugcgcc ugauccgcgu 15240
cacagcgcca ucaucagcgu aaugggcugg cauuccuuaa gcaccucagu guuagaauug 15300
gaagaaugug uggugaaugg cacugauugg cacugugccu cuaagucacc uauucaauua 15360
gggcgaccgu guggggguua aguuuaauug gcgagaacca ugcggccgaa auu 15413

<210> SEQ ID NO 4
<211> LENGTH: 15413
<212> TYPE: RNA
<213> ORGANISM: Porcine reproductive and respiratory syndrome virus

<400> SEQUENCE: 4
augacguaua gguguuggcu cuaugccuug gcauuuguau ugucaggagc ugcgaccauu 60
gguacagccc aaaacuagcu gcacagaaaa cgcccuucug ugacagcccu cuucagggga 120
gcuuaggggu cugucccuag caccuugcuu ccggaguugc acugcuuuac ggucucucca 180
acccuuuaac caugucuggg auacuugauc ggugcacgug cacccccaau gccagggugu 240
uuauggcgga gggccaaguc uacugcacac gaugucucag ugcacggucu cuccuuccuc 300
ugaaucucca aguuccugag cuuggagugc ugggccuauu uuacaggccc gaagagccac 360
uccgguggac guugccacgu gcauucccca cuguugagug cucccccgcc ggggccugcu 420
ggcuuucugc gaucuuucca auugcacgaa ugaccagugg aaaccugaac uuucaacaaa 480
gaauggugcg ggucgcagcu gagauuuaca gagccggcca gcucaccccu gcagucuuga 540
aggcucuaca aguuuaugaa cggggguugcc gcugguaccc uauagucgga ccugucccug 600
gaguggccgu uuuugccaac ucccuacaug ugagugauaa accuuucccg ggagcaacuc 660
augugcuaac caaccugcca cucccgcaga ggccuaagcc ugaagacuuu ugcccuuuug 720
agugugcuau ggcugacguc uaugauauug gucauggcgc cgucauguau guggccaaag 780
ggaaagucuc cugggccccu cguggcgggg augaggcgaa auuugaaacu gucccuaggg 840
aguugaaguu gaucgcgaac caacuccaca ucuccuuccc gccccaccac gcaguggaca 900
ugucuaaguu uguguucaua gccccuggga guggugucuc uaugcggguc gagugcccac 960

-continued

```
acggcugucu ccccgcuaau acugucccug aagguaacug cugguggcgc uuguuugacu   1020
cgcucccacu ggacguucag aacaaagaaa uucgccgugc caaccaauuc ggcuaucaaa   1080
ccaagcaugg ugucgcuggc aaguaccuac aacggaggcu gcaagcuaau ggucuccgag   1140
cagugacuga uacagaugga cccauugucg uacaguauuu cucuguuagg gagagcugga   1200
uccgccacuu cagacuggcg gaagagccua gccucccugg guuugaagac cuccucagaa   1260
uaaggguaga gcccaauacg ucgccauuga gugacaaggg uggaaaaauc uuccgguuug   1320
gcagucacaa augguacggu gcuggaaaga gagcaaggaa agcacgcucu gguaugacca   1380
ccacagucgc ucaccgcgcc uugcccgcuc gugaaaucca gcaagccaaa aagcacgagg   1440
augccggcgc ugauaaggcu gugcaucuca ggcacuauuc uccgccugcc gacgggaacu   1500
gugguuggca cugcauuucc gccaucgcca accgaauggu gaauuccaaa uuugaaacua   1560
cucuucccga gaggguggaga ccuucagaug acugggcuac ugacgaggac cuugugaaca   1620
ccauccaaau ucucaagcuc ccugcggccu uggacaggaa cggugcuugu guuggcgcca   1680
aauacgugcu uaagcuggaa ggcgagcauu ggacugucuc ugugacccuu gggaugucc   1740
cuucuuugcu cccccuugaa uguguucagg gcuguuguga gcauaagagc ggacuugguc   1800
ccccagaugc ggucgaaguu uucggauuug acccugccug ccuugaccga cuggcugagg   1860
uaaugcacuu gccuagcagu gucaucccag cugcucuggc cgaaaugucc ggcgacccca   1920
acuguccggc uuccccgguc acuacugugu ggacuguuuc acaauucuuu gcccgccaca   1980
gaggaggaga gcacccugau cagggugcgcu uaggaaaaau caucagccuu ugucaaguug   2040
uugaggaaug cuguugccau cagaauaaaa ccaaccgggc caccccggaa gagguugcgg   2100
caaggauuga ucaguaccuc caugggugcaa caagucuuga agaaugcuug auuaggcuug   2160
agaggguuug cccgccgagc gcugcggaca ccuucuuuga uuggaauguu gugcucccug   2220
ggguuggggc uucaacucag acaaccaaac agcuccaugu caaccagugc cgcgcucugg   2280
uuccugucgu gacucaagag ccuuuggaca aagacucagu cccucugacc gccuucucgc   2340
uguccaauug cuacuauccu gcacaaggug acgagguucg ucaccgugag aggcuaaacu   2400
ccguacucuc uaagcuggag gggguuguuc gugaggaaua ugggcucacg ccaacugaac   2460
cuggcccgcg acccgcacua ccgaacgggc ucgucgaacu uaaagaccag auggaggagg   2520
aucugcugaa acuagucaac gcccaggcaa cuucagaaau gauggccugg gcagccgagc   2580
agguugaucu gaaagcuugg gucaaaaacu acccacggug gacaccgcca cccccuccac   2640
caagaguuca gccucgaaaa acaaagucug ucaagagcuu gccagggaac aaaccugucc   2700
ccgcuccacg caggaagguc agaucugauu guggcagccc gauuuugaug ggcgacaaug   2760
uuccugacgg ucgggaagau uugacuguug guggcccccu ugaucuuucg acaccauccg   2820
agccgaugac accucugagu gagccugcac uuaugcccgc guugcaauau auuucuaggc   2880
cagugacauc uuugagugug cuggccccag uuccugcacc gcguagaacu guguccccgac   2940
cggugacgcc cuugagugag ccaauuuuug ugucugcacc gcgacacaaa uuucagcagg   3000
uggaagaagc gaaucuggcg gcaacaacgc ugacgcacca ggacgaaccu cuagauuugu   3060
cugcauccuc acagacugaa uaugaggcuu cucccccuaac accacugcag aacaugggua   3120
uucuggaggu gggggggcaa gaagcugagg aaguucugag ugaaaucucg gauacacuga   3180
augacaucaa cccugcaccu gugucaucaa gcagcucccu gucaaguguu aagaucacac   3240
gcccaaaaca cucugcucaa gccaucauug acucgggcgg gcccugcagu gggcaucucc   3300
gaagggaaaa agaagcaugc cucagcauca ugcgugaggc uugugaugcg gcuaagcuua   3360
```

-continued gugacccugc cacgcaggaa uggcuuucuc gcauguggga uaggguugac augcugacuu 3420
ggcgcaacac gucugcuuac caggcguucc gcaucuuaga ugguagguuu gaguuucucc 3480
caaagaugau acucgagaca ccgccgcccu acccgugugg guuugugaug cugccucaca 3540
cgccugcacc uuccgugggu gcagagagug accuuaccau ugguucaguc gccacugaag 3600
auguuccacg cauccucggg aaaauagaaa acgccggcga gaugcccaac caggggcucu 3660
ugacauccuu cggggaagaa ccggugugcg accaaccugu caaggacucc uggaugucgu 3720
cgcgggggguu ugacgagagc acaacggcuc cguccgcugg uacaggugu gcugacuuac 3780
ccaccgauuu gccaccuuca gaugguuugg augcggacga gugggggccg uuacggacgg 3840
uaagaaagaa agcugaaagg cucuucgacc aauugagccg ucagguuuuu aaccucgucu 3900
cccaucuccc uguuuucuuc ucacaccucu ucaaaucuga cagugguuau ucuccgggug 3960
auuggggguu ugcagcuuuu acuuuauuuu gccucuuuuu guguuacagc uacccauucu 4020
uugguuuugu uccccucuug gguguuuuuu cugggucuuc ucggcgugug cgcauggggg 4080
uuuuuggcug uugguuggcu uuugcuguug gccuguucaa gccuguguccc gacccagucg 4140
gcacugcuug ugaguuugac ucgccagagu guaggaacgu ccuucauucu uuugagcuuc 4200
ucaaaccuug ggacccuguu cgcagccuug uugugggccc cgucggucuc ggccuugcca 4260
uucuuggcag guuacugggc ggggcacgcu acaucuggca uuuuuugcuu aggcuuggca 4320
uuguugcaga uuguaucuug gcuggagcuu augugcuuuc ucaagguagg uguaaaaagu 4380
gcuggggauc uuguguaaga acugcuccua augaaaucgc cuucaacgug uucccuuuua 4440
cgcgugcgac caggucguca cucaucgacc ugugcgaucg guuuugugcg ccaaaaggca 4500
uggaccccau uuuccucgcu acuggguggc gcgggugcug gaccggccga agucccauug 4560
agcaacccuc ugaaaaaccc aucgcguucg cccaguugga ugaaaagagg auuacggcua 4620
gaacuguggg cgcucagccu uaugauccua accaagccgu aaagugcuug cggguguuac 4680
aggcgggugg ggcgauagug gccgaggcag ucccaaaagu ggucaagguu uccgcuauuc 4740
cauuccgagc ucccuuuuuu cccaccggag ugaagguuga uccugagugc aggaucgugg 4800
ucgaccccga cacuuuuacu acagcucucc ggucugguua cuccaccaca aaccucgucc 4860
uuggugugggg ggacuuugcc caacugaaug gauuaaaaau caggcaaauu uccaagcccu 4920
cgggaggagg cccgcaccuc auugcugccc ugcauguugc uugcucgaug gcguugcaca 4980
ugcuugcugg aguuuaugua acugcagugg ggucuugcgg uaccggcacc aacgauccgu 5040
ggugcacuaa cccauucgcc gucccuggcu acggaccugg cucccucugc acguccagau 5100
ugugcaucuc ccaacauggc cuuacccugc ccuugacagc acuuguggca ggauucgguc 5160
uucaggaaau ugcccuaguc guuuugauuu ucguuuccau cggaggcaug gcucauaggu 5220
ugaguuguaa ggcugauaug cugugcgucu uacuugcaau cgccagcuau guuuggguac 5280
cccuuaccug guugcucugu guguuucccuu gcugguugcg cugguucucu uugcacccuc 5340
ucaccauucu augguuggug uuuuucuuga ugucuguaaa uaugccuucg ggaaucuuaa 5400
ccgugguguu auugguugcu cuuuggcuuc uaggccguua uacuaauguu guuggucuug 5460
uuacccccua ugauauucau cauuacacca auggcccccg cgguguugcc gccuuggcua 5520
ccgcaccaga ugggacuuac uuggccgcug uccgccgcgc ugcguugacu ggccgcaccg 5580
ugcuguuuac cccgucucag cuugggucccc uucuugaggg cgcuuucaga acucgaaagc 5640
ccucacugaa caccgucaau guggucgggu ccuccauggg cucuggcgga guguucacua 5700

-continued

```
ucgaugggaa aauuaagugc gugacugccg cacauguccu uacggguaau ucagccaggg   5760
uuuccggggu cggcuucaau caaaugcuug acuuugaugu aaaaggggac uucgccauag   5820
cugauugccc gaauuggcaa ggggcugcuc cuaagaccca auucugcgag gauggaugga   5880
cuggccgcgc cuauuggcug acauccucug gcgucgaacc cggugucauu gggaauggau   5940
ucgccuucug cuucaccgcg ugcggcgauu ccggguoccc agugaucacc gaagccggug   6000
agcuugucgg cguucacaca ggaucaaaca aacaaggagg aggcauuguu acgcgccccu   6060
cuggccaguu uugcaaugug gcacccauca agcugagcga auuaagugag uucuuugcug   6120
gaccuaaggu cccgcucggu gaugugaagg uuggcagcca cauaauuaaa gacauaugcg   6180
agguaccuuc agaucuuugc gccuugcuug cugccaaacc cgaacuggaa ggaggccucu   6240
ccaccgucca acuucugugu guguuuuucc uccuguggag aaugauggga caugccugga   6300
cgcccuuggu ugcuguuggg uuuuuuaucu ugaaugaggu ucucccagcu guacuggucc   6360
ggaguguuuu cuccuuugga auguuugugc uaucuuggcu cacaccaugg ucugcgcaag   6420
uucugaugau caggcuucua acagcagcuc uuaacaggaa cagauuguca cucgccuuuu   6480
acagccuugg ugcagcgacc gguuuugucg cagaucuggc ggcaacucaa gggcacccgu   6540
ugcaggcagu aaugaauuua aguaccuaug ccuuccugcc ucggauaaug gucgugaccu   6600
caccaguccc agugauugcg ugugguguug ugcaccuccu ugccauaauu uuguacuugu   6660
uuaaguaccg cugccugcac aauguccuug uuggcgaugg ugcguucucu gcggcuuucu   6720
ucuugcgaua cuuugccgag gggaaauuga gggaaggggu gucgcaaucc ugcgggauga   6780
aucaugaguc gcugacuggu gcccucgcua ugagacuuaa ugacgaggac uuggauuuuc   6840
uuacgaaaug gacugauuuu aaguguuuug uuucugcauc caacaugagg aaugcggcgg   6900
gccaguucau cgaggcugcc uaugcuaaag cacuuagaau ugaacuugcc caguuggugc   6960
agguugauaa gguucgaggu acuuuggcca aacuugaagc uuuugcugau accguggcac   7020
cccaacucuc gcccggugac auuguuguug cucuuggcca uacgccuguu ggcgguaucu   7080
ucgaccuaaa gguugguagc accaagcaua cccuccaagc cauugagacc agaguucuug   7140
ccggguccaa aaugaccgug gcgcgugucg uugauccaac ccccacaccc ccacccgcac   7200
ccgugccuau cccccuucca ccgaaaguuc uggagaaugg ucccaacgcc ugggggggaug   7260
aggaucguuu gaauaagaag aagaggcgca ggauggaagc cgucggcauc uuuguuaugg   7320
guggaaagaa auaucagaaa uuuugggaca agaacuccgg ugauguguuu uaugaggagg   7380
uccaugauaa cacagacgcg ugggagugcc ucagaguuga caacccugcc gacuuugacc   7440
cugagaaggg aacucugugc gggcauacua ccauugaaga uaagacuuac agugucuacg   7500
ccuccccauc uggcaagaaa uuccuggucc ccgucuaccc agagagcaaa aaaaaccaau   7560
gggaagcugc gaagcuuucc guggaacagg cccuuggcau gaugaauguc gacggugaac   7620
ugacagccaa agaaguggag aaacugaaaa gaauaauuga caaacuccag ggccugacua   7680
aggagcagug uuuaaacugc uagccgccag cggcuugacc cgcugugguc gcggcggcuu   7740
gguuguuacu gagacagcgg uaaaaauagu caaauuucac aaccggaccu ucacccuagg   7800
accugugaau uuaaaagugg ccagugaggu ugagcuaaaa gacgcggucg agcauaacca   7860
acacccgguu gcaagaccgg uugaugguggg uguugugcuc cugcgcuccg caguuccuuc   7920
gcuuauagac gucuuaaucu ccggcgcuga ugcaucuccc aaguuacucg cccgccacgg   7980
gccgggaaac acugggaucg auggcacgcu uugggauuuu gaggccgagg ccacuaaaga   8040
ggaaauugca cucagugcgc aaauaauaca ggcuugugac auuaggcgcg gcgacgcacc   8100
```

-continued

```
ugaaauuggu cuuccuuaua agcuguaccc ugucaggggc aacccugagc ggguaaaagg   8160
aguuuuacag aauacaaggu uuggagacau accuuauaaa acccccagug acacuggaag   8220
cccagugcac gcggcugccu gccucacgcc caaugccacu ccggugacug augggcgcuc   8280
cgucuuggcc acgacuaugc ccuccgguuu ugaguuguau guaccgacca uuccagcguc   8340
uguccuugau uaucuugauu cuaggccuga cugccccaaa caguugacag agcacggcug   8400
ugaggacgcc gcauuaagag accucuccaa guaugacuug uccacccaag gcuuuguuuu   8460
accuggaguu cuucgccuug ugcguaagua ccuguuugcu caugugggua agugcccgcc   8520
cguucaucgg ccuuccacuu acccugccaa gaauucuaug gcuggaauaa augggaacag   8580
guuuccaacc aaggacaucc agagcguccc ugaaaucgac guucugugcg cacaggccgu   8640
gcgggaaaac uggcaaacug uuaccccuug uacccucaag aaacaguauu gugggaagaa   8700
gaagacuagg acaauacucg gcaccaauaa cuucauugcg cuggcccacc gggcagcguu   8760
gaguggugu acccagggcu ucaugaaaaa ggcguuuaac ucgcccauug cccucgguaa   8820
aaacaaauuu aaagagcuuc agacuccggu cuuaggcagg ugccuugaag cugaucuugc   8880
auccugcgau cgcuccacac cugcaauugu ccgcugguuu gccgccaauc uucuuuauga   8940
acuugccugu gcugaagagc accugccguc guacguguug aacugcugcc acgaccuacu   9000
ggucacgcag uccggcgcag uaacuaagag agguggccug ucgucuggcg acccgaucac   9060
uucugugucc aacaccauuu acagcuuggu gauauaugca caacacaugg ugcucaguua   9120
cuuuaaaagu ggucacccuc auggccuucu guuucuacaa gaccagcuga aguuugagga   9180
caugcucaag guucaacccc ugaucgucua uucggacgac cucguacugu augccgaguc   9240
ucccaccaug ccaaacuacc acugguggu ugaacaucug aaccugaugc uggguuuuca   9300
gacggaccca aagaagacag ccauaacaga cucgccauca uuucuaggcu guaggauaau   9360
aaauggacgc cagcucgucc cuaaccguga caggauucuc gcggcccucg ccuaccauau   9420
gaaggcaagc aaugucucug aauacuacgc cucggcggcu gcgauacuca uggacagcug   9480
ugcuuguuua gaguaugauc ccgaaugguu ugaagagcuu guaguuggga uagcgcagug   9540
ugcccgcaag gacggcuaca guuuucccgg cccgccguuc uucuugucca ugugggaaaa   9600
acucagaucc aaucaugagg ggaagaaguc cagaaugugc ggguacugcg gggccccggc   9660
uccguacgcc acugccugug gccucgacgu cuguauuuac cacacccacu uccaccagca   9720
uuguccaguc aucaucuggu guggccaccc ggcugguucu gguucuugua gugagugcaa   9780
acccccccua gggaaaggca caagcccucu agaugaggug uuagaacaag ucccguauaa   9840
gccuccacgg acuguaauca ugcauugga gcagggucuc accccucuug acccaggcag   9900
auaccagacu cgccgcggau uagucuccgu uaggcguggc auuagaggaa augagguuga   9960
ucuaccagac ggugauuaug cuagcaccgc ccuacucccu acuuguaaag agauuaacau  10020
ggucgcuguc gccucuaaug uguugcgcag cagguucauc aucggcccgc cuggugcugg  10080
gaaaacauac uggcuccuuc aacaggucca ggauggugau gucauuuaca cgccaacuca  10140
ccagaccaug cucgauauga uuagggcuuu ggggacgugc cgguucaacg ucccagcagg  10200
uacgacgcug caauucccug cccccucccg uaccggcccu uggguucgca uccuagccgg  10260
cgguuggugu ccuggcaaga auuccuuccu ggaugaagca gcguauugua aucaccuuga  10320
ugucuugagg cuucuuagca aaacuacccu caccugucug ggagauuuca aacaacucca  10380
cccagugggu uuugauucuc auugcuaugu uuuugacauc augccucaga cucaacugaa  10440
```

-continued

```
gaccaucugg agauuuggac agaauaucug ugaugccauu cagccagauu acagggacaa  10500
acuuguaucc auggucaaca caacccgugu aaccuacgug gaaaaaccug ucaaguaugg  10560
gcaaguccuc accccuuacc acagggaccg agaggacggc gccaucacaa uugacuccag  10620
ucaaggcgcc acauuugaug ugguuacacu gcauuugccc acuaaagauu cacucaacag  10680
gcaaagagcc cuuguugcua uuaccagggc aagacaugcu aucuuugugu augacccaca  10740
caggcaacug cagagcaugu uugaucuucc ugcgaaaggc acacccguca accucgcugu  10800
gcaccgugac gagcagcuga ucgugcuaga uagaaauaac aaagaaugca cgguugcuca  10860
ggcucuaggc aaugggggaua aauucagggc cacagacaag cgcguuguag auucucuccg  10920
cgccauuugu gcagaucugg aagggucgag cuccccgcuc cccaaggucg cacacaacuu  10980
gggauuuuau uucucgccug auuugacaca guuugcuaaa cucccgguag aacuugcacc  11040
ccacuggccc guggugacaa cccagaacaa ugaaaagugg ccagaccggu ugguugcuag  11100
ccuucgcccc guccauaagu auagccgcgc gugcaucggu gccggcuaca ugguggggccc  11160
cucaguguuu cugggcaccc cugggguugu gucauacuau cucacaaaau uugucagggg  11220
cgaggcucaa augcuuccgg agacagucuu cagcaccggc cgaauugagg uagauugccg  11280
ugaguaucuu gaugaccggg agcgagaaau ugcugagucc cucccccaug cuuucauugg  11340
cgacgucaaa ggcacuaccg uuggaggaug ucaccauguc accuccaaau accuuccgcg  11400
cuuccuuccc aaggaaucag ucgcgguagu cgggguuuca agccccggga aagccgcaaa  11460
agcaguuugc acauuaacag auguguaucu cccagaucuc gaagcuuacc uccacccaga  11520
gacccagucc aagugcugga aaaugauguu ggacuucaag gaaguucgac ugauggucug  11580
gaaggacaag acggccuauu uucaacuuga aggccgccau uucaccuggu accagcuugc  11640
aagcuaugcc ucguacaucc gaguuccugu uaacucuacg guguauuugg accccugcau  11700
gggcccugcc cuuugcaaca gaagaguugu cggguccacu cauuggggag cugaccucgc  11760
agucaccccu uaugauuacg gugccaaaau cauccugucu agugcauacc augugaaau  11820
gcccccuggg uacaaaaucc uggcgugcgc ggaguucucg cuugacgauc cagugaggua  11880
caaacacacc ugggggguuug aaucggauac agcguaucug uacgaguuca ccggaaacgg  11940
ugaggacugg gaggauuaca augaugcguu ucgugcgcgc cagaaaggga aaauuuauaa  12000
ggccacugcc accagcauga gguuucauuu ucccccgggc ccugucauug aaccaacuuu  12060
aggccugaau ugaaaugaaa ugggguccau gcaaagccuc uuugacaaaa uuggccaacu  12120
uuuuguggau gcuuucacgg aauuuuuggu guccauuguu gauaucauca uauuuuuggc  12180
cauuuuguuu ggcuuuacca ucgcuggcug gcugguggcuc uucugcaucc gauugguuug  12240
cuccgcggua cuccgugcgc gcccuaccau ucacccugag caauuacaga agauccuaug  12300
aggccuuucu uucucagugc cagguggaua uucccaccug gggaacuaga cauccccugg  12360
ggauguuuug gcaccauaag gugucaaccc ugauugauga aauggugucg cgucggaugu  12420
accgcaccau ggaaaaagca ggacaggcug ccuggaaaca gguggugagc gaggccacgc  12480
ugucucgcau uaguggguuug gauguggugg cucauuuuca gcaucuugcc gccauugaag  12540
ccgagaccug uaaauauuug gccucucggc ugcccaugcu acacaaucug cgcaugacag  12600
ggucaaaugu aaccauagug uauaauagua cuuugaauca gguguuugcu auuuuuccaa  12660
ccccuggauc ccggccaaag cuucaugauu uucagcaaug gcuaauagcu gugcacuccu  12720
ccauauuuuc cuccguugcg gcuucuugua cucuuuuugu ugugcugugg uugcggauuc  12780
caauacuacg uacuguuuuu gguuuccgcu gguuaggggc aauuuuuccu ucgaacucac  12840
```

-continued

```
ggugaauuac acggugugu cgccuugccu cacccggcaa gcagccgcug aggucuacga  12900
accaggcagg ucucuuuggu gcaggauagg gcaugaccga uguagugagg acgaccauga  12960
cgaucuaggg uucaugguuc cgccuggccu cuccagcgaa ggccacuuga ccaguguuua  13020
cgccugguug gcguuccugu ccuucagcua cacggcccag uuccaucccg agauauuugg  13080
gauagggaau gugagucaag uuuauguuga caucaagcac caauucaucu gcgccguuca  13140
cgacggggag aacgccaccu ugccucguca ugacaauauu ucagccguau uucagaccua  13200
cuaccaacau caagucgacg gcggcaauug guuucaccua gaauggcugc gccccuucuu  13260
uuccucuugg uugguuuuaa auguuucuug guuucucagg cguucgccug caagccaugu  13320
uucaguucaa gucuuucgga caucaaaacc aacacuaccg cagcaucagg cuuuguuguc  13380
cuccaggaca ucagcugccu uaggcauggc gacucguccu cucagacgau ucgcaaaagc  13440
ucucagugcc gcgcggcgau agggacgccc guguacauca cugucacagc caaugucaca  13500
gaugagaauu auuuacauuc uucugaucuc cuuaugcuuu cuucuugccu uuucuaugcu  13560
ucugagauga gugaaaaggg auucaaggug auauuuggca augugucagg caucguggcu  13620
gugugugucaa acuuuaccag cuacguccaa caugucaagg aguuuaccca acgcuccuug  13680
gugguucgauc augugcggcu gcuccauuuc augacaccug agaccaugag gugggcaacc  13740
guuuuagccu guuuuuuugc caucuuacug gcaauuugaa uguucaagua uguuggggag  13800
augcuugacc gcgggcuguu gcucgcgauu gcuuucuuug ugguguaucg ugccauuuug  13860
uuuugcugcg cucgucaacg ccaacagcaa cagcagcucu caucuucagu ugauuuacaa  13920
cuugacgcua ugugagcuga auggcacaga uuggcugaaa gacaaauuug auugggcagu  13980
ggagacuuuu gucaucuuuc ccguguugac ucacauuguc ucauauggug cacucaccac  14040
uagccauuuc cuugacacag ucggucuggu uacugugucu accgccgggu ucuaccacgg  14100
gcgguauguu cugaguagca ucuacgcggu cugcgcucug gccgcauuga uuugcuucgu  14160
cauuaggcuu gcgaagaacu gcauguccug gcgcuacucu uguaccagau auacuaacuu  14220
ccuucuggac acuaagggca gacucuaucg cuggcggucg cccguuauca uagagaaagg  14280
ggguaagguu gaggucgaag gucaccugau cgaccucaaa agaguugugc uugaugguuc  14340
cguggcaacc ccuuuaacca gaguuucagc ggaacaaugg ggucgucuuu agacgacuuu  14400
ugcuaugaua gcacggcucc acaaaaggug cuuuuggcgu uuuccauuac cuacacgcca  14460
gugaugauau augcucuaaa gguaagucgc ggccgacuuu uagggcuucu gcaccuuuug  14520
aucuuucuga auuguacuuu uaccuucggg uacaugacau ucgugcacuu uaauagcaca  14580
aauaaggucg cgcucacuau gggagcagua guugcacuuc uuuggggggu guacucagcc  14640
auagaaaccu ggaaguucau caccuccaga ugccguuugu gcuugcuagg ccgcaaguac  14700
auucuggccc ccgcccacca cgucgaaagu gccgcgggcu uucauccgau cgcggcaaau  14760
gauaaccacg cauuugucgu ccggcguccc ggcuccacua cgguuaacgg cacauuggug  14820
cccggguuga aaagccucgu guugggguggc agaaaagcug uuaaacaggg agugguaaac  14880
cuugucaaau augccaaaua acaacggcaa gcagcaaaag aaaaagaggg ggaauggcca  14940
gccagucaau cagcugugcc agaugcuggg uaagaucauc gcccagcaaa accaguccag  15000
aggcaaggga ccggggaaga aaauuaagaa uaaaaacccg gagaagcccc auuuuccucu  15060
agcgacugaa gaugacguca ggcaucacuu caccccuagu gagcggcaau ugugucuguc  15120
gucgauccag acugccuuua accagggcgc uggaaccugu acccuaucag auucagguag  15180
```

-continued

```
gauaaguuac acuguggagu uuaguuugcc gacgcaucau acugugcgcc ugauccgcgu  15240

cacagcgcca ucaucagcgu aaugggcugg cauuccuuaa gcaccucagu guuagaauug  15300

gaagaaugug uggugaaugg cacugauugg cacugugccu cuaagucacc uauucaauua  15360

gggcgaccgu gugggguua aguuuaauug gcgagaacca ugcggccgaa auu         15413
```